(12) United States Patent
Kincaid et al.

(10) Patent No.: US 11,542,271 B2
(45) Date of Patent: *Jan. 3, 2023

(54) FUSED HETEROAROMATIC-ANILINE COMPOUNDS FOR TREATMENT OF DERMAL DISORDERS

(71) Applicant: NFlection Therapeutics, Inc., Chestnut Hill, MA (US)

(72) Inventors: John Kincaid, Chestnut Hill, MA (US); Matthew Duncton, Chestnut Hill, MA (US)

(73) Assignee: NFLECTION THERAPEUTICS, INC., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/235,018

(22) Filed: Apr. 20, 2021

(65) Prior Publication Data

US 2021/0380601 A1 Dec. 9, 2021

Related U.S. Application Data

(63) Continuation of application No. 16/615,059, filed as application No. PCT/US2018/033544 on May 18, 2018, now Pat. No. 10,988,483.

(60) Provisional application No. 62/508,997, filed on May 19, 2017.

(51) Int. Cl.
*C07D 495/04* (2006.01)

(52) U.S. Cl.
CPC ................. *C07D 495/04* (2013.01)

(58) Field of Classification Search
CPC ...................................... C07D 495/04
See application file for complete search history.

(56) References Cited

U.S. PATENT DOCUMENTS

| | | | |
|---|---|---|---|
| 8,283,359 B2 | 10/2012 | Hutchings et al. | |
| 10,988,483 B2 * | 4/2021 | Kincaid | C07D 495/04 |
| 11,161,845 B2 | 11/2021 | Kincaid et al. | |
| 2020/0165243 A1 | 5/2020 | Kincaid et al. | |
| 2020/0172550 A1 | 6/2020 | Kincaid et al. | |
| 2022/0033399 A1 | 2/2022 | Kincaid et al. | |

FOREIGN PATENT DOCUMENTS

| | | |
|---|---|---|
| CN | 105384754 A | 3/2016 |
| WO | WO-2006130160 A2 | 12/2006 |
| WO | WO-2007002433 A1 | 1/2007 |
| WO | WO-2007088345 A1 | 8/2007 |
| WO | WO-2008020206 A2 | 2/2008 |
| WO | WO-2008024724 A1 | 2/2008 |
| WO | WO-2008024725 A1 | 2/2008 |
| WO | WO-2008055236 A2 | 5/2008 |
| WO | WO-2008067481 A1 | 6/2008 |
| WO | WO-2008148034 A1 | 12/2008 |
| WO | WO-2009082687 A1 | 7/2009 |
| WO | WO-2009093008 A1 | 7/2009 |
| WO | WO-2009093009 A1 | 7/2009 |
| WO | WO-2009093013 A1 | 7/2009 |
| WO | WO-2009153554 A1 | 12/2009 |
| WO | WO-2012040636 A2 | 3/2012 |
| WO | WO-2014179785 A1 | 11/2014 |
| WO | WO-2018213807 A1 | 11/2018 |
| WO | WO-2018213810 A1 | 11/2018 |

OTHER PUBLICATIONS

Adams et al., Design and Synthesis of Orally Available MEK Inhibitors With Potent in Vivo Antitumor Efficacy, Bioorganic & Medicinal Chemistry Letters, 2012, 22(7), pp. 2411-2414.
Akinleye et al., MEK and the Inhibitors: From Bench to Bedside, Journal of Hematology & Oncology, 2013, 6(27), 11 pages.
Hatzivassiliou et al., Mechanism of MEK inhibition determines efficacy in mutant KRAS- versus BRAF-driven cancers, Nature, 2013, 501(7466), pp. 232-236.
International Search Report and Written Opinion for International PCT Application No. PCT/US2018/033544 dated Aug. 9, 2018 (11 pages).
International Search Report and Written Opinion for International PCT Application No. PCT/US2018/033547, dated Aug. 9, 2018 (10 pages).
Laing et al., Fused Thiophene Derivatives as MEK Inhibitors, Bioorganic & Medicinal Chemistry Letters, 2012, 22(1), pp. 472-475.
Wallace et al., Structure-based Design and Synthesis of Pyrrole Derivatives as MEK Inhibitors, Bioorganic & Medicinal Chemistry Letters, 2010, 20(14), pp. 4156-4158.

(Continued)

*Primary Examiner* — Timothy R Rozof
(74) *Attorney, Agent, or Firm* — Mintz, Levin, Cohn. Ferris, Glovsky & Popeo, P.C.

(57) ABSTRACT

Provided herein are compounds, pharmaceutical compositions comprising the compounds, methods of preparing the compounds, and methods of using the compounds and compositions in treating diseases or disorders in a subject where the subject is in need of an inhibitor of MEK where the Compound is according to Formula (I):

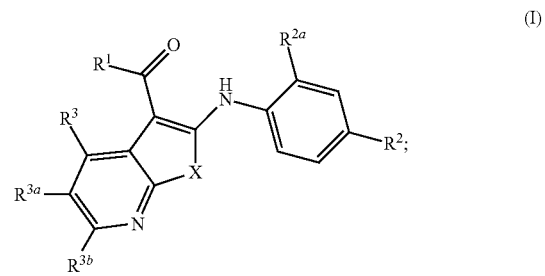

where X, $R^1$, $R^2$, $R^{2a}$, $R^3$, $R^{3a}$, and $R^{3b}$ are as described herein.

13 Claims, 2 Drawing Sheets

(56) References Cited

OTHER PUBLICATIONS

RN 1347327-80-3 Registry ED Entered STN: Dec. 2, 2011.
RN 1347341-78-9 Registry ED Entered STN: Dec. 2, 2011.
RN 1347421-15-1 Registry ED Entered STN: Dec. 2, 2011.
RN 1348075-68-2 Registry ED Entered STN: Dec. 4, 2011.
RN 1348201-64-8 Registry ED Entered STN: Dec. 4, 2011.
RN 1348347-40-9 Registry ED Entered STN: Dec. 4, 2011.
RN 1348375-35-8 Registry ED Entered STN: Dec. 4, 2011.
RN 1348394-69-3 Registry ED Entered STN: Dec. 4, 2011.
RN 1348492-53-4 Registry ED Entered STN: Dec. 4, 2011.
RN 1348494-88-1 Registry ED Entered STN: Dec. 4, 2011.
RN 1348595-42-5 Registry ED Entered STN: Dec. 4, 2011.
RN 1348618-58-5 Registry ED Entered STN: Dec. 4, 2011.
RN 1348655-12-8 Registry ED Entered STN: Dec. 4, 2011.
RN 1348673-54-0 Registry ED Entered STN: Dec. 4, 2011.
RN 1349147-82-5 Registry ED Entered STN: Dec. 5, 2011.
RN 1349255-80-6 Registry ED Entered STN: Dec. 5, 2011.
RN 1349369-24-9 Registry ED Entered STN: Dec. 6, 2011.
RN 1349383-92-1 Registry ED Entered STN: Dec. 6, 2011.
RN 1349420-35-4 Registry ED Entered STN: Dec. 6, 2011.
RN 1349476-92-1 Registry ED Entered STN: Dec. 6, 2011.
RN 1349510-77-5 Registry ED Entered STN: Dec. 6, 2011.
RN 1349524-53-3 Registry ED Entered STN: Dec. 6, 2011.
RN 1349623-68-2 Registry ED Entered STN: Dec. 6, 2011.
RN 1349668-73-0 Registry ED Entered STN: Dec. 6, 2011.
RN 1349887-30-4 Registry ED Entered STN: Dec. 6, 2011.
RN 1349985-90-5 Registry ED Entered STN: Dec. 7, 2011.

\* cited by examiner

FIG. 1 Compound of Example 8 in a Topical Gel Formulation (1%) Suppresses p-ERK in Human Cutaneous Neurofibroma Explants
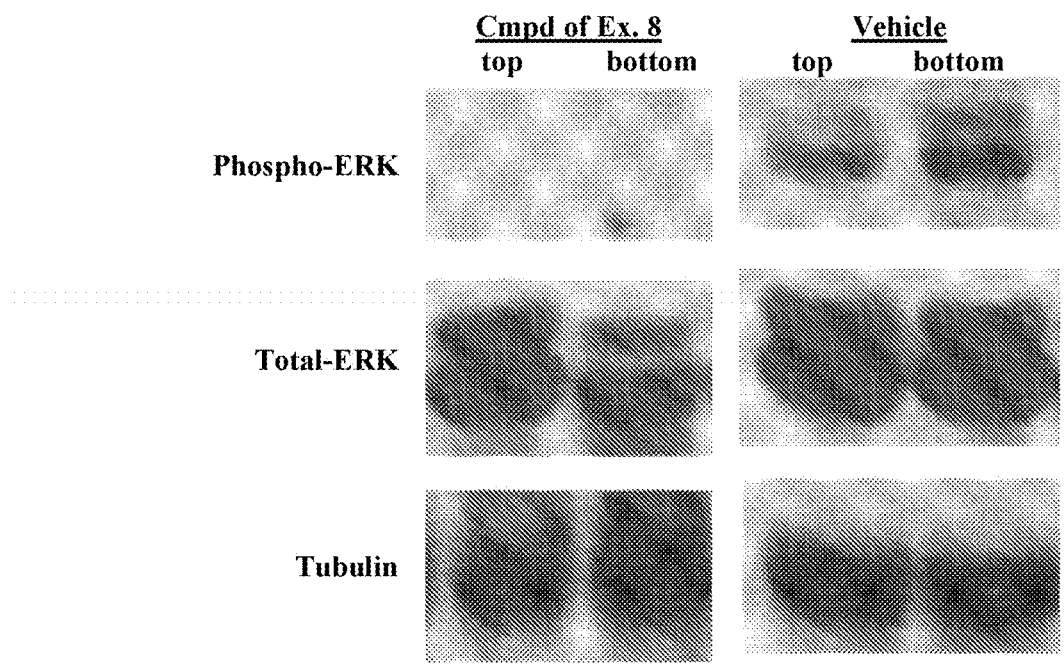

FIG. 2 Compound of Example 8 in a Topical Gel Formulation (1%) Suppresses p-ERK in Human Cutaneous Neurofibroma Explants
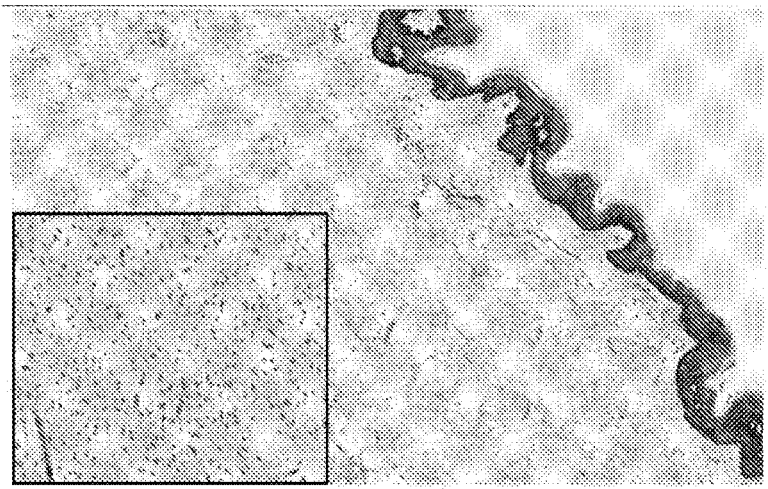
Vehicle
Cmpd of Ex. 8, topical gel formulation

FUSED HETEROAROMATIC-ANILINE COMPOUNDS FOR TREATMENT OF DERMAL DISORDERS

CROSS-REFERENCE TO RELATED APPLICATIONS

This application is a continuation of U.S. patent application Ser. No. 16/615,059, filed Nov. 19, 2019, which is a U.S. National Phase Application of PCT International Application No. PCT/US2018/033544, filed May 18, 2018, which claims the benefit of U.S. provisional application 62/508,997 filed on May 19, 2017, the contents of which is incorporated herein by reference in its entirety.

FIELD

Provided herein are compounds, pharmaceutical compositions comprising the compounds, and methods of using the compounds and compositions that are useful in treating dermal diseases or dermal disorders associated therewith. Also provided herein are methods of treating diseases or disorders in a mammal comprising administering a therapeutically or prophylactically effective amount of a compound or composition disclosed herein to a mammal.

BACKGROUND

Neurofibromatosis type 1 (NF1) occurs in approximately 1:3,500 births, and is one of the most common autosomal dominant single-gene disorders affecting neurological function in humans. Clinically, NF1 disease is characterized by the presence of benign peripheral nerve tumors, called neurofibromas, involving Schwann cells with biallelic mutations in the NF1 gene, as well as other tumor and non-tumor manifestations. (Jousma et al. *Pediatr. Blood Cancer* 62: 1709-1716, 2015). NF1 is associated with several dermal disorders, including dermal neurofibromas or cutaneous neurofibromas; plexiform neurofibromas; café au lait spots; and axillary and inguinal freckling. Dermal neurofibromas or cutaneous neurofibromas occur in over 95% of NF1 patients, can appear anywhere on the body, causing itching, irritation, infection, physical pain, and disfigurement. Moreover, dermal neurofibromas or cutaneous neurofibromas are associated with social isolation and anxiety.

NF1 is caused by one or more germ line mutations in NF1, a gene that inactivates the RAS pathway. Because the NF1 gene encodes a Ras-GAP protein, NF1 loss results in high Ras-GTP. Therefore, NF1 research has focused intensively on testing inhibitors in the Ras signaling pathway, including the Ras-MAPK cascade. (Jousma et al. *Pediatr. Blood Cancer* 62: 1709-1716, 2015). Four distinct MAPK cascades have been identified and named according to their MAPK module. (Akinleye et al. *Journal of Hematology & Oncology* 6:27, 2013). MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras, and thus provide a rationale for targeting MEK in the treatment of NF1. (Rice et al. *Medicinal Chemistry Letters* 3:416-421, 2012).

Currently available MEK inhibitors are designed to have oral bioavailability for systemic delivery, and are associated with significant side effects including decreased left ventricular ejection fraction, elevated creatine phosphokinase, pneumonitis, renal failure, diarrhea, infection, uticaria, and maculo-papular rash, all of which are dose limiting or require permanent discontinuation. Moreover, clinical trials have shown side effects with prolonged high-dose administration of MEK inhibitors. (Huang et al. *J. Ocul. Pharmacol. Ther.* 25:519-530, 2009). For example, PD0325901, a clinically-tested MEK inhibitor, has exhibited neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that inhibit MEK to treat NF1 associated dermal neurofibromas or cutaneous neurofibromas, which limit one or more of these serious side effects.

SUMMARY

Provided herein are compounds, pharmaceutical compositions comprising the compounds, and methods of using the compounds and compositions for treating dermal diseases or dermal disorders associated therewith. Also provided herein are methods of treating diseases or disorders in a mammal comprising administering a therapeutically or prophylactically effective amount of a compound or composition disclosed herein to a mammal. In an embodiment, the mammal is a human.

In one aspect, provided is a Compound of Formula (IA):

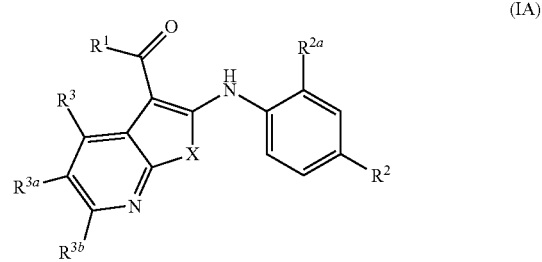

(IA)

where
$R^1$ is —$OR^4$, —$NR^5R^{5a}$, or an N-linked heterocycloalkyl where the N-linked heterocycloalkyl is optionally substituted with one or two $R^{10}$;

$R^{2a}$ is halo or $C_1$-$C_6$ alkyl;

$R^2$ is —S—$C_1$-$C_6$ alkyl, $C_1$-$C_6$ alkyl, $C_2$-$C_6$ alkenyl, $C_2$-$C_6$ alkynyl, or halo;

X is —S— or —O—; and when X is —S— and $R^3$, $R^{3a}$, and $R^{3b}$ are hydrogen, then $R^2$ is $C_2$-$C_6$ alkenyl, $C_2$-$C_6$ alkynyl or —S—$C_1$-$C_6$ alkyl;

$R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$;

$R^4$ is hydrogen, $C_1$-$C_6$ alkyl, optionally substituted with one heterocycloalkyl; $C_3$-$C_8$ cycloalkyl, $C_3$-$C_8$ cycloalkylalkyl, $C_1$-$C_6$ hydroxyalkyl, or $C_1$-$C_6$ alkoxyalkyl;

$R^5$ is hydrogen, $C_1$-$C_6$ alkyl, $C_3$-$C_8$ cycloalkyl, $C_3$-$C_8$ cycloalkyl-$C_1$-$C_6$-alkyl-, $C_1$-$C_6$ hydroxyalkyl, $C_1$-$C_6$ alkoxy-$C_1$-$C_6$-alkyl, or —$OR^{5b}$;

$R^{5a}$ is hydrogen or $C_1$-$C_6$ alkyl;

$R^{5b}$ is hydrogen, $C_1$-$C_6$ alkyl, $C_3$-$C_8$ cycloalkyl, $C_3$-$C_8$ cycloalkyl-$C_1$-$C_6$-alkyl, $C_1$-$C_6$ hydroxyalkyl, or $C_1$-$C_6$ alkoxy-$C_1$-$C_6$-alkyl;

each $R^6$ is independently selected from the group consisting of carboxy, $C_1$-$C_6$-alkoxycarbonyl, $C_1$-$C_6$-alkyl, $C_1$-$C_6$-haloalkyl, $C_1$-$C_6$-alkoxy-$C_1$-$C_6$-alkyl, $C_3$-$C_8$ cycloalkyl, heterocycloalkyl, —OC(O)$R^7$, —OS(O)$_2R^7$, —O—$C_1$-$C_6$-haloalkyl, $C_3$-$C_8$ cycloalkyloxy, heterocycloalkyloxy, aryloxy, heteroaryloxy, amino, $C_1$-$C_6$-alkylamino, di-$C_1$-$C_6$-alkylamino, —NR$^{8a}$S(O)$_2R^8$, —NR$^{8a}$C(O)$R^8$, —S(O)$_2R^8$, —S(O)$_2$NR$^{8a}R^8$, —C(O)$R^8$, —C(O)NR$^{8a}R^8$, and —$C_1$-$C_6$-alkylene-$R^{63}$;

each $R^{6a}$ is independently selected from the group consisting of $C_3$-$C_8$ cycloalkyl, heterocycloalkyl, —NH$_2$, —NH($C_1$-$C_6$-alkyl), —N($C_1$-$C_6$-alkyl)$_2$, —NR$^{9a}$S(O)$_2R^9$, —NR$^{9a}$C(O)$R^9$, —S(O)$_2R^9$, —S(O)$_2$NR$^{9a}R^9$, —C(O)$R^9$, and —C(O)NR$^{9a}R^9$;

each $R^7$ is independently selected from the group consisting of amino, $C_1$-$C_6$-alkylamino, di-$C_1$-$C_6$-alkylamino, $C_1$-$C_6$ alkyl, $C_3$-$C_8$ cycloalkyl, $C_1$-$C_6$-alkoxy, heterocycloalkyl, aryl, and heteroaryl;

each $R^{8a}$ and $R^{9a}$ is independently H or $C_{1-6}$ alkyl;

each $R^8$ and $R^9$ is independently $C_1$-$C_6$ alkyl, aryl, heteroaryl, $C_3$-$C_8$ cycloalkyl, or heterocycloalkyl; and each $R^{10}$ is independently hydrogen, halo, hydroxy, oxo, $C_1$-$C_6$ alkyl, $C_1$-$C_6$-hydroxyalkyl, halo-$C_1$-$C_6$-alkyl, amino-$C_1$-$C_6$-alkyl, $C_1$-$C_6$-alkylamino-$C_1$-$C_6$-alkyl, di-$C_1$-$C_6$-alkylamino-$C_1$-$C_6$-alkyl, $C_1$-$C_6$-alkoxy, $C_3$-$C_8$ cycloalkyl, heterocycloalkyl, or heteroaryl;

or an N-oxide, a stereoisomer, mixture of stereoisomers, and/or a pharmaceutically acceptable salt thereof.

In another aspect, provided herein are pharmaceutical compositions, single unit dosage forms, and kits suitable for use in treating a MEK-inhibitor responsive disorder or disease, MEK-inhibitor responsive dermal disorder or disease, MEK-mediated disorder or disease, or a MEK-mediated dermal disorder or disease which comprise a therapeutically or prophylactically effective amount of a compound provided herein, e.g., of some or any of the embodiments, of Formula (IA), Formula (I), Formula (I-P), Formula (Ia)-(Iu), or Formula (II), as described herein, and the claims, and compounds in Embodiment A.

In an aspect, a method of treatment of MEK-inhibitor responsive disorder or disease, MEK-inhibitor responsive dermal disorder or disease, MEK-mediated disorder or disease, or a MEK-mediated dermal disorder or disease is provided comprising administering to an individual in need thereof a therapeutically or prophylactically effective amount of a compound described herein, e.g., of some or any of the embodiments, of Formula (IA), Formula (I), Formula (I-P), Formula (Ia)-(Iu), or Formula (II), as described herein and the claims, and compounds in Embodiment A.

BRIEF DESCRIPTION OF THE DRAWINGS

FIG. 1. shows suppression of p-ERK in human cutaneous neurofibroma explants after treatment with Compound of Example 8 in a topical gel formulation (1%).

FIG. 2. shows suppression of p-ERK in human cutaneous neurofibroma explants after treatment with Compound of Example 8 in a Topical Gel Formulation (1%).

DESCRIPTION OF EXEMPLARY EMBODIMENTS

Provided herein are compounds, pharmaceutical compositions comprising the compounds, and methods of using the compounds and compositions in the treatment of a MEK-inhibitor responsive disorder or disease, MEK-inhibitor responsive dermal disorder or disease, MEK-mediated disorder or disease, or a MEK-mediated dermal disorder or disease. Also provided herein are methods of treating a MEK-inhibitor responsive disorder or disease, MEK-inhibitor responsive dermal disorder or disease, MEK-mediated disorder or disease, or a MEK-mediated dermal disorder or disease in a mammal comprising administering a therapeutically or prophylactically effective amount of a compound or composition to a mammal. In an embodiment, the mammal is a human.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being substituted, the groups in the list of substituents are themselves unsubstituted. For example, a substituted alkyl group can be substituted, for example, with a cycloalkyl group, and the cycloalkyl group is not further substituted unless specified otherwise.

"Alkenyl," as used herein, unless otherwise specified, means a straight or branched hydrocarbon radical having at least one double bond. In certain embodiments, the alkenyl group includes two to ten carbon atoms, i.e., $C_2$ to $C_{10}$ alkenyl. In certain embodiments, the alkenyl is a $C_{2-6}$alkenyl. In some embodiments, alkenyl is ethenyl, propenyl, 1-but-3-enyl, 1-pent-3-enyl, or 1-hex-5-enyl.

"Alkynyl" means a straight or branched hydrocarbon radical having at least one triple bond. In certain embodiments, the alkynyl group includes two to ten carbon atoms, i.e., $C_2$ to $C_{10}$ alkyl. In certain embodiments, the alkynyl is a $C_{2-6}$alkyl. In some embodiments, alkynyl is ethynyl, propynyl, butynyl, pentyn-2-yl and the like.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl is a $C_{1-6}$alkyl. In certain embodiments, the alkyl group is selected from the group consisting of methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl.

The term "alkoxy," as used herein, and unless otherwise specified, refers to the group —OR' where R' is alkyl. Alkoxy groups include, in certain embodiments, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkoxyalkyl," as used herein, and unless otherwise specified, refers to an alkyl group substituted with 1, 2, 3, or 4 alkoxy groups, as defined herein. In certain embodiments, the alkoxyalkyl is a alkoxy-$C_{1-6}$alkyl. In certain embodiments, the alkoxyalkyl is a $C_{1-6}$alkyl substituted with one, two, or three alkoxy, in some embodiments with one or two alkoxy, in some embodiments with one alkoxy.

The term "alkoxycarbonyl," as used herein, and unless otherwise specified, refers to a
—C(O)R group where R is alkoxy, as defined herein.

The term "alkylamino," as used herein, and unless otherwise specified, means a —NHR radical where R is alkyl as defined herein, or an N-oxide derivative thereof. In some embodiments, alkylamino is methylamino, ethylamino, n-, iso-propylamino, n-, iso-, tert-butylamino, or methylamino-N-oxide, and the like.

The term "alkylthio," as used herein, and unless otherwise specified, refers to the group —SR' where R' is $C_{1-10}$alkyl. In some embodiments, alkylthio is $C_{1-6}$alkylthio. In some embodiments, alkylthio is methylthio.

The term "amino," as used herein, and unless otherwise specified, means a —$NH_2$.

The term "aryl," as used herein, and unless otherwise specified, means a monovalent six- to fourteen-membered, mono- or bi-carbocyclic ring, wherein the monocyclic ring is aromatic and at least one of the rings in the bicyclic ring is aromatic. In some embodiments, aryl is phenyl, naphthyl, or indanyl.

The term "aminoalkyl," as used herein, unless otherwise specified, refers to an alkyl group substituted with one or two $NH_2$.

The term "alkylaminoalkyl," as used herein, unless otherwise specified, refers to an alkyl group substituted with one or two —NH(alkyl) groups.

The term "dialkylaminoalkyl," as used herein, unless otherwise specified, refers to an alkyl group substituted with one or two —N(alkyl)$_2$ groups.

The term "aryloxy," as used herein, unless otherwise specified, refers to a —OR group where R is aryl as defined herein.

The term "cycloalkyl," as used herein, unless otherwise specified, refers to a monovalent, saturated or partially unsaturated (but not aromatic) mono or multi-cyclic hydrocarbon. In certain embodiments, the cycloalkyl group may be a bridged or non-bridged, spirocyclic or not spirocyclic, and/or fused or not fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), from 3 to 8 ($C_{3-8}$), or from 3 to 7 ($C_{3-7}$) carbon atoms. In certain embodiments, the cycloalkyl group is monocyclic or bicyclic. In certain embodiments, the cycloalkyl group is monocyclic. In certain embodiments, the cycloalkyl group is bicyclic. In certain embodiments, the cycloalkyl group is tricyclic. In certain embodiments, the cycloalkyl group is fully saturated. In certain embodiments, the cycloalkyl group is partially unsaturated. In certain embodiments, the cycloalkyl group is cyclopropyl, cyclobutyl, cyclopentyl, cyclohexyl, cycloheptyl, bicyclo[2.1.1]hexyl, bicyclo[2.2.1]heptyl, decalinyl or adamantyl.

The term "cycloalkylalkyl," as used herein, unless otherwise specified, refers to an alkyl group, as defined herein (in one embodiment, $C_1$-$C_6$), substituted with one or two cycloalkyl groups as defined herein.

The term "cycloalkyloxy," as used herein, unless otherwise specified, refers to a —OR group where R is cycloalkyl as defined herein.

The term "dialkylamino," as used herein, and unless otherwise specified, means an —NRR' radical where R and R' are independently alkyl as defined herein, and an N-oxide thereof. In some embodiments, dialkylamino is dimethylamino, diethylamino, N,N-methylpropylamino or N,N'-methylethylamino, and the like.

The term "haloalkyl," as used herein, and unless otherwise specified, refers to an alkyl group substituted with 1, 2, 3, 4, or 5 halo groups. In certain embodiments, the haloalkyl is a halo-$C_{1-6}$alkyl.

The terms "halogen" and "halo," as used herein, and unless otherwise specified, are synonymous and refer to chloro, bromo, fluoro or iodo.

The term "heteroaryloxy," as used herein, unless otherwise specified, refers to a —OR group where R is heteroaryl as defined herein.

The term "heterocyclic," as used herein, and unless otherwise specified, refers to a monovalent monocyclic non-aromatic ring system and/or a multi cyclic ring system that contains at least one non-aromatic ring; wherein one or more (in certain embodiments, 1, 2, 3, or 4) of the non-aromatic monocyclic ring atoms is a heteroatom independently selected from O, S(O)$_{0-2}$, and N, and the remaining ring atoms are carbon atoms; and wherein one or more (in certain embodiments, 1, 2, 3, or 4) of any of the ring atoms in the multicyclic ring system is a heteroatom(s) independently selected from O, S(O)$_{0-2}$, and N, and the remaining ring atoms are carbon. In certain embodiments, the heterocyclic ring comprises one or two heteroatom(s) which are nitrogen. In certain embodiments, heterocyclic is multicyclic and comprises one heteroatom in a non-aromatic ring, or comprises one heteroatom in an aromatic ring, or comprises two heteroatoms in an aromatic ring, or comprises two heteroatoms where one is in an aromatic ring and the other is in a non-aromatic ring. In certain embodiments, the heterocyclic group has from 3 to 20, 3 to 15, 3 to 10, 3 to 8, 4 to 7, or 5 to 6 ring atoms. In certain embodiments, the heterocyclic is a monocyclic, bicyclic, tricyclic, or tetracyclic ring system. In certain embodiments, the heterocyclic group may be a bridged or non-bridged, spirocyclic or not spirocyclic, and/or fused or not fused bicyclic group. One or more of the nitrogen and sulfur atoms may be optionally oxidized, one or more of the nitrogen atoms may be optionally quaternized, one or more of the carbon atoms may be optionally replaced with

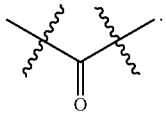 [SMILES: "." ; *C(*)=O]

Some rings may be partially or fully saturated, or aromatic provided that heterocyclic is not fully aromatic. The monocyclic and multicyclic heterocyclic rings may be attached to the main structure at any heteroatom or carbon atom which results in a stable compound. The multicyclic heterocyclic may be attached to the main structure through any of its rings, including any aromatic or nonaromatic ring, regardless of whether the ring contains a heteroatom. In certain embodiments, heterocyclic is "heterocycloalkyl" which is 1) a saturated or partially unsaturated (but not aromatic) monovalent monocyclic heterocyclic group which contains at least one ring heteroatom, as described herein, or 2) a saturated or partially unsaturated (but not aromatic) monovalent bi- or tri-cyclic heterocyclic group in which at least one ring contains at least one heteroatom as described herein. In certain embodiments, heterocyclic is "heteroaryl" which is an aromatic heterocyclic containing at least one ring heteroatom, as described herein. When heterocyclic, heteroaryl, and heterocycloalkyl are substituted, they can be substituted on any ring, i.e. on any aromatic or nonaromatic ring comprised by heterocyclic, heteroaryl, and heterocycloalkyl. In certain embodiments, such heterocyclic includes, but are not limited to, imidazolyl, thienyl, furyl, pyrazolyl, pyrrolyl, thiazolyl, oxazolyl, oxadiazolyl, pyridyl, pyrimidinyl, pyridazinyl, pyrazinyl, quinolinyl, azepinyl, benzodioxanyl, benzodioxolyl, benzofuranonyl, benzopyranonyl, benzopyranyl, dihydrobenzofuranyl, benzotetrahydrothienyl, benzothiopyranyl, benzoxazinyl, (3-carbolinyl, chromanyl, chromonyl, cinnolinyl, coumarinyl, decahydroquinolinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isochromanyl, isocoumarinyl, isoindolinyl, 1-oxo-isoindolinyl, 1,3-dioxo-isoindolinyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxo-hexahydroisoindolyl, oxazolidinonyl, oxazolidinyl, oxiranyl, piperazinyl, 2,6-dioxo-piperazinyl, piperidinyl, 2,6-dioxo-piperidinyl, 4-piperidonyl, pyrazolidinyl, pyrazolinyl, pyrrolidinyl, pyrrolinyl, 2-oxopyrrolidinyl, 2,5-dioxopyrrolidinyl, quinuclidinyl, tetrahydrofuryl, tetrahydroisoquinolinyl, tetrahydropyranyl, tetrahydrothienyl, thiamorpholinyl, thiomorpholinyl, 3,5-dioxo-thiomorpholinyl, thiazolidinyl, 2,4-dioxo-thiazolidinyl, tetrahydroquinolinyl, phenothiazinyl, phenoxazinyl, xanthenyl, and 1,3,5-trithianyl. In some or any embodiments, heterocyclic is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl.

The term "heteroaryloxy," as used herein, unless otherwise specified, refers to a —OR group where R is heterocycloalkyl as defined herein.

The term "heterocycloalkyloxy," as used herein, unless otherwise specified, refers to a
—OR group where R is heterocycloalkyl as defined herein.

The term "hydroxyalkyl," as used herein, and unless otherwise specified, refers to an alkyl group substituted with 1, 2, 3, or 4 hydroxy groups. In certain embodiments, the hydroxyalkyl is a hydroxy-$C_{1-6}$alkyl. In certain embodiments, the hydroxyalkyl is a $C_{1-6}$alkyl substituted with one, two, or three hydroxy, in some embodiments with one or two hydroxy, in some embodiments with one hydroxy.

The term "phenoxy," as used herein refers to an —OR group where R is phenyl as defined herein. The phenyl is optionally substituted as described herein.

The term "protecting group," as used herein, and unless otherwise specified, refers to a group that is added to an oxygen, nitrogen or phosphorus atom to prevent its further reaction or for other purposes. A wide variety of oxygen and nitrogen protecting groups are known to those skilled in the art of organic synthesis. (See for example those described in Greene, et al., Protective Groups in Organic Synthesis, John Wiley and Sons, Fourth Edition, 2006, hereby incorporated by reference.) In some embodiments, a nitrogen-protecting group (e.g. for $PG^1$ and $PG^2$) is 9-fluorenylmethyloxycarbonyl (Fmoc), tert-butoxy carbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl). In some embodiments, an oxygen-protecting group (e.g. for $X^1$) is methoxymethyl (MOM), ethoxyethyl, methoxyethoxymethyl, tetrahydrofuranyl, tetrahydropyranyl, methyl, tert-butyl, allyl, benzyl, trimethylsilyl, triethylsilyl, triisopropylsilyl, tert-butyldimethylsilyl, tert-butyldiphenylsilyl, acetyl, pivalyl, benzoyl, dimethoxytrityl, trityl, methoxytrityl, p-methoxybenzyl, or methylthiomethyl.

The term "pharmaceutically acceptable salt," as used herein, and unless otherwise specified, refers to any salt of a compound provided herein which retains its biological properties and which is not toxic or otherwise desirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; and (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, TV-methylglucamine piperazine, tris(hydroxymethyl)-aminomethane, tetramethylammonium hydroxide, and the like.

Pharmaceutically acceptable salts further include, in certain embodiments, and without limitation, sodium, potassium, calcium, magnesium, ammonium, tetraalkylammonium salts and the like. When the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "substantially free of" or "substantially in the absence of" stereoisomers with respect to a composition refers to a composition that includes at least 85 or 90% by weight, in certain embodiments 95%, 98%, 99% or 100% by weight, of a designated stereoisomer of a compound in the composition. In certain embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein or a salt thereof, that further includes a stoichiometric or non-stoichiometric amount of solvent bound by non-covalent intermolecular forces. Where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In certain embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkoxy," "heterocycloalkyl," "heterocyclic," and "heteroaryl," groups optionally comprise deuterium at one or more positions where hydrogen atoms are present, and wherein the deuterium composition of the atom or atoms is other than the natural isotopic composition.

Also as used herein, "alkyl," "cycloalkyl," "alkoxy," "heterocycloalkyl," "heterocyclic," and "heteroaryl," groups optionally comprise carbon-13 at an amount other than the natural isotopic composition.

As used herein, and unless otherwise specified, the term "$IC_{50}$" refers to an amount, concentration or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including anon-primate (e.g., a cow, pig, horse, cat, dog, rat, and mouse) and a primate (e.g., a monkey such as a cynomolgous monkey, a chimpanzee and a human), and in certain embodiments, a human. In certain embodiments, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a condition, is sufficient to effect such treatment for the condition. A "therapeutically effective amount" can vary depending on, inter alia, the compound, the disease or disorder and its severity, the size of the lesion to be treated, and the age, weight, etc., of the subject to be treated.

"Treating" or "treatment" of any disease or disorder refers, in certain embodiments, to ameliorating a disease or disorder that exists in a subject, including prophylactically. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder. In yet another embodiment, "treating" or "treatment" includes the reduction or elimination of either the disease or disorder (e.g. MEK-inhibitor responsive disorder or disease, MEK-inhibitor responsive dermal disorder or disease, MEK-mediated disorder or disease, or a MEK-mediated dermal disorder or disease) or one or more symptoms (e.g. MEK-inhibitor responsive disorder or disease, MEK-inhibitor responsive dermal disorder or disease, MEK-mediated disorder or disease, or a MEK-mediated dermal disorder or disease) of the disease or disorder, or to retard the progression of the disease or disorder (e.g. MEK-inhibitor responsive disorder or disease, MEK-inhibitor responsive dermal disorder or disease, MEK-mediated disorder or disease, or a MEK-mediated dermal disorder or disease) or of one or more symptoms (e.g. MEK-inhibitor responsive disorder or disease, MEK-inhibitor responsive dermal disorder, MEK-mediated disorder or disease, or disease or a MEK-mediated dermal disorder or disease) of the disease or disorder, or to reduce the severity of the disease or disorder (e.g. MEK-inhibitor responsive disorder or disease, MEK-inhibitor responsive dermal disorder, MEK-mediated disorder or disease, or disease or a MEK-mediated dermal disorder or disease) or of one or more symptoms (e.g. MEK-inhibitor responsive disorder or disease, MEK-inhibitor responsive dermal disorder, MEK-mediated disorder or disease, or disease or a MEK-mediated dermal disorder or disease) of the disease or disorder. In yet another embodiment, "treating" or "treatment" includes administering a compound described herein prophylactically.

"Topical" means application of a suitable compound (e.g. active agent) or composition comprising a compound (e.g. active agent) to the skin to treat or prevent a disease or a lesion of the skin. "Transdermal" means application of a suitable compound (e.g. active agent) or composition comprising a compound (e.g. active agent) to the skin such that the active agent may penetrate the layers in the skin to reach beyond the dermal or hypodermal layers, including, for example, systemic delivery. "Subcutaneous" means application of a suitable compound (e.g. active agent) or composition comprising a compound (e.g. active agent) to the layers below the epidermis and dermis. "Intradermal" means application of a suitable compound (e.g. active agent) or composition comprising a compound (e.g. active agent) in the dermal or hypodermal layers. "Intralesional" means injection of a suitable compound (e.g. active agent) or composition comprising a compound (e.g. active agent) at the site of the lesion.

In some embodiments, "topical" means application of a suitable compound (e.g. active agent) or composition comprising a compound (e.g. active agent) to the skin with adequate penetration of the epidermis or dermis to treat or prevent a lesion or a disease of the epidermis and/or dermis. In some embodiments of topical application, the compound or composition penetrates the epidermis or dermis without significant systemic exposure nor intent to treat or prevent a disease of another organ system. In some embodiments, "transdermal" means application of a suitable compound (e.g. active agent) or composition comprising a compound (e.g. active agent) to the skin with the objective of obtaining systemic therapeutic levels. In some embodiments of transdermal application, the active agent will penetrate the layers in the skin to reach beyond the dermal or hypodermal layers, including, for example, systemic delivery. In some embodiments, "subcutaneous" means injection of a suitable compound (e.g. active agent) or composition comprising a compound (e.g. active agent) into the layers below the epidermis and dermis. In some embodiments, "intradermal" means injection of a compound (e.g. active agent) or composition comprising a compound (e.g. active agent) into the dermal layers with the objective of obtaining systemic therapeutic levels. In some embodiments, "intralesional" means injection of a compound (e.g. active agent) or composition comprising a compound (e.g. active agent) directly into a lesion, such as a tumor or diseased tissue, with the objective of treating or preventing a disease or a lesion.

Distinctiveness and Advantages of the Compounds of the Present Application

The compounds of the present application are designed to be used in a different and unexpected way compared to compounds in the MEK art. The historical focus of MEK inhibitor discovery and development has been to make orally bioavailable compounds with sufficient in vivo stability to inhibit the MEK1 enzyme in tumors using an acceptable oral dosing regimen, thus favoring the selection of compounds with metabolic stability.

Consistent with the goal in the art to provide stable MEK compounds, the development of CI-1040, a MEK inhibitor formerly in clinical trials, was terminated in part due to its unfavorable stability. A compound of much greater metabolic stability, PD-0325901, was chosen for further development. A published account of this states "CI-1040 suffered however from poor exposure due to its poor solubility and rapid clearance, and as a result, development of the compound was terminated." (Barret el al., *Bioorganic & Medicinal Chemistry Letters* 2008, 18, 6501-6504). Other literature accounts of MEK inhibitor discovery demonstrate that optimization of metabolic stability was a goal of identifying compounds for clinical use. Finally, the FDA-approved trametinib is significantly stable to metabolism leading to a remarkable half-life in humans of 3.9 to 4.8 days (see Infante et al. *The Lancet* 2012, *Vol* 13(8), 773-78; also drug label, available at accessdata.fda.gov/drugsatfda_docs/label/2013/204114s0001b1.pdf).

It is clear, from the above accounts of MEK inhibitor discovery and development, that high systemic clearance, as measured by microsomal stability (or some other assay routinely used in the art) or rodent in vivo pharmacokinetic experiments, has been an undesired characteristic leading to the discontinuation of certain compounds and the further optimization of such compounds to provide for enhanced metabolic stability. In contrast, Applicant provides compounds which are designed to have significant metabolic lability.

Table 1 below provides half-life in human liver S9 fractions for a number of compounds in the MEK art, as well as a compound of the present application. The data in Table 1 were generated at the Applicant's request using the assay in Biological Example 3 using human liver S9 fraction. As evident from the data, the half-life in human liver S9 fractions varies considerably across the compounds.

TABLE 1

| Compound | Liver S9 $t_{1/2}$ (min) | CLint (μL/min/mg protein) |
|---|---|---|
| CI-1040 | 33 | 10.37 |

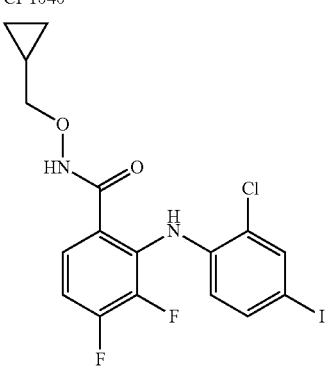

TABLE 1-continued

| Compound | Liver S9 $t_{1/2}$ (min) | CLint (μL/min/mg protein) |
|---|---|---|
| PD-0325901 | 340 | 1.02 |
| Binemetinib | 277 | 1.25 |
| Selumetinib | 138 | 2.50 |
| GDC-0623 | 50 | 6.98 |

TABLE 1-continued

| Compound | Liver S9 t₁/₂ (min) | CLint (μL/min/mg protein) |
|---|---|---|
| Trametinib | 402 | 0.86 |
| Pimasertib | 268 | 1.29 |
| Compound C8 | 66 | 5.27 |
| Compound C9 | 158 | 2.20 |

TABLE 1-continued

| Compound | Liver S9 $t_{1/2}$ (min) | CLint (µL/min/mg protein) |
|---|---|---|
| A compound of the present application [structure: 2-((2-fluoro-4-iodophenyl)amino)-N-(2-hydroxyethoxy)thieno[2,3-b]pyridine-3-carboxamide] | 26 | 13.35 |
| A compound of the present application [structure: 5-fluoro-2-((2-fluoro-4-iodophenyl)amino)-N-(2-hydroxyethoxy)thieno[2,3-b]pyridine-3-carboxamide] | 6 | 57.15 |

In sharp contrast to the art compounds, the compounds of the present application are designed for topical, subcutaneous, intradermal, or intralesional application, resulting in inhibition of MEK activity in the dermal and epidermal layers (or in the lesion) for treatment of certain dermal disorders. After acting to treat the skin or lesion, in some embodiments, the compound is designed to be metabolically labile in order to limit systemic toxicity after topical, subcutaneous, transdermal, intradermal, or intralesional application by limiting the amount of time the compound remains in the peripheral circulation. The present application provides a solution for the treatment of dermal disorders with compounds which demonstrate the ability to penetrate the skin and suppress phospho-ERK.

In some embodiments, "soft MEK inhibitor" is a compound which inhibits MEK1 and/or 2 and is characterized by a predictable and controllable metabolism/degradation to non-toxic and biologically less active or inactive (i.e. does not inhibit, or inhibits to a lesser degree, MEK1 and/or 2) products after they have achieved their therapeutic role in the skin.

As used herein, "hard MEK inhibitor" refers to a MEK inhibitor known in the art. In an embodiment, a hard MEK inhibitor is designed for oral bioavailability. This is necessary to deliver therapeutically effective levels of MEK inhibitor to peripheral lesions with systemic delivery. In some embodiments, hard MEK inhibitors include, for example, PD0325901; PD184161; SMK-17; AS703026 (Pimasertib, MSC1936369); RO-4987655; Selumetinib (AZD6244, ARRY142886); Binimetinib (MEK162, ARRY-162, ARRY-438162); Refametinib; Cobimetinib (GDC-0973, XL518); GDC-0623; AZD8330 (ARRY-424704); trametinib; PD198306; and PD318088. In some embodiments, hard MEK inhibitors include, for example, PD0325901; AS703026 (Pimasertib, MSC1936369); Selumetinib (AZD6244, ARRY142886); Binimetinib (MEK162, ARRY-162, ARRY-438162); and trametinib.

While not wishing to be bound by theory, it is believed that soft MEK inhibitors, e.g., such as the "soft" MEK inhibitors described herein, are more metabolically labile than known "hard" MEK inhibitors. Due to their inherent metabolic instability, e.g., for degradation upon reaching the systemic circulation, "soft" MEK inhibitors, e.g., such as the "soft" MEK inhibitors described herein, are dermally active but have low systemic exposure upon local or non-systemic administration, e.g., topical, subcutaneous, transdermal, intradermal, or intralesional administration, because they may more rapidly degrade upon exposure to plasma or blood or hepatic metabolic enzymes. Unlike "soft" MEK inhibitors, known MEK inhibitors have been historically designed for good oral bioavailability, which requires good stability in plasma or blood and good stability to hepatic metabolism necessary to permit systemic delivery at therapeutically effective levels, and may be more prone to one or more unwanted side effects and increased toxicity. As a result, "soft" MEK inhibitors, e.g., such as the soft MEK inhibitors described herein, may be less systemically toxic.

In some embodiments, a soft Mek inhibitor has a half-life of less than or equal to about 90 minutes, less than or equal to about 75 minutes, less than or equal to about 60 minutes, less than or equal to about 55 minutes, less than or equal to about 50 minutes, less than or equal to about 45 minutes, less than or equal to about 40 minutes, less than or equal to about 35 minutes, less than or equal to about 30 minutes, less than or equal to about 25 minutes, less than or equal to about 20 minutes, less than or equal to about 15 minutes, or less than or equal to about 10 minutes. In some embodiments, a hard Mek inhibitor has a half-life of greater than or equal to about 90 minutes, greater than or equal to about 105 minutes, greater than or equal to about 2 hours, greater than or equal to about 2.5 hours, greater than or equal to about 3 hours, greater than or equal to about 5 hours, greater than or equal to about 8 hours, greater than or equal to about 10 hours, greater than or equal to about 16 hours, greater than or equal to about 24 hours, greater than or equal to about 36 hours, or greater than or equal to about 48 hours. In some embodiments, the hepatic metabolic half-life is measured using an assay such as substantially as described in Biological Example 3 or 4. In some embodiments, the hepatic metabolic half-life is measured using an assay such as substantially as described in Biological Example 3 using human liver S9 fraction.

In some or any embodiments, the term "dermal neurofibroma" is used interchangeably with "cutaneous neurofibroma." In some or any embodiments, the term "cutaneous neurofibroma" is an embodiment of "dermal neurofibroma."

The disclosure provides "soft" MEK inhibitors, compositions comprising "soft" MEK inhibitors, and methods of treating and/or preventing a dermal disorder (e.g., a MEK-inhibitor responsive dermal disorder or a MEK mediated dermal disorder, e.g., a dermal rasopathy, e.g., a dermal disorder associated with neurofibromatosis type 1 (NF1), e.g., a dermal neurofibroma, a cutaneous neurofibroma, a subdermal neurofibroma, or a superficial plexiform neurofibroma) with MEK inhibitors e.g., "soft" MEK inhibitors. For example, the methods described herein provide administration, e.g., local or non-systemic, e.g., topical, subcutaneous, transdermal, intradermal, or intralesional administration, of MEK inhibitors, e.g., "soft" MEK inhibitors, e.g., "soft" MEK inhibitors described herein, whereby one or more side effects exhibited with systemic exposure, e.g., one or more known side effects exhibited with MEK inhibitors designed for systemic delivery, are significantly reduced.

In an embodiment, administering comprises contacting the soft MEK inhibitor with the skin of the subject, e.g., an affected region of the skin, e.g., a region of the skin having a tumor associated with neurofibromatosis type 1 (NF1), e.g., a dermal neurofibroma, a cutaneous neurofibroma, or a superficial plexiform neurofibroma, e.g., by local or non-systemic application, e.g., topical, subcutaneous, transdermal, intradermal or intralesional application, of the soft MEK inhibitor.

In an embodiment, administering comprises contacting the soft MEK inhibitor with the skin, mucous membranes, vagina, penis, larynx, vulva, cervix, or anus of the subject, by local or non-systemic application, e.g., topical, subcutaneous, transdermal, intradermal, or intralesional application or application by suppository, of the soft MEK inhibitor.

In an embodiment, the tumor associated with neurofibromatosis type 1 (NF1), e.g., a dermal neurofibroma, a cutaneous neurofibroma, a subdermal neurofibroma, or a superficial plexiform neurofibroma, is reduced, e.g., the size or the total tumor volume is reduced, by at least about 15% relative to the reference standard (e.g., from about 15% to about 60%), thereby treating the subject. In an embodiment, the reference standard is the size or the total tumor volume in an untreated control, e.g., from the same subject or a different subject.

In an embodiment, the size or total tumor volume of the tumor associated with neurofibromatosis type 1 (NF1), e.g., a dermal neurofibroma, a cutaneous neurofibroma, a subdermal neurofibroma, or a superficial plexiform neurofibroma, is reduced by at least about 15%, by at least about 20%, by at least about 25%, by at least about 30%, by at least about 35%, by at least about 40%, by at least about 45%, by at least about 50%, by at least about 55%, by at least about 60% relative to the reference standard. In an embodiment, the reference standard is the size or the total tumor volume in an untreated control, e.g., from the same subject or a different subject.

In an embodiment, the method comprises evaluating the subject with magnetic resonance imaging (MRI), or optical imaging, or high frequency ultrasound, or silicone mold, or calipers, e.g., evaluating the volume of tumors obtained from the subject, e.g., prior to, during and/or after treatment.

The compound as administered has a first level of MEK inhibition. After metabolism/degradation, a residue of the administered compound has a lower level of MEK inhibition (e.g., of at least about 2-fold lower, at least about 3-fold lower, at least about 4-fold lower, at least about 5-fold lower, at least about 10-fold lower, at least about 15-fold lower, at least about 20-fold lower, at least about 30-fold lower, at least about 40-fold lower, at least about 50 fold lower, at least about 60-fold lower, at least about 70-fold lower, at least about 80-fold lower, at least about 90-fold lower, at least about 100-fold lower, at least about 200-fold lower, at least about 500 fold lower, at least about 1,000-fold lower level of MEK inhibition, as compared to the compound before it is metabolized/degraded).

In an embodiment, after metabolism/degradation any residue of a compound disclosed herein has a lower level of MEK inhibition, e.g., of about 2-fold lower, about 3-fold lower, about 4-fold lower, about 5-fold lower, about 10-fold lower, about 20-fold lower, about 50 fold lower, about 100-fold lower, about 200-fold lower, about 500 fold lower, about 1,000-fold lower level of MEK inhibition, as compared to the compound before it is metabolized/degraded.

In certain such embodiment, after metabolism/degradation any residue of a compound disclosed herein has a lower level of MEK inhibition, e.g., of about 5-fold lower, about 10-fold lower, about 20-fold lower, about 30-fold lower, about 40-fold lower, about 50 fold lower, about 100-fold lower, about 200-fold lower, about 500 fold lower, about 1,000-fold lower level of MEK inhibition, as compared to the compound before it is metabolized/degraded.

In an embodiment, the half-life of the MEK inhibitor may have a half-life after exiting the skin, e.g., after systemic exposure, of less than about 24 hours, less than about 18 hours, less than about 14 hours, less than about 10 hours, less than about 9 hours, less than about 8 hours, less than about 7 hours, less than about 6 hours, less than about 5 hours, less than about 4 hours, less than about 3 hours, less than about 2 hours, less than about 1 hour, less than about 30 minutes, less than about 20 minutes, less than about 10 minutes, less than about 5 minutes, or less than about 1 minute.

In an embodiment, the half-life of the MEK inhibitor may have a half-life after introduction in vitro, e.g., after exposure to blood, serum or plasma in vitro, of less than about 24 hours, less than about 18 hours, less than about 14 hours, less than about 10 hours, less than about 9 hours, less than about 8 hours, less than about 7 hours, less than about 6 hours, less than about 5 hours, less than about 4 hours, less than about 3 hours, less than about 2 hours, less than about 1 hour, less than about 30 minutes, less than about 20 minutes, less than about 10 minutes, less than about 5 minutes, or less than about 1 minute.

In some embodiments, the half-life of the MEK inhibitor has a half-life of less than or equal to about 90 minutes, less than or equal to about 75 minutes, less than or equal to about 60 minutes, less than or equal to about 55 minutes, less than or equal to about 50 minutes, less than or equal to about 45 minutes, less than or equal to about 40 minutes, less than or equal to about 35 minutes, less than or equal to about 30 minutes, less than or equal to about 25 minutes, less than or equal to about 20 minutes, less than or equal to about 15 minutes, or less than or equal to about 10 minutes. In some embodiments, half-life of the MEK inhibitor is measured using Biological Example 3 using human liver S9 fraction.

Compounds

Provided herein are compounds that can modulate the activity of diseases or disorders associated with MEK. The compounds can be formed as described herein and used for the treatment of diseases or disorders in need of inhibition of MEK. In certain embodiments, the disease or disorder is Neurofibromatosis type 1. In certain embodiments, the disease or disorder is selected from the group consisting of a dermal rasopathy, a neurofibromatosis type 1, a dermal neurofibroma, a cutaneous neurofibroma, a subdermal neurofibroma, a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

The embodiments described herein include the recited compounds as well as a pharmaceutically acceptable salt, hydrate, solvate, stereoisomer, tautomer, or mixture thereof.

In one aspect, provided is a Compound of Formula (I-P):

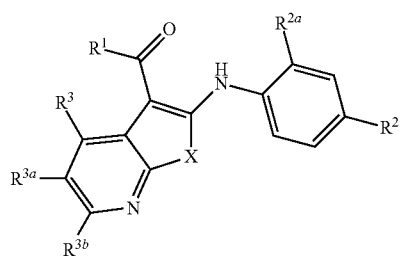

(I-P)

where $R^1$ is $-OR^4$, $-NR^5R^{5a}$, or an N-linked heterocycloalkyl where the N-linked heterocycloalkyl is optionally substituted with one or two $R^{10}$;

$R^{2a}$ is halo or $C_1$-$C_6$ alkyl;

$R^2$ is $-S-C_1$-$C_6$ alkyl, $C_1$-$C_6$ alkyl, $C_2$-$C_6$ alkenyl, $C_2$-$C_6$ alkynyl, or halo;

X is $-S-$ or $-O-$; and when X is $-S-$ and $R^3$, $R^{3a}$, and $R^{3b}$ are hydrogen, then $R^2$ is $C_2$-$C_6$ alkenyl, $C_2$-$C_6$ alkynyl, or $-S-C_1$-$C_6$ alkyl; and when X is $-S-$ and $R^3$, $R^{3a}$, and $R^{3b}$ are hydrogen, then $R^1$ is not an N-linked heterocycloalkyl optionally substituted with one or two $R^{10}$;

$R^3$, $R^{3a}$, and $R^{3b}$ are independently hydrogen, $C_1$-$C_6$ alkyl, $C_2$-$C_6$ alkenyl, $C_1$-$C_6$ alkynyl, $-S-C_1$-$C_6$ alkyl, halo, $C_1$-$C_6$-alkoxy; $C_1$-$C_6$-cycloalkyloxy; heterocycloalkyloxy; heteroaryloxy, or phenoxy where each phenyl and heteroaryl is independently optionally substituted with 1, 2, or 3 $R^6$;

$R^4$ is $C_1$-$C_6$ alkyl, $C_3$-$C_8$ cycloalkyl, $C_3$-$C_8$ cycloalkylalkyl, $C_1$-$C_6$ hydroxyalkyl, or $C_1$-$C_6$ alkoxy alkyl;

$R^5$ is hydrogen, $C_1$-$C_6$ alkyl, $C_3$-$C_8$ cycloalkyl, $C_3$-$C_8$ cycloalkyl-$C_1$-$C_6$-alkyl-, $C_1$-$C_6$ hydroxyalkyl, $C_1$-$C_6$ alkoxy-$C_1$-$C_6$-alkyl, or $-OR^{5b}$;

$R^{5a}$ is hydrogen or $C_1$-$C_6$ alkyl;

$R^{5b}$ is $C_1$-$C_6$ alkyl, $C_3$-$C_8$ cycloalkyl, $C_3$-$C_8$ cycloalkyl-$C_1$-$C_6$-alkyl, $C_1$-$C_6$ hydroxyalkyl, or $C_1$-$C_6$ alkoxy-$C_1$-$C_6$-alkyl;

each $R^6$ is independently selected from the group consisting of carboxy, $C_1$-$C_6$-alkoxycarbonyl, $C_1$-$C_6$-alkyl, $C_1$-$C_6$-haloalkyl. $C_1$-$C_6$-alkoxy-$C_1$-$C_6$-alkyl. $C_3$-$C_8$ cycloalkyl, heterocycloalkyl, $-OC(O)R^7$, $-OS(O)_2R^7$, $-O-C_1$-$C_6$-haloalkyl. $C_1$-$C_6$ cycloalkyloxy, heterocycloalkyloxy, aryloxy, heteroaryloxy, amino, $C_1$-$C_6$-alkylamino, di-$C_1$-$C_6$-alkylamino, $-NR^{8a}S(O)_2R^8$, $-NR^{8a}C(O)R^8$, $-S(O)_2R^8$, $-S(O)_2NR^{8a}R^8$, $-C(O)R^8$, $-C(O)NR^{8a}R^8$, and $-C_1$-$C_6$-alkylene-$R^{63}$;

each $R^{6a}$ is independently selected from the group consisting of $C_3$-$C_8$ cycloalkyl, heterocycloalkyl, $-NH_2$, $-NH(C_1$-$C_6$-alkyl), $-N(C_1$-$C_6$-alkyl)$_2$, $-NR^{9a}S(O)_2R^9$, $-NR^{9a}C(O)R^9$, $-S(O)_2R^9$, $-S(O)_2NR^{9a}R^9$, $-C(O)R^9$, and $-C(O)NR^{9a}R^9$;

each $R^7$ is independently selected from the group consisting of amino, $C_1$-$C_6$-alkylamino, di-$C_1$-$C_6$-alkylamino, $C_1$-$C_6$ alkyl, $C_3$-$C_8$ cycloalkyl, $C_1$-$C_6$-alkoxy, heterocycloalkyl, aryl, and heteroaryl;

each $R^{8a}$ and $R^{9a}$ is independently H or $C_{1-6}$ alkyl;

each $R^8$ and $R^9$ is independently $C_1$-$C_6$ alkyl, aryl, heteroaryl, $C_3$-$C_8$ cycloalkyl, or heterocycloalkyl; and each $R^{10}$ is independently hydrogen, halo, hydroxy, oxo, $C_1$-$C_6$ alkyl, $C_1$-$C_6$-hydroxyalkyl, halo-$C_1$-$C_6$-alkyl, amino-$C_1$-$C_6$-alkyl, $C_1$-$C_6$-alkylamino-$C_1$-$C_6$-alkyl, di-$C_1$-$C_6$-alkylamino-$C_1$-$C_6$-alkyl, $C_1$-$C_6$-alkoxy, $C_3$-$C_8$ cycloalkyl, heterocycloalkyl, or heteroaryl;

or an N-oxide, a stereoisomer, mixture of stereoisomers, and/or a pharmaceutically acceptable salt thereof.

In some or any embodiments, provided is a compound of Formula (IA), Formula (Ia), Formula (Ib), or Formula I-P, wherein when X is $-S-$ and $R^3$, $R^{3a}$, and $R^{3b}$ are hydrogen, then $R^1$ is not an N-linked heterocycloalkyl optionally substituted with one or two $R^{10}$; and all other groups are as defined herein in any aspect or embodiment described herein. In some or any embodiments, provided is a compound of Formula (IA), Formula (Ia), Formula (Ib), or Formula I-P, wherein $-OR^4$ or $-NR^5R^{5a}$; and all groups are as defined herein in any aspect or embodiment described herein.

In embodiment, provided herein is a compound of Formula (I)

(I)

where
R$^1$ is —OR$^4$ or —NR$^5$R$^{5a}$;
R$^{2a}$ is halo or C$_1$-C$_6$ alkyl;
R$^2$ is —S—C$_1$-C$_6$ alkyl, C$_1$-C$_6$ alkyl, C$_2$-C$_6$ alkenyl, C$_2$-C$_6$ alkynyl, or halo;
X is —S— or —O—; and when X is —S— and R$^3$, R$^{3a}$, and R$^{3b}$ are hydrogen, then R$^2$ is C$_2$-C$_6$ alkenyl, C$_2$-C$_6$ alkynyl, or —S—C$_1$-C$_6$ alkyl;
R$^3$, R$^{3a}$, and R$^{3b}$ are independently hydrogen, C$_1$-C$_6$ alkyl, C$_2$-C$_6$ alkenyl, C$_2$-C$_6$ alkynyl, —S—C$_1$-C$_6$ alkyl, halo, C$_1$-C$_6$ alkoxy; C$_3$-C$_8$-cycloalkyloxy; heterocycloalkyloxy; heteroaryloxy, or phenoxy where each phenyl and heteroaryl is independently optionally substituted with 1, 2, or 3 R$^6$;
R$^4$ is C$_1$-C$_6$ alkyl, C$_3$-C$_8$ cycloalkyl, C$_3$-C$_8$ cycloalkylalkyl, C$_1$-C$_6$ hydroxyalkyl, or C$_1$-C$_6$ alkoxy alkyl;
R$^5$ is hydrogen, C$_1$-C$_6$ alkyl, C$_3$-C$_8$ cycloalkyl, C$_3$-C$_8$ cycloalkyl-C$_1$-C$_6$-alkyl-, C$_1$-C$_6$ hydroxyalkyl, C$_1$-C$_6$ alkoxy-C$_1$-C$_6$-alkyl, or —OR$^{5b}$;
R$^{5a}$ is hydrogen or C$_1$-C$_6$ alkyl;
R$^{5b}$ is C$_1$-C$_6$ alkyl, C$_3$-C$_8$ cycloalkyl, C$_3$-C$_8$ cycloalkyl-C$_1$-C$_6$-alkyl, C$_1$-C$_6$ hydroxyalkyl, or C$_1$-C$_6$ alkoxy-C$_1$-C$_6$-alkyl;
each R$^6$ is independently selected from the group consisting of carboxy, C$_1$-C$_6$-alkoxycarbonyl, C$_1$-C$_6$-alkyl, C$_1$-C$_6$-haloalkyl, C$_1$-C$_6$-alkoxy-C$_1$-C$_6$-alkyl, C$_3$-C$_8$ cycloalkyl, heterocycloalkyl,
—OC(O)R$^7$, —OS(O)$_2$R$^7$, —O—C$_1$-C$_6$-haloalkyl, C$_3$-C$_8$ cycloalkyloxy, heterocycloalkyloxy, aryloxy, heteroaryloxy, amino, C$_1$-C$_6$-alkylamino, di-C$_1$-C$_6$-alkylamino, —NR$^{8a}$S(O)$_2$R$^8$, —NR$^{8a}$C(O)R$^8$, —S(O)$_2$R$^8$, —S(O)$_2$NR$^{8a}$R$^8$, —C(O)R$^8$, —C(O)NR$^{8a}$R$^8$, and —C$_1$-C$_6$-alkylene-R$^{6a}$;
each R$^{6a}$ is independently selected from the group consisting of C$_3$-C$_8$ cycloalkyl, heterocycloalkyl, —NH$_2$, —NH(C$_1$-C$_6$-alkyl), —N(C$_1$-C$_6$-alkyl)$_2$, —NR$^{9a}$S(O)$_2$R$^9$, —NR$^{9a}$C(O)R$^9$,
—S(O)$_2$R$^9$, —S(O)$_2$NR$^{9a}$R$^9$, —C(O)R$^9$, and —C(O)NR$^{9a}$R$^9$;
each R$^7$ is independently selected from the group consisting of amino, C$_1$-C$_6$-alkylamino, di-C$_1$-C$_6$-alkylamino, C$_1$-C$_6$ alkyl, C$_3$-C$_8$ cycloalkyl, C$_1$-C$_6$-alkoxy, heterocycloalkyl, aryl, and heteroaryl;
each R$^{8a}$ and R$^{9a}$ is independently H or C$_{1-6}$ alkyl; and
each R$^8$ and R$^9$ is independently C$_1$-C$_6$ alkyl, aryl, heteroaryl, C$_3$-C$_8$ cycloalkyl, or heterocycloalkyl;
or an N-oxide, a stereoisomer, mixture of stereoisomers, and/or a pharmaceutically acceptable salt thereof.

In some or any embodiments, provided is a Compound of Formula (Ia):

(Ia)

and all groups are as defined herein in any aspect or embodiment described herein, including of Formula (IA), Formula (I), Formula (I-P), and Formula (II).

In some or any embodiments, provided is a Compound of Formula (Ib):

(Ib)

and all groups are as defined herein in any aspect or embodiment described herein, including of Formula (IA), Formula (I), and Formula (I-P).

In some or any embodiments, provided is a Compound of Formula (IA), Formula (I), or Formula (I-P), where X is —O— or —S— and when X is —S— and R$^3$, R$^{3a}$, and R$^{3b}$ are hydrogen, then R$^2$ is C$_2$-C$_6$ alkenyl, C$_2$-C$_6$ alkynyl, or —S—C$_1$-C$_6$ alkyl; and all other groups are as defined herein in any aspect or embodiment described herein. In some or any embodiments, provided is a Compound of Formula (IA), Formula (I), or Formula (I-P), where X—O— or —S— and when X is —S—, then R$^3$, R$^{3a}$, and R$^{3b}$ are hydrogen, and R$^2$ is C$_2$-C$_6$ alkenyl, C$_2$-C$_6$ alkynyl, or —S—C$_1$-C$_6$ alkyl; and all other groups are as defined herein in any aspect or embodiment described herein. In some or any embodiments, provided is a Compound of Formula (IA), Formula (I), or Formula (I-P) where X is —O—, or —S— and when X is —S—, then R$^3$, R$^{3a}$, and R$^{3b}$ are hydrogen, and R$^2$ is C$_2$-C$_6$ alkynyl or —S—C$_1$-C$_6$ alkyl; and all other groups are as defined herein in any aspect or embodiment described herein. In some or any embodiments, provided is a Compound of Formula (IA), Formula (I), or Formula (I-P) where X is —O—, or —S— and when X is —S—, then R$^3$, R$^{3a}$, and R$^{3b}$ are hydrogen, and R$^2$ is C$_2$-C$_3$ alkynyl or —S—C$_1$-C$_3$ alkyl; and all other groups are as defined herein in any aspect or embodiment described herein. In some or any embodiments, provided is a Compound of Formula (IA), Formula (I), or Formula (I-P) where X is —O—, or —S— and when X is —S—, then R$^3$, R$^{3a}$, and R$^{3b}$ are hydrogen, and R$^2$ is C$_2$-C$_3$ alkynyl or —SCH$_3$; and all other groups are as defined herein in any aspect or embodiment described herein.

In some or any embodiments, provided is a Compound of Formula (IA), Formula (I), Formula (I-P), or Formula (Ia), where X is —S— and when $R^3$, $R^{3a}$, and $R^{3b}$ are hydrogen, then $R^2$ is $C_2$-$C_6$ alkenyl, $C_2$-$C_6$ alkynyl, or —S—$C_1$-$C_6$ alkyl; and all other groups are as defined herein in any aspect or embodiment described herein. In some or any embodiments, provided is a Compound of Formula (IA), Formula (I), Formula (I-P), or Formula (Ia) where X is —S—; $R^3$, $R^{3a}$, and $R^{3b}$ are hydrogen; and $R^2$ is $C_2$-$C_6$ alkenyl, $C_2$-$C_6$ alkynyl, or —S—$C_1$-$C_6$ alkyl; and all other groups are as defined herein in any aspect or embodiment described herein. In some or any embodiments, provided is a Compound of Formula (IA), Formula (I), Formula (I-P), or Formula (Ia) where X is —S—; $R^3$, $R^{3a}$, and $R^{3b}$ are hydrogen; and $R^2$ is $C_2$-$C_3$ alkenyl, $C_2$-$C_3$ alkynyl, or —S—$C_1$-$C_3$ alkyl; and all other groups are as defined herein in any aspect or embodiment described herein. In some or any embodiments, provided is a Compound of Formula (IA), Formula (I), Formula (I-P), or Formula (Ia) where X is —S—; $R^3$, $R^{3a}$, and $R^{3b}$ are hydrogen; and $R^2$ is $C_2$-$C_6$ alkynyl, or —S—$C_1$-$C_6$ alkyl; and all other groups are as defined herein in any aspect or embodiment described herein. In some or any embodiments, provided is a Compound of Formula (IA), Formula (I), Formula (I-P), or Formula (Ia) where X is —S—; $R^3$, $R^{3a}$, and $R^{3b}$ are hydrogen; and $R^2$ is $C_2$-$C_3$ alkynyl, or —S—$C_1$-$C_3$ alkyl; and all other groups are as defined herein in any aspect or embodiment described herein. In some or any embodiments, provided is a Compound of Formula (IA), Formula (I), Formula (I-P), or Formula (Ia) where X is —S—; $R^3$, $R^{3a}$, and $R^{3b}$ are hydrogen; and $R^2$ is $C_2$-$C_3$ alkenyl, $C_2$-$C_3$ alkynyl, or —$SCH_3$; and all other groups are as defined herein in any aspect or embodiment described herein. In some or any embodiments, provided is a Compound of Formula (IA), Formula (I), Formula (I-P), or Formula (Ia) where X is —S—; $R^3$, $R^{3a}$, and $R^{3b}$ are hydrogen; and $R^2$ is $C_2$-$C_3$ alkynyl or —$SCH_3$; and all other groups are as defined herein in any aspect or embodiment described herein. In some or any embodiments, provided is a Compound of Formula (IA), Formula (I), Formula (I-P), or Formula (Ia) where X is —S— and at least one of $R^3$, $R^{3a}$, and $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; and all other groups are as defined herein in any aspect or embodiment described herein. In some or any embodiments, provided is a Compound of Formula (IA), Formula (I), Formula (I-P), or Formula (Ia) where X is —S— and at least one of $R^3$, $R^{3a}$, and $R^{3b}$ is $C_1$-$C_6$ alkyl or $C_1$-$C_6$ alkoxy; and all other groups are as defined herein in any aspect or embodiment described herein. In some or any embodiments, provided is a Compound of Formula (IA), Formula (I), Formula (I-P), or Formula (Ia) where X is —S— and at least one of $R^3$, $R^{3a}$, and $R^{3b}$ is methyl or methoxy; and all other groups are as defined herein in any aspect or embodiment described herein. In some or any embodiments, provided is a Compound of Formula (IA), Formula (I), Formula (I-P), or Formula (Ia) where X is —S— and at least one of $R^3$, $R^{3a}$, and $R^{3b}$ is $C_1$-$C_6$ alkyl; and all other groups are as defined herein in any aspect or embodiment described herein. In some or any embodiments, provided is a Compound of Formula (IA), Formula (I), Formula (I-P), or Formula (Ia) where X is —S— and at least one of $R^3$, $R^{3a}$, and $R^{3b}$ is methyl; and all other groups are as defined herein in any aspect or embodiment described herein.

In some or any embodiments, provided is a Compound of Formula (IA), Formula (I), Formula (I-P), or Formula (Ib) where X is —O—; and all other groups are as defined herein in any aspect or embodiment described herein. In some or any embodiments, provided is a Compound of Formula (IA), Formula (I), Formula (I-P), or Formula (Ib) where X is —O— and at least one of $R^3$, $R^{3a}$, and $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; and all other groups are as defined herein in any aspect or embodiment described herein. In some or any embodiments, provided is a Compound of Formula (IA), Formula (I), Formula (I-P), or Formula (Ib) where X is —O— and at least one of $R^3$, $R^{3a}$, and $R^{3b}$ is $C_1$-$C_6$ alkyl or $C_1$-$C_6$ alkoxy; and all other groups are as defined herein in any aspect or embodiment described herein. In some or any embodiments, provided is a Compound of Formula (IA), Formula (I), Formula (I-P), or Formula (Ib) where X is —O— and at least one of $R^3$, $R^{3a}$, and $R^{3b}$ is methyl or methoxy; and all other groups are as defined herein in any aspect or embodiment described herein. In some or any embodiments, provided is a Compound of Formula (IA), Formula (I), Formula (I-P), or Formula (Ib) where X is —O— and at least one of $R^3$, $R^{3a}$, and $R^{3b}$ is $C_1$-$C_6$ alkyl; and all other groups are as defined herein in any aspect or embodiment described herein. In some or any embodiments, provided is a Compound of Formula (IA), Formula (I), Formula (I-P), or Formula (Ib) where X is —O— and at least one of $R^3$, $R^{3a}$, and $R^{3b}$ is methyl; and all other groups are as defined herein in any aspect or embodiment described herein.

In some or any embodiments, provided is a Compound of Formula (IA), Formula (I), Formula I-P, Formula (Ia), or Formula (Ib) where $R^2$ is —S—$C_1$-$C_3$ alkyl, $C_1$-$C_3$ alkyl, $C_2$-$C_4$ alkenyl, $C_2$-$C_3$ alkynyl, or halo; and all other groups are as defined herein in any aspect or embodiment described herein.

In some or any embodiments, provided is a Compound of Formula (IA), Formula (I), Formula I-P, Formula (Ia), or Formula (Ib) where $R^2$ is —S—$C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is —S—$C_1$-$C_3$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is —S—$CH_3$; and all other groups are as defined herein in any aspect or embodiment described herein.

In some or any embodiments, provided is a Compound of Formula (IA), Formula (I), Formula I-P, Formula (Ia), or Formula (Ib) where $R^2$ is $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is $C_1$-$C_3$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is $CH_3$; and all other groups are as defined herein in any aspect or embodiment described herein.

In some or any embodiments, provided is a Compound of Formula (IA), Formula (I), Formula I-P, Formula (Ia), or Formula (Ib) where $R^2$ is $C_2$-$C_6$ alkenyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is $C_2$-$C_4$ alkenyl; and all other groups are as defined herein in any aspect or embodiment described herein.

In some or any embodiments, provided is a Compound of Formula (IA), Formula (I), Formula I-P, Formula (Ia), or Formula (Ib) where $R^2$ is $C_2$-$C_6$ alkynyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is $C_2$-$C_3$ alkynyl; and all other groups are as defined herein in any aspect or embodiment described herein. In some or any embodiments, provided is a Compound of Formula (IA), Formula (I), Formula I-P, Formula (Ia), or Formula (Ib) where $R^2$ is $C_2$ alkynyl; and all other groups are as defined herein in any aspect or embodiment described herein.

In some or any embodiments, provided is a Compound of Formula (IA), Formula (I), Formula I-P, Formula (Ia), or Formula (Ib) where $R^2$ is halo; and all other groups are as defined herein in any aspect or embodiment described herein. In some or any embodiments, provided is a Compound of Formula (IA), Formula (I), Formula I-P, Formula (Ia), or Formula (Ib) where $R^2$ is fluoro; and all other groups are as defined herein in any aspect or embodiment described herein. In some or any embodiments, provided is a Compound of Formula (IA), Formula (I), Formula I-P, Formula (Ia), or Formula (Ib) where $R^2$ is iodo; and all other groups are as defined herein in any aspect or embodiment described herein. In some or any embodiments, provided is a Compound of Formula (IA), Formula (I), Formula I-P, Formula (Ia), or Formula (Ib) where $R^2$ is chloro; and all other groups are as defined herein in any aspect or embodiment described herein. In some or any embodiments, provided is a Compound of Formula (IA), Formula (I), Formula I-P, Formula (Ia), or Formula (Ib) where $R^2$ is bromo; and all other groups are as defined herein in any aspect or embodiment described herein.

In some or any embodiments, provided is a Compound of Formula (IA), Formula (I), Formula I-P, Formula (Ia), or Formula (Ib) where $R^{2a}$ is halo or $C_1$-$C_3$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo or $CH_3$; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is fluoro or $CH_3$; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is iodo or $CH_3$; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is chloro or $CH_3$; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is bromo or $CH_3$; and all other groups are as defined herein in any aspect or embodiment described herein.

In some or any embodiments, provided is a Compound of Formula (IA), Formula (I), Formula I-P, Formula (Ia), or Formula (Ib) where $R^{2a}$ is halo; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is fluoro; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is iodo; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is chloro; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is bromo; and all other groups are as defined herein in any aspect or embodiment described herein.

In some or any embodiments, provided is a Compound of Formula (IA), Formula (I), Formula I-P, Formula (Ia), or Formula (Ib) where $R^{2a}$ is $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is $C_1$-$C_3$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is $CH_3$; and all other groups are as defined herein in any aspect or embodiment described herein.

In some or any embodiments, provided is a Compound of Formula (IA), Formula (I), Formula I-P, Formula (Ia), or Formula (Ib) where $R^{2a}$ is $C_1$-$C_6$ alkyl and $R^2$ is halo; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is halo; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is $C_2$-$C_6$ alkynyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is —S—$C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is —$CH_3$ and $R^2$ is halo; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is halo; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is $C_2$-$C_3$ alkynyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is —S—$C_1$-$C_3$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^{2a}$ is halo and $R^2$ is —SCH$_3$; and all other groups are as defined herein in any aspect or embodiment described herein.

In some or any embodiments, provided is a Compound of Formula (IA), Formula (I), Formula I-P, Formula (Ia), or Formula (Ib) where $R^3$, $R^{3a}$, and $R^{3b}$ are hydrogen; and all other groups are as defined herein in any aspect or embodiment described herein. In some or any embodiments, provided is a Compound of Formula (IA), Formula (I), Formula I-P, Formula (Ia), or Formula (Ib) where at least one of $R^3$, $R^{3a}$, and $R^{3b}$ is $C_1$-$C_6$ alkyl or $C_1$-$C_6$ alkoxy; and all other groups are as defined herein in any aspect or embodiment described herein. In some or any embodiments, provided is a Compound of Formula (IA), Formula (I), Formula I-P, Formula (Ia), or Formula (Ib) where at least one of $R^3$, $R^{3a}$, and $R^{3b}$ is methyl or methoxy; and all other groups are as defined herein in any aspect or embodiment described herein. In some or any embodiments, provided is a Compound of Formula (IA), Formula (I), Formula I-P, Formula (Ia), or Formula (Ib) where at least one of $R^3$, $R^{3a}$, and $R^{3b}$ is $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where at least one of $R^3$, $R^{3a}$, and $R^{3b}$ is methyl; and all other groups are as defined herein in any aspect or embodiment described herein.

In some or any embodiments, provided is a Compound of Formula (IA), Formula (I), Formula I-P, Formula (Ia), or Formula (Ib) where one or two of $R^3$, $R^{3a}$, and $R^{3b}$ is hydrogen; and all other groups are as defined herein in any aspect or embodiment described herein. In some or any embodiments, provided is a Compound of Formula (IA), Formula (I), Formula I-P, Formula (Ia), or Formula (Ib) where two of $R^3$, $R^{3a}$, and $R^{3b}$ are hydrogen; and all other groups are as defined herein in any aspect or embodiment described herein. In some or any embodiments, provided is a Compound of Formula (IA), Formula (I), Formula I-P, Formula (Ia), or Formula (Ib) where one of $R^3$, $R^{3a}$, and $R^{3b}$ is $C_1$-$C_6$ alkyl or $C_1$-$C_6$ alkoxy and the others are hydrogen; and all other groups are as defined herein in any aspect or embodiment described herein. In some or any embodiments, provided is a Compound of Formula (IA), Formula (I), Formula I-P, Formula (Ia), or Formula (Ib) where one of $R^3$, $R^{3a}$, and $R^{3b}$ is methyl or methoxy and the others are hydrogen; and all other groups are as defined herein in any aspect or embodiment described herein.

In some or any embodiments, provided is a Compound of Formula (IA), Formula (I), Formula I-P, Formula (Ia), or Formula (Ib) where at least one of $R^3$, $R^{3a}$, and $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; and all other groups are as defined herein in any aspect or embodiment described herein. In some or any embodiments, provided is a Compound of Formula (IA), Formula (I), Formula I-P, Formula (Ia), or Formula (Ib) where $R^3$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; $R^{3a}$ and $R^{3b}$ are hydrogen; and all other groups are as defined herein in any aspect or embodiment described herein. In some or any embodiments, provided is a Compound of Formula (IA), Formula (I), Formula I-P, Formula (Ia), or Formula (Ib) where $R^{3a}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; $R^3$ and $R^{3b}$ are hydrogen; and all other groups are as defined herein in any aspect or embodiment described herein. In some or any embodiments, provided is a Compound of Formula (IA), Formula (I), Formula I-P, Formula (Ia), or Formula (Ib) where $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; $R^{3a}$ and $R^3$ are hydrogen; and all other groups are as defined herein in any aspect or embodiment described herein.

In some or any embodiments, provided is a Compound Formula (IA), Formula (I), Formula I-P, Formula (Ia), or Formula (Ib) where $R^3$, $R^{3a}$, and $R^{3b}$ are independently selected from hydrogen, halo, $C_1$-$C_6$ alkyl, $C_1$-$C_6$-alkoxy, $C_3$-$C_8$-cycloalkyloxy, heterocycloalkyloxy, heteroaryloxy where the heteroaryl is optionally substituted with 1, 2, or 3 $R^6$, and phenoxy where the phenyl is optionally substituted with 1, 2, or 3 $R^6$; and all other groups are as defined herein in any aspect or embodiment described herein. In some or any embodiments, provided is a Compound of Formula (IA), Formula (I), Formula I-P, Formula (Ia), or Formula (Ib) where $R^3$, $R^{3a}$, and $R^{3b}$ are independently selected from hydrogen, halo, and $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^3$, $R^{3a}$, and $R^{3b}$ are independently selected from $C_1$-$C_6$-alkoxy, $C_3$-$C_8$-cycloalkyloxy, heterocycloalkyloxy, heteroaryloxy where the heteroaryl is optionally substituted with 1, 2, or 3 $R^6$, and phenoxy where the phenyl is optionally substituted with 1, 2, or 3 $R^6$; and all other groups are as defined herein in any aspect or embodiment described herein.

In some or any embodiments, provided is a Compound of any one of Formula (IA), Formula (I), Formula I-P, Formula (Ia), or Formula (Ib) where $R^4$ and $R^5$ are $C_3$-$C_8$ cycloalkyl-$C_1$-$C_6$-alkyl; and all other groups are as defined herein in any aspect or embodiment described herein. In some or any embodiments, provided is a Compound of any one of Formula (IA), Formula (I), Formula I-P, Formula (Ia), or Formula (Ib) where $R^4$ and $R^5$ are $C_1$-$C_6$ hydroxyalkyl; and all other groups are as defined herein in any aspect or embodiment described herein. In some or any embodiments, provided is a Compound of any one of Formula (IA), Formula (I), Formula I-P, Formula (Ia), or Formula (Ib) where $R^4$ and $R^5$ are $C_1$-$C_6$ alkoxyalkyl; and all other groups are as defined herein in any aspect or embodiment described herein.

In some or any embodiments, provided is a Compound of Formula (IA), Formula (I), Formula I-P, Formula (Ia), or Formula (Ib) where $R^1$ is —OR$^4$ or —NR$^5$R$^{5a}$; and all other groups are as defined herein in any aspect or embodiment described herein. In some or any embodiments, provided is a Compound of Formula (IA), Formula (I), Formula I-P, Formula (Ia), or Formula (Ib) where $R^4$ and $R^5$ are $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^4$ and $R^5$ are $C_3$-$C_8$ cycloalkyl; and all other groups are as defined herein in any aspect or embodiment described herein. In some or any embodiments, provided is a Compound of Formula (IA), Formula (I), Formula I-P, Formula (Ia), or Formula (Ib) where $R^4$ and $R^5$ are $C_3$-$C_8$ cycloalkyl-$C_1$-$C_6$-alkyl; and all other groups are as defined herein in any aspect or embodiment described herein. In some or any embodiments, provided is a Compound of Formula (IA), Formula (I), Formula I-P, Formula (Ia), or Formula (Ib) where $R^4$ and $R^5$ are $C_1$-$C_6$ hydroxyalkyl; and all other groups are as defined herein in any aspect or embodiment described herein. In some or any embodiments, provided is a Compound of Formula (IA), Formula (I), Formula I-P, Formula (Ia), or Formula (Ib) where $R^4$ and $R^5$ are $C_1$-$C_6$ alkoxyalkyl; and all other groups are as defined herein in any aspect or embodiment described herein.

In some or any embodiments, provided is a Compound of Formula (IA), Formula (I), Formula I-P, Formula (Ia), or Formula (Ib) where $R^1$ is —$OR^4$; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$OR^4$ and $R^4$ is $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$OR^4$ and $R^4$ is $C_3$-$C_8$ cycloalkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$OR^4$ and $R^4$ is $C_3$-$C_8$ cycloalkyl-$C_1$-$C_6$-alkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$OR^4$ and $R^4$ is $C_1$-$C_6$ hydroxyalkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$OR^4$ and $R^4$ is $C_1$-$C_6$ alkoxyalkyl; and all other groups are as defined herein in any aspect or embodiment described herein.

In some or any embodiments, provided is a Compound of Formula (IA), Formula (I), Formula I-P, Formula (Ia), or Formula (Ib) where $R^1$ is —$NR^5R^{5a}$; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is hydrogen; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is $C_1$-$C_6$ alkyl substituted with one heterocycloalkyl (which is, in some embodiments, 2,2-dimethyl-1,3-dioxolan-4-yl); and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is $C_1$-$C_6$ alkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is $C_3$-$C_8$ cycloalkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is $C_3$-$C_8$ cycloalkyl-$C_1$-$C_6$-alkyl-; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is $C_1$-$C_6$ hydroxyalkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is $C_1$-$C_6$ alkoxy-$C_1$-$C_6$-alkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$ and $R^5$ is —$OR^{5b}$; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$, $R^5$ is —$OR^{5b}$, and $R^{5b}$ is $C_1$-$C_6$ alkyl; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^{5b}$, and $R^{5b}$ is hydrogen; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$, $R^5$ is —$OR^{5b}$, and $R^{5b}$ is $C_3$-$C_8$ cycloalkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$, $R^5$ is —$OR^{5b}$, and $R^{5b}$ is $C_3$-$C_8$ cycloalkyl-$C_1$-$C_6$-alkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$, $R^5$ is —$OR^{5b}$, and $R^{5b}$ is $C_1$-$C_6$ hydroxyalkyl; and all other groups are as defined herein in any aspect or embodiment described herein. In some or any embodiments, provided is a Compound of Formula (IA), Formula (I), Formula I-P, Formula (Ia), or Formula (Ib) where $R^1$ is —$NR^5R^{5a}$, $R^5$ is —$OR^{5b}$, and $R^{5b}$ is $C_1$-$C_6$ alkoxy-$C_1$-$C_6$-alkyl; and all other groups are as defined herein in any aspect or embodiment described herein.

In some or any embodiments, provided is a Compound of Formula (IA), Formula (I), Formula I-P, Formula (Ia), or Formula (Ib) where $R^{5a}$ is hydrogen; and all other groups are as defined herein in any aspect or embodiment described herein. In some or any embodiments, provided is a Compound of Formula (IA), Formula (I), Formula I-P, Formula (Ia), or Formula (Ib) where $R^{5a}$ is $C_1$-$C_6$ alkyl; and all other groups are as defined herein in any aspect or embodiment described herein.

In some or any embodiments, provided is a Compound of Formula (IA), Formula I-P, Formula (Ia), or Formula (Ib) where $R^1$ is an N-linked heterocycloalkyl where the N-linked heterocycloalkyl is optionally substituted with one or two $R^{10}$; and all other groups are as defined herein in any aspect or embodiment described herein. In some or any embodiments, provided is a Compound of Formula (IA), Formula I-P, Formula (Ia), or Formula (Ib), where $R^1$ is N-linked azetidinyl, N-linked pyrrolidinyl, N-linked piperidinyl, or N-linked morpholinyl where the N-linked heterocycloalkyl is optionally substituted with one or two $R^{10}$; and all other groups are as defined herein in any aspect or embodiment described herein. In some or any embodiments, provided is a Compound of Formula (IA), Formula I-P, Formula (Ia), or Formula (Ib), where $R^1$ is N-linked azetidinyl where the N-linked heterocycloalkyl is optionally substituted with one or two $R^{10}$; and all other groups are as defined herein in any aspect or embodiment described herein. In some or any embodiments, provided is a Compound of Formula (IA), Formula I-P, Formula (Ia), or Formula (Ib), where $R^1$ is N-linked pyrrolidinyl where the N-linked heterocycloalkyl is optionally substituted with one or two $R^{10}$; and all other groups are as defined herein in any aspect or embodiment described herein. In some or any embodiments, provided is a Compound of Formula (IA), Formula I-P, Formula (Ia), or Formula (Ib), where $R^1$ is N-linked piperidinyl where the N-linked heterocycloalkyl is optionally substituted with one or two $R^{10}$; and all other groups are as defined herein in any aspect or embodiment described herein. In some or any embodiments, provided is a Compound of Formula (IA), Formula I-P, Formula (Ia), or Formula (Ib), where $R^1$ is N-linked morpholinyl where the N-linked heterocycloalkyl is optionally substituted with one or two $R^{10}$; and all other groups are as defined herein in any aspect or embodiment described herein.

In some or any embodiments, provided is a Compound of Formula (IA), Formula I-P, Formula (Ia), or Formula (Ib), where one $R^6$ is —$NR^{8a}S(O)_2R^8$; and all other groups are as defined herein in any aspect or embodiment described herein. In some or any embodiments, provided is a Compound of Formula (IA), Formula I-P, Formula (Ia), or Formula (Ib), where one $R^6$ is —$NR^{8a}C(O)R^8$; and all other groups are as defined herein in any aspect or embodiment described herein. In some or any embodiments, provided is a Compound of Formula (IA), Formula I-P, Formula (Ia), or Formula (Ib), where one $R^6$ is amino; and all other groups are as defined herein in any aspect or embodiment described herein. In some or any embodiments, provided is a Compound of Formula (IA), Formula I-P, Formula (Ia), or Formula (Ib), where one $R^6$ is —$S(O)_2NR^{8a}R^8$; and all other groups are as defined herein in any aspect or embodiment described herein. In some or any embodiments, provided is a Compound of Formula (IA), Formula I-P, Formula (Ia), or Formula (Ib), where one $R^6$ is —$C(O)NR^{8a}R^8$; and all other groups are as defined herein in any aspect or embodiment described herein. In some or any embodiments, provided is a Compound of Formula (IA), Formula I-P, Formula (Ia), or Formula (Ib), where one $R^6$ is carboxy; and all other groups are as defined herein in any aspect or embodiment described herein. In some or any embodiments, provided is a Compound of Formula (IA), Formula I-P, Formula (Ia), or Formula (Ib), where one $R^6$ is $C_1$-$C_6$-alkoxycarbonyl; and all other groups are as defined herein in any aspect or embodiment described herein.

In another aspect, provided is a Compound of Formula (II):

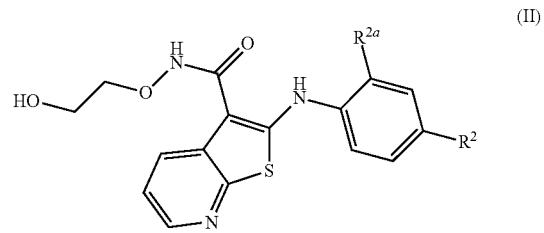

where
$R^{2a}$ is halo or $C_1$-$C_6$ alkyl; and
$R^2$ is —S—$C_1$-$C_6$ alkyl, $C_1$-$C_6$ alkyl, $C_2$-$C_6$ alkenyl, $C_2$-$C_6$ alkynyl, or halo;
or an N-oxide, a stereoisomer, mixture of stereoisomers, and/or a pharmaceutically acceptable salt thereof. In some or any embodiments of Formula (II), $R^2$ is $C_1$-$C_6$ alkyl or halo; or an N-oxide, a stereoisomer, mixture of stereoisomers, and/or a pharmaceutically acceptable salt thereof. In some or any embodiments of Formula (II), $R^2$ and $R^{2a}$ are independently halo; or an N-oxide, a stereoisomer, mixture of stereoisomers, and/or a pharmaceutically acceptable salt thereof. In some or any embodiments of Formula (II), $R^2$ is iodo and $R^{2a}$ is fluoro; or an N-oxide, a stereoisomer, mixture of stereoisomers, and/or a pharmaceutically acceptable salt thereof. In some or any embodiments of Formula (II), $R^{2a}$ is fluoro and $R^2$ is iodo, $R^{2a}$ is methyl and $R^2$ is iodo, $R^{2a}$ is fluoro and $R^2$ is ethynyl, $R^{2a}$ is methyl and $R^2$ is ethynyl, $R^{2a}$ is fluoro and $R^2$ is methylthio, or $R^{2a}$ is methyl and $R^2$ is methylthio; or an N-oxide, a stereoisomer, mixture of stereoisomers, and/or a pharmaceutically acceptable salt thereof. In some or any embodiments of Formula (II), $R^{2a}$ is fluoro and $R^2$ is iodo; or an N-oxide, a stereoisomer, mixture of stereoisomers, and/or a pharmaceutically acceptable salt thereof. In some or any embodiments of Formula (II), $R^{2a}$ is methyl and $R^2$ is iodo; or an N-oxide, a stereoisomer, mixture of stereoisomers, and/or a pharmaceutically acceptable salt thereof. In some or any embodiments of Formula (II), $R^{2a}$ is fluoro and $R^2$ is ethynyl; or an N-oxide, a stereoisomer, mixture of stereoisomers, and/or a pharmaceutically acceptable salt thereof. In some or any embodiments of Formula (II), $R^{2a}$ is methyl and $R^2$ is ethynyl; or an N-oxide, a stereoisomer, mixture of stereoisomers, and/or a pharmaceutically acceptable salt thereof. In some or any embodiments of Formula (II), $R^{2a}$ is fluoro and $R^2$ is methylthio; or an N-oxide, a stereoisomer, mixture of stereoisomers, and/or a pharmaceutically acceptable salt thereof. In some or any embodiments of Formula (II), $R^{2a}$ is methyl and $R^2$ is methylthio; or an N-oxide, a stereoisomer, mixture of stereoisomers, and/or a pharmaceutically acceptable salt thereof.

In some or any embodiments, the Compound of Formula (I) is according to any of the following formula:

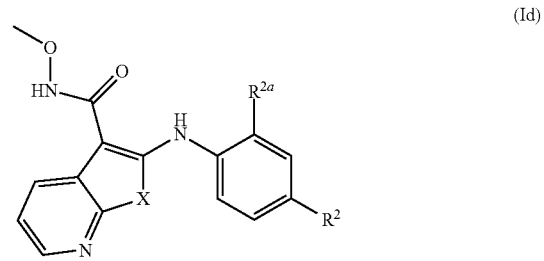

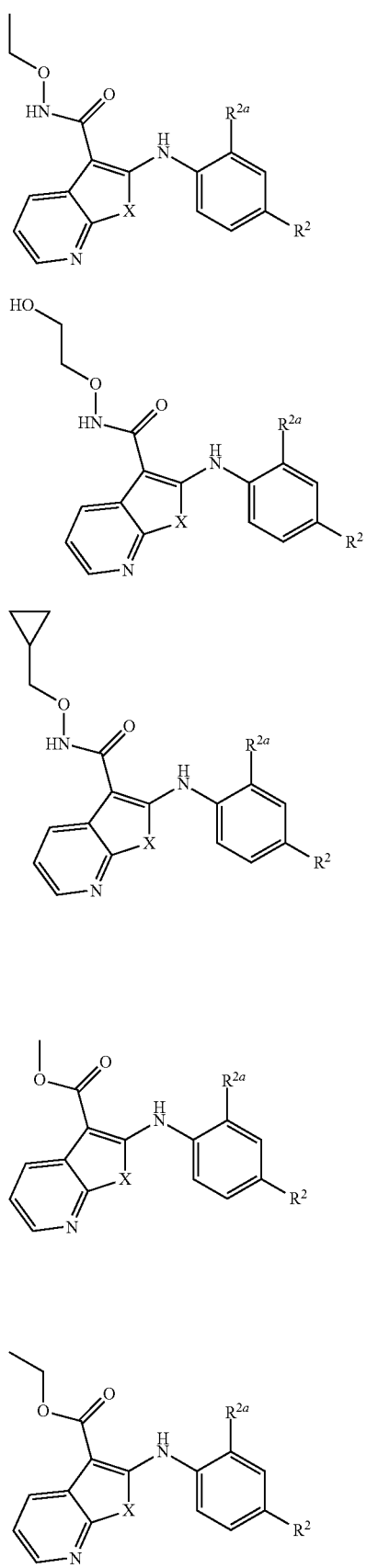
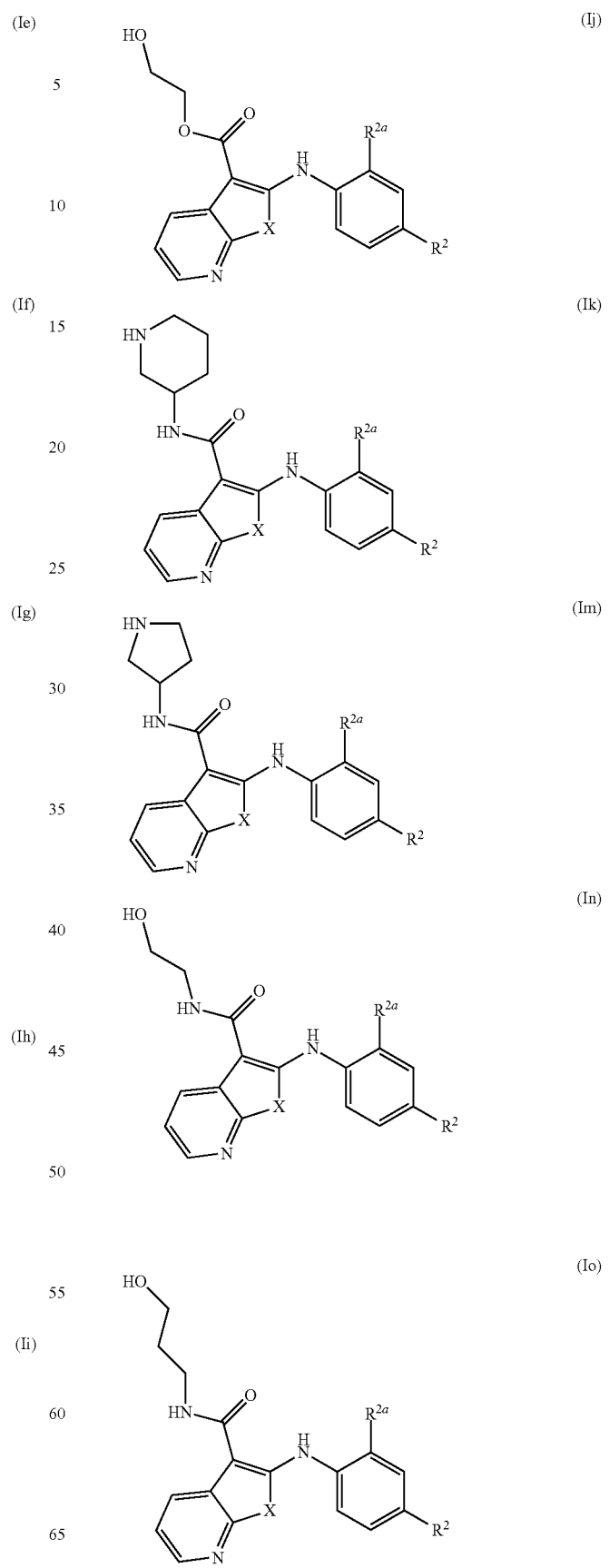

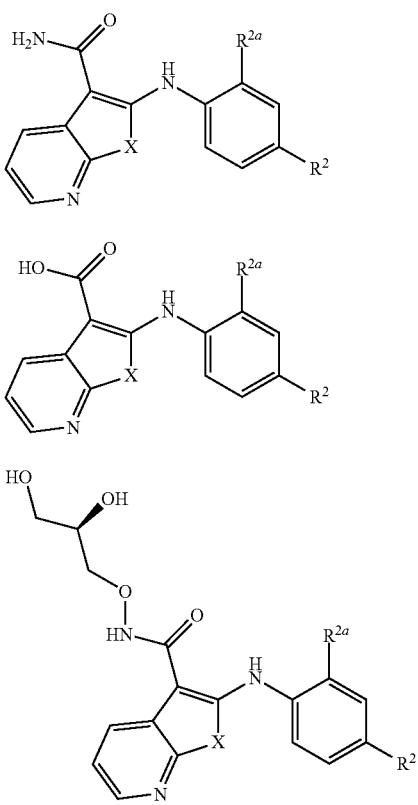

(Ip)

(Iq)

(Ir)

(Is)

(It)

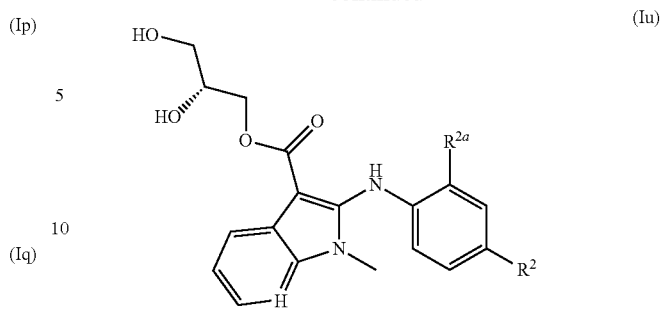

(Iu)

In some or any embodiments of the above structures, X is S; and all other groups are as defined herein in any aspect or embodiment described herein. In some or any embodiments of the above structures, $R^{2a}$ is fluoro and $R^2$ is iodo, $R^{2a}$ is methyl and $R^2$ is iodo, $R^{2a}$ is fluoro and $R^2$ is ethynyl, $R^{2a}$ is methyl and $R^2$ is ethynyl, $R^{2a}$ is fluoro and $R^2$ is methylthio, or $R^{2a}$ is methyl and $R^2$ is methylthio; and all other groups are as defined herein in any aspect or embodiment described herein. In some or any embodiments of the above structures, $R^{2a}$ is fluoro and $R^2$ is iodo; and all other groups are as defined herein in any aspect or embodiment described herein. In some or any embodiments of the above structures, $R^{2a}$ is methyl and $R^2$ is iodo; and all other groups are as defined herein in any aspect or embodiment described herein. In some or any embodiments of the above structures, $R^{2a}$ is fluoro and $R^2$ is ethynyl; and all other groups are as defined herein in any aspect or embodiment described herein. In some or any embodiments of the above structures, $R^{2a}$ is methyl and $R^2$ is ethynyl; and all other groups are as defined herein in any aspect or embodiment described herein. In some or any embodiments of the above structures, $R^{2a}$ is fluoro and $R^2$ is methylthio; and all other groups are as defined herein in any aspect or embodiment described herein. In some or any embodiments of the above structures, $R^{2a}$ is methyl and $R^2$ is methylthio; and all other groups are as defined herein in any aspect or embodiment described herein.

In some embodiments, provided herein are:
(a) compounds as described herein, e.g., of Formula (IA), Formula (I), Formula (I-P), Formula (Ia)-(Iu), or Formula (II), the claims, and compounds in Embodiment A, and pharmaceutically acceptable salts and compositions thereof;
(b) compounds as described herein, e.g., of Formula (IA), Formula (I), Formula (I-P), Formula (Ia)-(Iu), or Formula (II), the claims, and compounds in Embodiment A, and pharmaceutically acceptable salts and compositions thereof for use in the treatment of MEK-inhibitor responsive disorder, MEK-inhibitor responsive dermal disorder, MEK-mediated disorder or disease, or disease or a MEK-mediated dermal disorder or disease where the subject is in need thereof;
(c) processes for the preparation of compounds as described herein, e.g., of Formula (IA), Formula (I), Formula (I-P), Formula (Ia)-(Iu), or Formula (II), the claims, and compounds in Embodiment A, as described in more detail elsewhere herein;
(d) pharmaceutical formulations comprising a compound as described herein, e.g., of Formula (IA), Formula (I), Formula (I-P), Formula (Ia)-(Iu), or Formula (II), the claims, and compounds in Embodiment A, or a phar-

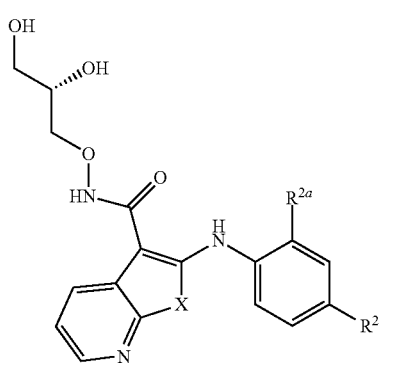

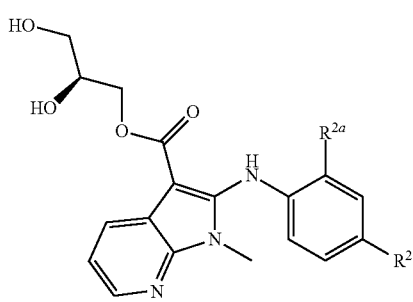

maceutically acceptable salt thereof together with a pharmaceutically acceptable carrier or diluent;

(e) a method for the treatment of a condition, where the subject is in need thereof, that includes the administration of a therapeutically or prophylactically effective amount of a compound as described herein, e.g., of Formula (IA), Formula (I), Formula (I-P), Formula (Ia)-(Iu), or Formula (II), the claims, and compounds in Embodiment A, its pharmaceutically acceptable salt or composition;

(f) a method for the treatment of MEK-inhibitor responsive disorder, MEK-inhibitor responsive dermal disorder or disease, MEK-mediated disorder or disease, or a MEK-mediated dermal disorder or disease in a subject that includes the administration of a therapeutically or prophylactically effective amount of a compound as described herein, e.g., of Formula (IA), Formula (I), Formula (I-P), Formula (Ia)-(Iu), or Formula (II), the claims, and compounds in Embodiment A, its pharmaceutically acceptable salt or composition;

(g) pharmaceutical formulations comprising a compound as described herein, e.g., of Formula (IA), Formula (I), Formula (I-P), Formula (Ia)-(Iu), or Formula (II), the claims, and compounds in Embodiment A, or a pharmaceutically acceptable salt thereof together with one or more other effective agents for treating MEK-inhibitor responsive disorder, MEK-inhibitor responsive dermal disorder or disease, MEK-mediated disorder or disease, or a MEK-mediated dermal disorder or disease where the subject is in need thereof, optionally in a pharmaceutically acceptable carrier or diluent;

(h) a method for the treatment of a MEK-inhibitor responsive disorder, MEK-inhibitor responsive dermal disorder or disease, MEK-mediated disorder or disease, or MEK-mediated dermal disorder or disease in a subject that includes the administration of a therapeutically or prophylactically effective amount of a compound as described herein, e.g., of Formula (IA), Formula (I), Formula (I-P), Formula (Ia)-(Iu), or Formula (II), the claims, and compounds in Embodiment A, its pharmaceutically acceptable salt or composition in combination and/or alternation with one or more agent for the treatment of a MEK-inhibitor responsive disorder, MEK-inhibitor responsive dermal disorder or disease, MEK-mediated disorder or disease, or a MEK-mediated dermal disorder or disease where the subject is in need thereof; and (i) a method for the treatment of a condition, where the subject is in need thereof, that includes the administration of a therapeutically or prophylactically effective amount of a compound as described herein, e.g., of Formula (IA), Formula (I), Formula (I-P), Formula (Ia)-(Iu), or Formula (II), the claims, and compounds in Embodiment A, or its pharmaceutically acceptable salt or composition in combination and/or alternation with one or more agent for the treatment of a MEK-inhibitor responsive disorder, MEK-inhibitor responsive dermal disorder or disease, MEK-mediated disorder or disease, or a MEK-mediated dermal disorder or disease.

Optically Active Compounds

It is appreciated that compounds provided herein have several chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (in certain embodiments, by resolution of the racemic form by recrystallization techniques, by synthesis from optically-active starting materials, by chiral synthesis, or by chromatographic separation using a chiral stationary phase). In addition, the compounds described herein may epimerize at the C11 position under certain conditions. Such epimers are within the embodiments provided herein.

In certain embodiments, methods to obtain optically active materials are known in the art, and include at least the following.

i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;

ii) simultaneous crystallization—a technique whereby the individual stereoisomers are separately crystallized from a solution of the racemate, possible only if the latter is a conglomerate in the solid state;

iii) enzymatic resolutions—a technique whereby partial or complete separation of a racemate by virtue of differing rates of reaction for the stereoisomers with an enzyme;

iv) enzymatic asymmetric synthesis—a synthetic technique whereby at least one step of the synthesis uses an enzymatic reaction to obtain an stereoisomerically pure or enriched synthetic precursor of the desired stereoisomer;

v) chemical asymmetric synthesis—a synthetic technique whereby the desired stereoisomer is synthesized from an achiral precursor under diseases or disorders that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

In some embodiments, provided is a composition of a compound that comprises a substantially pure designated stereoisomer of the compound. In certain embodiments, in the methods and compounds, the compounds are substantially free of other stereoisomers. In some embodiments, provided is a composition of a compound that comprises a substantially pure designated enantiomer of the compound. In certain embodiments, in the methods and compounds, the compounds are substantially free of other enantiomers. In some embodiments, provided is a composition of a compound that comprises a substantially pure designated diastereomer of the compound. In certain embodiments, in the methods and compounds, the compounds are substantially free of other diastereomers. In some embodiments, provided is a composition of a compound that comprises a substantially pure geometric isomer of the compound. In certain embodiments, in the methods and compounds, the compounds are substantially free of other geometric isomers. In some embodiments, a composition includes a compound that is at least 85%, 90%, 95%, 98%, 99% or 100% by weight, of the compound, the remainder comprising other chemical species or stereoisomers.

Isotopically Enriched Compounds

Also provided herein are isotopically enriched compounds. Isotopic enrichment (in certain embodiments, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, in certain embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster el at., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In certain embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Pharmaceutical Compositions and Methods of Administration

The compounds of Formula I-A, Formula I-P, Formula I, Formula Ia, Formula Ib, or Formula II, provided herein, or combinations thereof, can be formulated into pharmaceutical compositions using methods available in the art and those disclosed herein. Any of the compounds disclosed herein can be provided in the appropriate pharmaceutical composition and be administered by a suitable route of administration.

In some or any embodiments, administration of the compound described herein to a subject may be local or non-systemic, e.g., topical, subcutaneous, transdermal, intradermal, or intralesional. In an embodiment, the compound can be administered by topical administration. In an embodiment, the compound can be administered by intradermal administration. In an embodiment, the compound can be administered by intralesional administration, e.g., by intralesional injection.

The methods provided herein encompass administering pharmaceutical compositions containing at least one compound as described herein, including a compound of Formula I-A, Formula I-P, Formula I, Formula Ia, Formula Ib, or Formula II and the claims, and compounds in Embodiment A, if appropriate in a salt form, either used alone or in the form of a combination with one or more compatible and pharmaceutically acceptable carriers, such as diluents or adjuvants, or with another agent for the treatment of MEK-inhibitor responsive disorder or disease, MEK-inhibitor responsive dermal disorder or disease, MEK-mediated disorder or disease, or a MEK-mediated dermal disorder or disease where the subject is in need thereof.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular topically, subcutaneously, transdermally, intradermally, intralesionally orally, parenterally, rectally or by inhalation (e.g. in the form of aerosols). In certain embodiments, the compound provided herein is administered topically, subcutaneously, transdermally, intradermally, or intralesionally. In certain embodiments, the compound provided herein is administered topically. In certain embodiments, the compound provided herein is administered intradermally. In certain embodiments, the compound provided herein is administered intralesionally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

Use may be made, of compositions for topical administration as lotions, tinctures, creams, emulsions, gels or ointments. In these compositions, the active product is mixed with one or more inert excipients including water, acetone, ethanol, ethylene glycol, propylene glycol, butane 1,3 diol, isopropyl myristate, isopropyl palmitate, mineral oil, and mixtures thereof.

The compositions for parenteral, intralesional, or intradermal administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in a pyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In certain embodiments, the route of administration is intradermal, transdermal, topical, subcutaneous, or intralesional administration. In certain embodiments, the route of administration is non-systemic administration. In a specific embodiment, the composition is formulated in accordance with routine procedures as a pharmaceutical composition adapted for intravenous, subcutaneous, intramuscular, oral, intranasal, transdermal, intradermal, intralesional, or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of a MEK-inhibitor responsive disorder or disease, MEK-inhibitor responsive dermal disorder or disease, MEK-mediated disorder or disease, or a MEK-mediated dermal disorder or disease may contain larger amounts of one or more of the active ingredients it comprises than a dosage form used in the maintenance treatment of the same disorder or disease. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous diseases or disorders with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrates that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the disease or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of one or more side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various diseases or disorders including, but not limited to, pH, temperature, enzymes, water, or other physiological diseases or disorders or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson. Medical Applications of Controlled Release, vol. 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, poly dimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. In certain embodiments, parenteral dosage forms can be administered to subjects by various routes including, but not limited to, subcutaneous, intravenous (including bolus injection), intramuscular, and intra-arterial. In certain embodiments, parenteral dosage forms can be administered to subjects by various routes including, but not limited to, topical, subcutaneous, transdermal, intradermal, or intralesional. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Suitable carriers (e.g., excipients and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical carriers include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. In some embodiments, materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, a doctor will determine the posology which he considers most appropriate according to a preventive or curative treatment and according to the age, weight, stage of the disorder or disease and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a disease or disorder where the subject is in need thereof and/or MEK-inhibitor responsive disorder or disease, MEK-inhibitor responsive dermal disorder or disease, MEK-mediated disorder or disease, or a MEK-mediated dermal disorder or disease in a subject by administering, to a subject in need thereof, a therapeutically or prophylactically effective amount of a compound provided herein, or a pharmaceutically acceptable salt thereof. The amount of the compound or composition which will be therapeutically or prophylactically effective in the treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, between 0.30 mg/kg and 1.50 mg/kg, between 1 mg/kg and 100 mg/kg, between 5 mg/kg and 50 mg/kg, between 10 mg/kg and 50 mg/kg, between 20 mg/kg and 50 mg/kg, between 15 mg/kg and 40 mg/kg, between 15 mg/kg and 35 mg/kg, between 15 mg/kg and 30 mg/kg, between 25 mg/kg and 35 mg/kg, between 10 mg/kg and 30 mg/kg, between 10 mg/kg and 20 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg of the subject's body weight.

In certain embodiments, the recommended daily dose range of a composition provided herein for the diseases or disorders described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosage may vary within a range depending upon the dosage form employed and the route of administration utilized. For any compound, the therapeutically effective dose can be estimated initially from cell culture assays. A dose may be formulated in animal models to achieve a level in the skin with the lesion, e.g., the dermal neurofibroma, the cutaneous neurofibroma, the subdermal neurofibroma, or the superficial plexiform neurofibroma) that includes the $IC_{50}$ (i.e., the concentration of the test compound that achieves a half-maximal inhibition of symptoms) as determined in cell culture. Such information can be used to more accurately determine useful doses in humans. In addition, levels in plasma may be measured, for example, by high performance liquid chromatography, in order to ascertain systemic exposure.

It should also be understood that a specific dosage and treatment regimen for any particular patient will depend upon a variety of factors, including the activity of the specific compound employed, the age, the size of the lesion, number of lesions, general health, sex, diet, time of administration, drug combination, and the judgment of the treating physician and the severity of the particular disease being treated. The amount of a soft MEK inhibitor, e.g., a soft MEK inhibitor described herein, in the composition will also depend upon the particular soft MEK inhibitor in the composition.

In some embodiments, the topical, subcutaneous, transdermal, intradermal, or intralesional dose is about 0.01 $\mu g/cm^2$, about 0.05 $\mu g/cm^2$, about 0.1 $\mu g/cm^2$, about 0.15 $\mu g/cm^2$, about 0.2 $\mu g/cm^2$, about 0.3 $\mu g/cm^2$, about 0.4 $\mu g/cm^2$, about 0.5 $\mu g/cm^2$, about 0.6 $\mu g/cm^2$, about 0.7 $\mu g/cm^2$, about 0.8 $\mu g/cm^2$, or about 0.9 $\mu g/cm^2$; or is within about 0.01-0.03 $\mu g/cm^2$, about 0.03-0.05 $\mu g/cm^2$, about 0.05-0.1 $\mu g/cm^2$, about 0.1-0.3 $\mu g/cm^2$, about 0.3-0.5 $\mu g/cm^2$, about 0.5-0.8 $\mu g/cm^2$, about 0.8-1.0 $\mu g/cm^2$, about 1-10 $\mu g/cm^2$, about 10-20 $\mu g/cm^2$, about 20-30 $\mu g/cm^2$, about 30-40 $\mu g/cm^2$, about 40-50 $\mu g/cm^2$, about 50-60 $\mu g/cm^2$, about 60-70 $\mu g/cm^2$, about 70-80 $\mu g/cm^2$, about 80-90 $\mu g/cm^2$, about 90-100 $\mu g/cm^2$, about 100-125 $\mu g/cm^2$, about 125-150 $\mu g/cm^2$, about 150-175 $\mu g/cm^2$, about 175-200 $\mu g/cm^2$, about 200-250 $\mu g/cm^2$, about 250-300 $\mu g/cm^2$, about 300-350 $\mu g/cm^2$, about 350-400 $\mu g/cm^2$, about 400-450 $\mu g/cm^2$, about 450-500 $\mu g/cm^2$, about 500-550 $\mu g/cm^2$, about 550-600 $\mu g/cm^2$, about 600-650 $\mu g/cm^2$, about 650-700 $\mu g/cm^2$, about 700-750 $\mu g/cm^2$, about 750-800 $\mu g/cm^2$, about 800-850 $\mu g/cm^2$, about 850-900 $\mu g/cm^2$, about 900-950 $\mu g/cm^2$, or about 950-1000 $\mu g/cm^2$.

In some embodiments, the topical, subcutaneous, transdermal, intradermal, or intralesional dose is within about 0.5-1.0 $mg/cm^2$, 1.0-1.5 $mg/cm^2$, 1.5-2.0 $mg/cm^2$, 2.5-2.5 $mg/cm^2$, 3.0-3.5 $mg/cm^2$, 3.5-5.0 $mg/cm^2$, 5.0-7.5 $mg/cm^2$, 7.5-10 $mg/cm^2$, 1-10 $mg/cm^2$, about 10-20 $mg/cm^2$, about 20-30 $mg/cm^2$, about 30-40 $mg/cm^2$, about 40-50 $mg/cm^2$, about 50-60 $mg/cm^2$, about 60-70 $mg/cm^2$, about 70-80 $mg/cm^2$, about 80-90 $mg/cm^2$, about 90-100 $mg/cm^2$, about 100-125 $mg/cm^2$, about 125-150 $mg/cm^2$, about 150-175 $mg/cm^2$, about 175-200 $mg/cm^2$, about 200-250 $mg/cm^2$, about 250-300 $mg/cm^2$, about 300-350 $mg/cm^2$, about 350-400 $mg/cm^2$, about 400-450 $mg/cm^2$, about 450-500 $mg/cm^2$, about 500-550 $mg/cm^2$, about 550-600 $mg/cm^2$, about 600-650 $mg/cm^2$, about 650-700 $mg/cm^2$, about 700-750 $mg/cm^2$, about 750-800 $mg/cm^2$, about 800-850 $mg/cm^2$, about 850-900 $mg/cm^2$, about 900-950 $mg/cm^2$, or about 950-1000 $mg/cm^2$.

In certain embodiments, dosages of the second agents to be used in a combination therapy are provided herein. In certain embodiments, dosages lower than those which have been or are currently being used to treat MEK-inhibitor responsive dermal disorder or disease, MEK-inhibitor responsive dermal disorder or disease, MEK-mediated disorder or disease, or a MEK-mediated dermal disorder or disease are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics $9^{th}$ Ed, McGraw-Hill, New York; Physician's Desk Reference (PDR) $57^{th}$ Ed., 2003, Medical Economics Co., Inc., Montvale, N.J.; which are incorporated herein by reference in their entirety.

The disclosure provides combination treatments by administration of a MEK inhibitor, e.g. a soft MEK inhibitor, described herein with one or more additional agent(s). In an embodiment, the one or more additional agent(s) is selected from:

agents that treat acne (e.g., Accutane, Azelaic acid, Benzoyl Peroxide, Salicylic acid);

analgesics (e.g., Acetaminophen, Capsaicin), e.g., a Cox2 Inhibitor, e.g. Celecoxib);

anesthetics (e.g., Benzocaine, Benzocaine/Menthol, Dibucaine, Diperodon, Lidocaine, Lidocaine/Prilocaine, Pramoxine);

anti-infectives (e.g., Crotamiton);

anti-pruritus (e.g., Ammonium lactate, Benzocaine, an ascomycin macrolactam, e.g., Pimecrolimus);

anti-pruritus/5HT3 receptor antagonists (e.g., Ondansetron);

antibiotics (e.g., clindamycin, doxycycline, erythromycin, tetracycline);

anticholinergic antiemetics (e.g., diphenhydramine);

antifibrotics (e.g., Collagenase, Pirfenidone);

antihistamines (e.g., Triprolidine (Actifed®), Fexofenadine (Allegra®, Allegra® D-12, Allegra®-24), Astepro/Astelin Nasal Spray (Azalastine) (Dymista®), Hydroxyzine hydrochloride (Atarax®), Diphenhydramine Hydrochloride (Benadryl®), Brompheniramine (Dimetapp® Cold and Allergy Elixir), Zyrtec® (Cetirizine), Chlor-Trimeton® (Chlorpheniramine), Descoratadine (Clarinex®, Clarinex® D-12, and Clarinex® D-24), Loratadine (Claritin®, Claritin® D-12, Claritin® D-24, and Alavert®), Dimenhydrinate (Dramamine®), Diphenhydramine (Benadryl® Allergy, Nytol®, Sominex®), Doxylamine (Vicks® NyQuil®, Alka-Seltzer® Plus Night-Time Cold Medicine), Cyproheptadine (Periactin®), Promethazine (Phenergan®), Acrivastine (Semprex®, Semprex®-D), Clemastine (Tavist®), doxylamine (Unisom®), Levocetirizine (Xyzal®);

mast cell stabilizers (e.g. Beta2-adrenergic agonists, Cromoglicic acid, cromolyn sodium, Gastrocrom®, Ketotifen, Methylxanthines, Omalizumab, Pemirolast, Quercetin, Ketotifen (Zaditen®));

anti-inflammatory agents (e.g., NSAID (e.g. Aspirin, Choline and magnesium salicylates, Diclofenac potassium (Cataflam®), Diclofenac sodium (Voltaren®, Voltaren® XR), Diclofenac sodium with misoprostol (Arthrotec®), Diflunisal (Dolobid®), Etodolac (Lodine®, Lodine® XL), Fenoprofen calcium (Nalfon®), Flurbiprofen (Ansaid®), Ibuprofen (Advil®, Motrin®, Motrin® IB, Nuprin®), Indomethacin (Indocin®, Indocin® SR), Ketoprofen (Actron®, Orudis®, Orudis® KT, Oruvail®), Magnesium salicylate (Arthritab, Bayer® Select, Doan's Pills, Magan, Mobidin, Mobogesic) Meclofenamate sodium (Meclomen®), Mefenamic acid (Ponstel®), Meloxicam (Mobic®), Nabumetone (Relafen®), Naproxen (Naprosyn®, Naprelan®), Naproxen sodium (Aleve®, Anaprox®), Oxaprozin (Daypro®), Piroxicam (Feldene®), Rofecoxib (Vioxx®), Salsalate (Amigesic, Anaflex 750, Disalcid, Marthritic, Mono-Gesic, Salflex, Salsitab), Sodium salicylate, Sulindac (Clinoril®), Tolmetin sodium (Tolectin®), Valdecoxib (Bextra®));

Receptor Tyrosine Kinase Inhibitor (e.g. Sunitinib);

Alkylating Agents (e.g., Dacarbazine, Carboplatin);

CDK 4/6 Inhibitors (e.g., LEE011);

PKC Inhibitors (e.g., AEB071);

MAPK inhibitors (e.g., RAS Inhibitors/Famesyltransferase inhibitor (e.g. Tipifamib), Raf Kinase Inhibitor (e.g. Sorafenib (BAY 43-9006, Nexavar), Vemurafenib, Dabrafenib, LGX818, TAK-632, MLN2480, PLX-4720), ERK Inhibitors (e.g., SCH772984, VTXlle);

PI3K Inhibitor (e.g., LY294002);

AKT Inhibitor (e.g., MK 2206);

PI3K/AKT Inhibitor (e.g. buparbsib, Cixutumumab);

mTOR Inhibitors (e.g. Topical Rapamycin, RAD001 (Everolimus/Rapamycin), Temsirolimus, Sirolimus);

Tyrosine Kinase Inhibitors (e.g. Imatinib (Gleevec®), Cabozantinib (inhibitor of tyrosine kinases c-Met and VEGFR2), Nilotinib (Tasigna®);

VEGF Inhibitor (e.g. Ranibizumab (Lucentis®), Cediranib);

Immune Response Modifier (e.g. Topical Imiquimod, Interferon, PEG Interferon);

Calcium Channel Blocker (e.g. Avocil (Mederma)/15% Verapamil, vitamin D separately, Doxycyline Injections);

Statin (e.g. Lovastatin, Methotrexate, Vinblastine, Pregabalin, Temozolomide, PLX3397);

HDAC Inhibitor (e.g. AR-42);

HSP-90 Inhibitors (e.g. Ganetespib);

retinoids (e.g. adapalene, Isotretinoin, tazarotene, tretinoin);

steroids (e.g. Alclometasone, Amcinonide, Betamethasone, Betamethasone dipropionate, Betamethasone dipropionate, augmented, Budesonide, Clobetasol propionate, Cortisone, Desonide, Dexamethasone, Diflorasone diacetate, Fluocinolone acetonide, Fluocinonide, Flurandrenolide, Fluticasone propionate, Halobetasol propionate, Halocinonide, Hydrocortisone, Hydrocortisone butyrate, Hydrocortisone valerate, Methylprednisolone, Mometasone, Mometasone furoate, Prednicarbate, Prednisolone, Prednisone, Triamcinolone, Triamcinolone acetonide);

topical calcineurin inhibitors (e.g., pimecrolimus (Elidel® Cream 1%, Novartis, tacrolimus (Protopic® Ointment, Astellas)); and Non-pharmaceutical Interventions (e.g. photodynamic Therapy (Levulan Kerastick Topical+light), Electrodesication (ED), YAG Laser).

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, in certain embodiments, a mammal, such as a human, in a sequence and within a time interval such that the compound provided herein can act together with the other agent to provide an increased benefit than if they were administered otherwise. In certain embodiments, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce one or more of the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In certain embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a MEK-inhibitor responsive disorder or disease, MEK-inhibitor responsive dermal disorder or disease, MEK-mediated dermal disorder or disease, or a MEK-mediated dermal disorder or disease where the subject is in need thereof or a MEK-inhibitor responsive disorder or disease, MEK-inhibitor responsive dermal disorder or disease, MEK-mediated disorder or disease, or a MEK-mediated dermal disorder or disease. The kits can include a compound or composition provided herein, a second agent or composition, and instructions providing information to a health care provider regarding usage for treating a MEK-inhibitor responsive disorder or disease, MEK-inhibitor responsive dermal disorder or disease, MEK-mediated disorder or disease, or a MEK-mediated dermal disorder or disease. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating a disease or disorder where the subject is in need thereof and/or MEK-inhibitor responsive disorder or disease, MEK-inhibitor responsive dermal disorder or disease, MEK-mediated disorder or disease, or a MEK-mediated dermal disorder or disease in a subject, which comprises contacting the subject with a therapeutically or prophylactically effective amount of a compound disclosed herein, e.g., a compound of any one of Formula (I) and the claims, and compounds in Embodiment A, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt, solvate, prodrug, phosphate, or active metabolite thereof.

In certain embodiments, provided herein are methods for treating a MEK-inhibitor responsive disorder or disease, MEK-inhibitor responsive dermal disorder or disease, MEK-mediated disorder or disease, or a MEK-mediated dermal disorder or disease where the subject is in need thereof. In certain embodiments, the methods encompass the step of administering to the subject in need thereof an amount of a compound effective for the treatment of a MEK-inhibitor responsive disorder or disease, MEK-inhibitor responsive dermal disorder or disease, MEK-mediated disorder or disease, or a MEK-mediated dermal disorder or disease where the subject is in need thereof in combination with a second agent effective for the treatment or prevention of a MEK-inhibitor responsive disorder or disease, MEK-inhibitor responsive dermal disorder or disease, MEK-mediated disorder or disease, or a MEK-mediated dermal disorder or disease where the subject is in need thereof. The compound can be any compound as described herein, and the second agent can be any second agent described in the art or herein. In certain embodiments, the compound is in the form of a pharmaceutical composition or dosage form, as described elsewhere herein.

In certain embodiments, provided herein are methods for treating a disease or disorder where the subject is in need thereof. In certain embodiments, the methods encompass the step of administering to the subject in need thereof a therapeutically or prophylactically effective amount of a compound effective for the treatment of a disease or disorder where the subject is in need thereof in combination with a second agent effective for the treatment of a disease or disorder where the subject is in need thereof. The compound can be any compound as described herein, and the second agent can be any second agent described in the art or herein. In certain embodiments, the compound is in the form of a pharmaceutical composition or dosage form, as described elsewhere herein.

Neurofibromatosis type 1 (NF1): In an embodiment, the dermal disorder is associated with NF1. NF1, also known as von Recklinghausen Neurofibromatosis or Peripheral Neurofibromatosis, occurs in approximately 1:3,000 births, and is one of the most prevalent genetic disorders and the most common neurocutaneous disorders. NF1 is caused by a deficiency in neurofibromin, which leads to hyperactivation of various cell-signaling pathways, e.g., Ras and Rho, is associated with several dermal disorders, including dermal neurofibromas (DFs); cutaneous neurofibromas; subdermal neurofibromas; superficial plexiform neurofibromas (PFs); cutaneous neurofibromas (CFs); café au lait spots; and axillary and inguinal freckling. DFs occur in over 95% of NF1 patients. DFs can appear anywhere on the body, with 88% of NF1 patients over 40 years of age having over 100 DFs. DFs can cause both severe physical pain, disfigurement, as well as social anxiety. Facial DFs can create significant social anxiety issues and pain among affected individuals. DFs (also known as cutaneous neurofibromas or discrete neurofibromas) grow from small nerves in the skin or just under the skin and appear as small bumps typically beginning around the time of puberty. Current treatment options for DF are limited to surgical excisin and $CO_2$ laser removal, both of which cause scarring and neither of which is preventative.

Other Dermal Rasopathies: In an embodiment, the dermal disorder is associated with enhanced activation of Ras. In an embodiment, the dermal disorder is selected from: psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots and Multiple lentigines syndrome (formerly called Leopard syndrome).

In some or any embodiments, the disease to be reduced, ameliorated, treated, or prevented is not cancer (e.g. melanoma). In some or any embodiments, the disease to be reduced, ameliorated, treated, or prevented is cancer (e.g. melanoma).

In certain embodiments, the disease to be reduced, ameliorated, treated, or prevented is cancer, a dermal rasopathy, a dermal disorder associated with neurofibromatosis type 1, a dermal neurofibroma, a cutaneous neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In certain embodiments, the disease to be reduced, ameliorated, treated, or prevented is cancer. In certain embodiments, the disease to be reduced, ameliorated, treated, or prevented is selected from the group consisting of basal cell carcinoma, squamous cell carcinoma, aktinic keratosis, Kaposi's sarcoma, dermal lymphoma, cervical cancer, HPV-related squamous cell carcinoma, and melanoma.

In certain embodiments, the disease to be reduced, ameliorated, treated, or prevented is a dermal rasopathy, a dermal disorder associated with neurofibromatosis type 1, a dermal neurofibroma, a cutaneous neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the compounds described herein are used for the reduction of MEK-inhibitor responsive disorder or disease, MEK-inhibitor responsive dermal disorder or disease, MEK-mediated disorder or disease or a MEK-mediated dermal disorder or disease or of a where the subject is in need thereof In some embodiments, the compounds described herein are used for the amelioration of MEK-inhibitor responsive disorder or disease, MEK-inhibitor responsive dermal disorder or disease, MEK-mediated disorder or disease, or a MEK-mediated dermal disorder or disease or of a where the subject is in need thereof In some embodiments, the compounds described herein are used for prevention of MEK-inhibitor responsive disorder or disease, MEK-inhibitor responsive dermal disorder or disease, MEK-mediated disorder or disease, or a MEK-mediated dermal disorder or disease where the subject is in need thereof.

In some embodiments, the compounds described herein are used for treatment of MEK-inhibitor responsive disorder or disease, MEK-inhibitor responsive dermal disorder or disease, MEK-mediated disorder or disease, or a MEK-mediated dermal disorder or disease or of a where the subject is in need thereof.

Assay Methods

Compounds can be assayed for efficacy in treating a MEK-inhibitor responsive disorder or disease, MEK-inhibitor responsive dermal disorder or disease, MEK-mediated disorder or disease, or a MEK-mediated dermal disorder or disease where the subject is in need thereof according to any assay known to those of skill in the art. Exemplary assay methods are provided elsewhere herein.

Second Therapeutic Agents

In certain embodiments, the compounds and compositions provided herein are useful in methods of treatment of MEK-inhibitor responsive disorder or disease, MEK-inhibitor responsive dermal disorder or disease, MEK-mediated disorder or disease, or a MEK-mediated dermal disorder or disease where the subject is in need thereof, that comprise further administration of a second agent effective for the treatment of dermal disorders or diseases. The second agent can be any agent known to those of skill in the art to be effective for the treatment of dermal disorders or diseases, including those currently approved by the United States Food and Drug Administration, or other similar body of a country foreign to the United States.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce one or more adverse or unwanted side effects associated with the use of either therapy alone.

The active compounds provided herein can be administered in combination or alternation with another therapeutic agent, in particular an agent effective in the treatment of MEK-inhibitor responsive disorder or disease, MEK-inhibitor responsive dermal disorder or disease, MEK-mediated disorder or disease, or a MEK-mediated dermal disorder or disease where the subject is in need thereof. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the MEK-inhibitor responsive disorder or disease, MEK-inhibitor responsive dermal disorder or disease, MEK-mediated disorder or disease, or the MEK-mediated dermal disorder or disease or a disorder to be alleviated. It is to be further understood that for any particular subject, specific dosage regimens and schedules should be adjusted over time according to the individual need and the professional judgment of the person administering or supervising the administration of the compositions.

EXAMPLES

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art. As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: h (hour); g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DIPEA (diisopropylethylamine); DMF (dimethyl formamide); DMSO (dimethylsulfoxide); DMSO-d$_6$, (deuterated dimethylsulfoxide); EtOAc (ethyl acetate); MeOH (methanol); TFAA (trifluoroacetic anhydride); UPLC-MS (ultra performance liquid chromatography-mass spectrometry).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

General Schemes

Preparation of Compounds

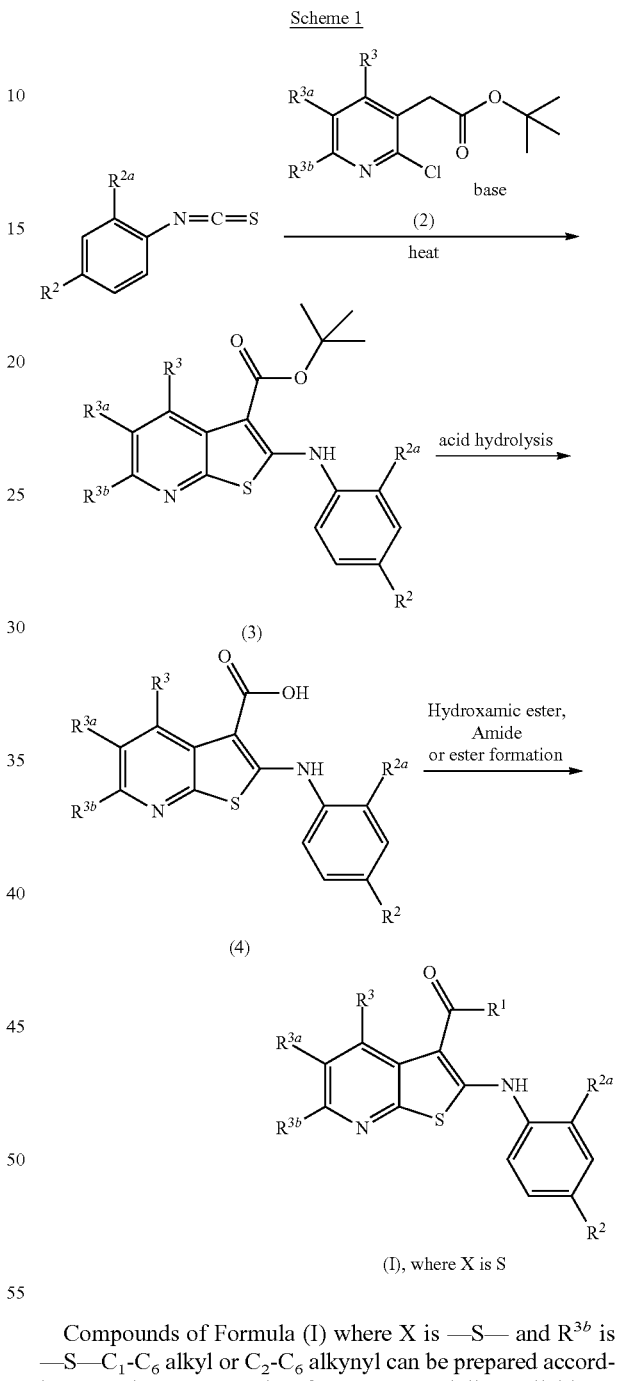

Compounds of Formula (I) where X is —S— and $R^{3b}$ is —S—$C_1$-$C_6$ alkyl or $C_2$-$C_6$ alkynyl can be prepared according to Scheme 1. Starting from commercially-available or routinely-accessible substituted phenyl isothiocyanate (1) and intermediate (2), intermediate (3) can be prepared by methods apparent to those of skill in the art. Intermediate 3 can be readily hydrolyzed by contact with an appropriate acid such as hydrochloric acid or trifluoroacetic acid in an appropriate solvent such as dichloromethane or dioxane to give intermediate 4. The acid intermediate (4), can be activated with numerous reagents apparent to those of skill in the art to produce compounds with a suitable leaving group attached to the carbonyl, such as an acid chloride, produced from the reaction of intermediate (4) with thionyl chloride or the reaction of intermediate (4) with reagents such as EDCI or HOBt. The acid chlorides or active esters can then be reacted with alcohols, amines, and hydroxylamines to produce compounds of Formula (I) where X is —S— and $R^{3b}$ is —S—$C_1$-$C_6$ alkyl or $C_2$-$C_6$ alkynyl.

Alternatively, compounds where X is —S— and $R^2$ is $C_2$-$C_6$ alkynyl group can be prepared according to Scheme 2 where $R^2$ is initially iodo. Reactions conditions similar to those published in the *Journal of Medicinal Chemistry* 2007, 50, 5090-5102 can be employed to afford the transformation from an aromatic iodo group to alkyne. Intermediate (7) can be converted to a Compound of Formula (I) using procedures described herein and above for Scheme 1.

Utilizing the Exemplary Preparation Schemes provided above and procedures known to one of ordinary skill in the art, the following compounds in Embodiment A can be prepared.

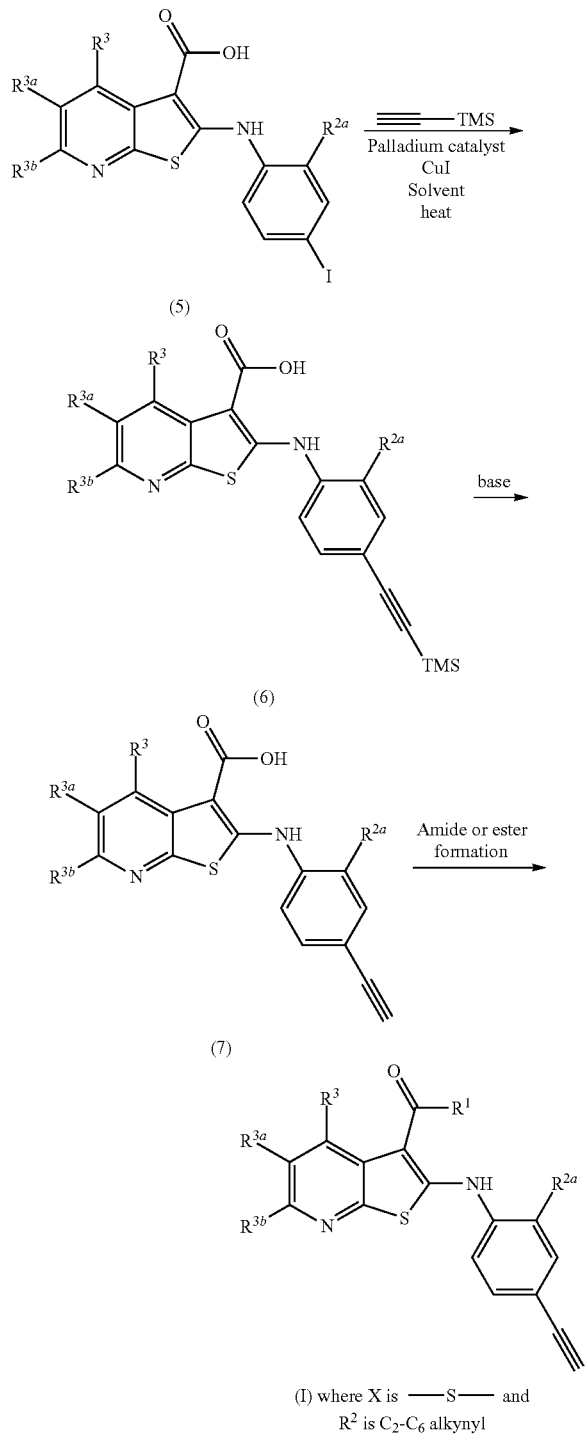

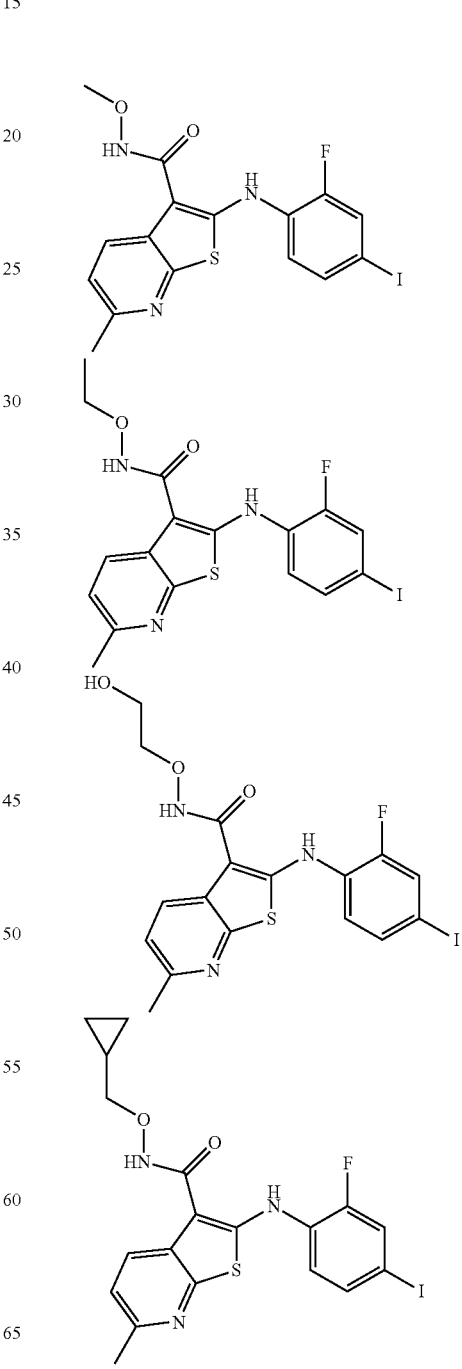

Embodiment A

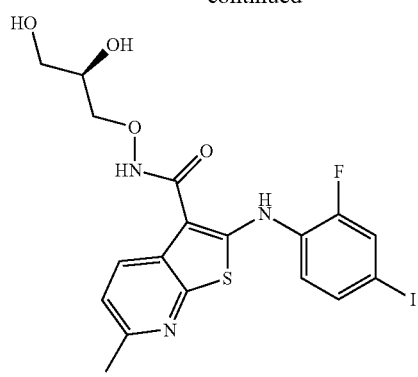
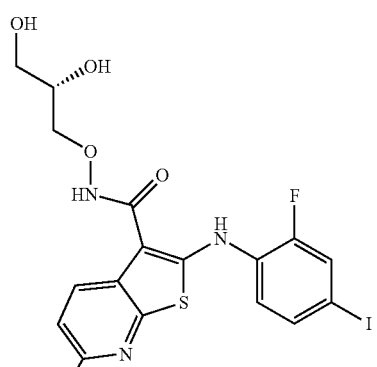
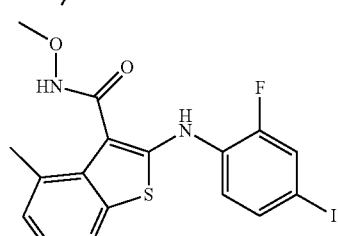
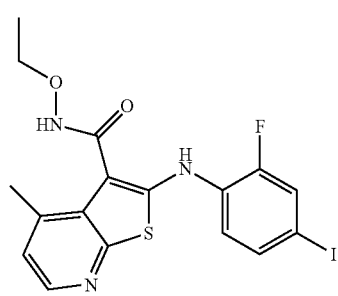
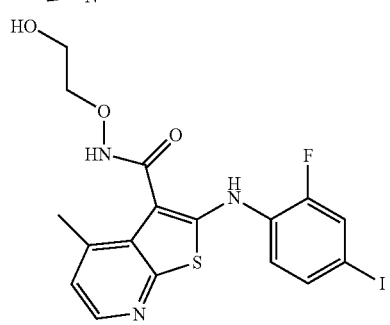
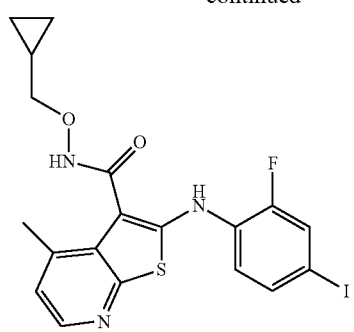
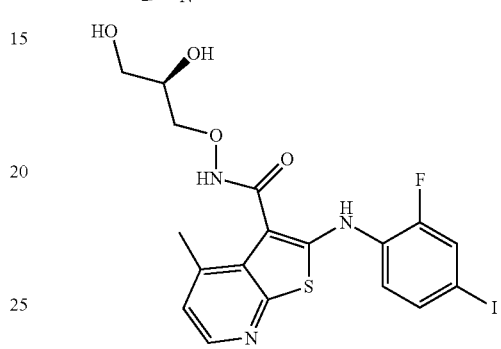
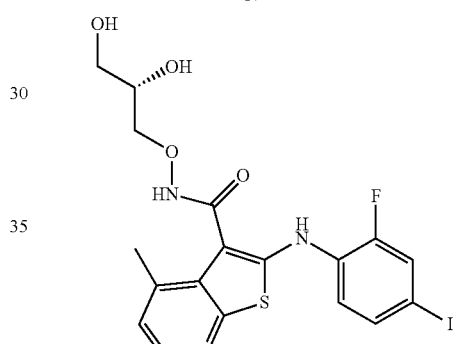
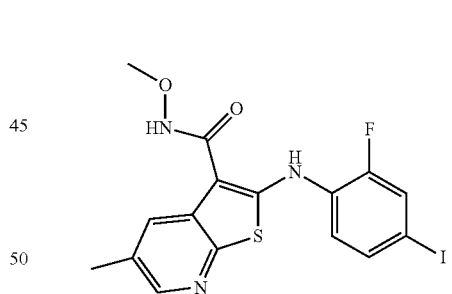
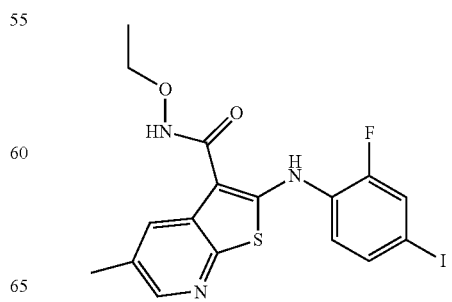

69
-continued
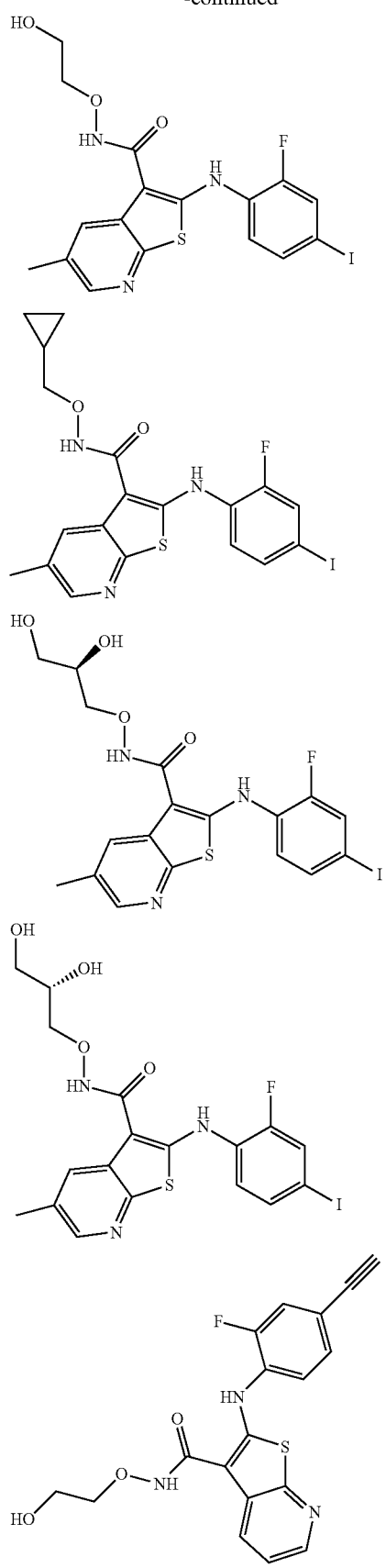
70
-continued
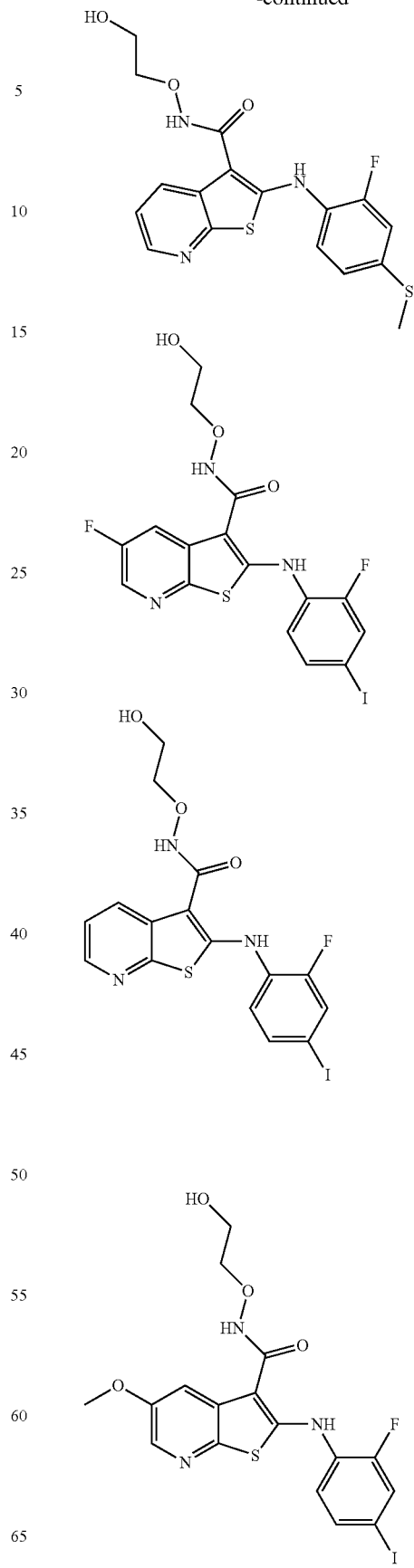

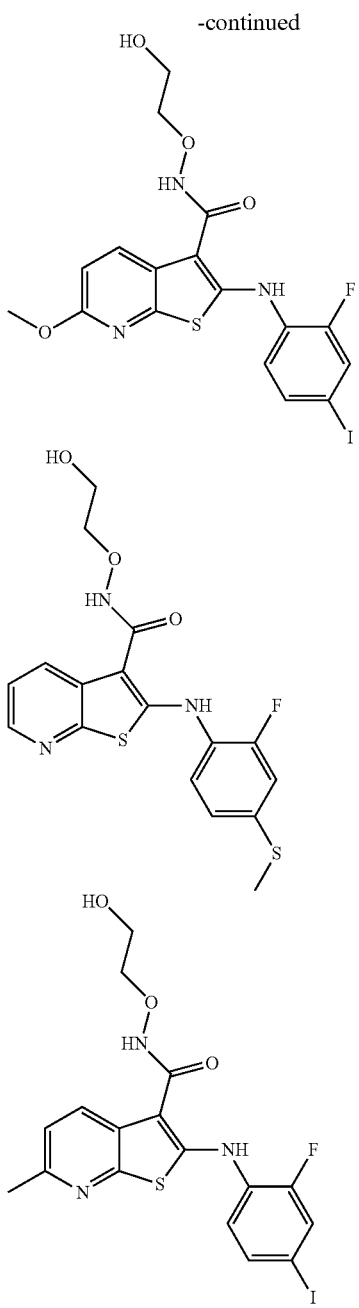

SYNTHETIC EXAMPLES

General Methods
NMR Spectroscopy

The following method was used to record ¹H NMR in Examples 3-8. ¹H NMR spectra were recorded at 400 MHz on a Bruker Avance III NMR spectrometer. Samples were prepared in deuterated chloroform (CDCl₃) or dimethylsulphoxide (DMSO-d₆) and the raw data were processed using the ACD NMR software.

For Examples 1 and 2, ¹H NMR spectra were recorded at 300 MHz on a Varion Mercury NMR.

UPLC-MS Analysis

The following method was used to record LCMS in Examples 3-8.

LCMS analysis was conducted on a Waters Acquity UPLC system consist of an Acquity i-Class Sample Manager-FL, Acquity i-Class Binary Solvent Manager and Acquity i-Class UPLC Column Manager. UV detection was achieved using an Acquity i-Class UPLC PDA detector (scanning from 210-400 nm), whereas mass detection was achieved using an Acquity QDa detector (mass scanning from 100-1250 Da; positive and negative modes simultaneously). A Waters Acquity UPLC BEH C18 column (2.1×50 mm, 1.7 □m) was used to achieve the separation of the analytes.

Samples were prepared by dissolving (with or without sonication) into 1 mL of a 1:1 (v/v) mixture of MeCN in H₂O. The resulting solutions were filtered through a 0.2 μm syringe filter before being submitted for analysis. All of the solvents (including formic acid and 36% ammonia solution) used were used as the HPLC grade.

Four different analytical methods were used for this work, the details of which are presented below.

Acidic Run (2 min):
0.1% v/v Formic acid in water [Eluent A]; 0.1% v/v Formic acid in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Acidic Run (4 min):
0.1% v/v formic acid in water [Eluent A]; 0.1% v/v formic acid in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Basic Run (2 min):
0.1% ammonia in water [Eluent A]; 0.1% ammonia in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Basic Run (4 Min):
0.1% ammonia in water [Eluent A]; 0.1% ammonia in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Example 1: 2-((4-ethynyl-2-fluorophenyl)amino)-N-(2-hydroxyethoxy)thieno[2,3-b]pyridine-3-carboxamide

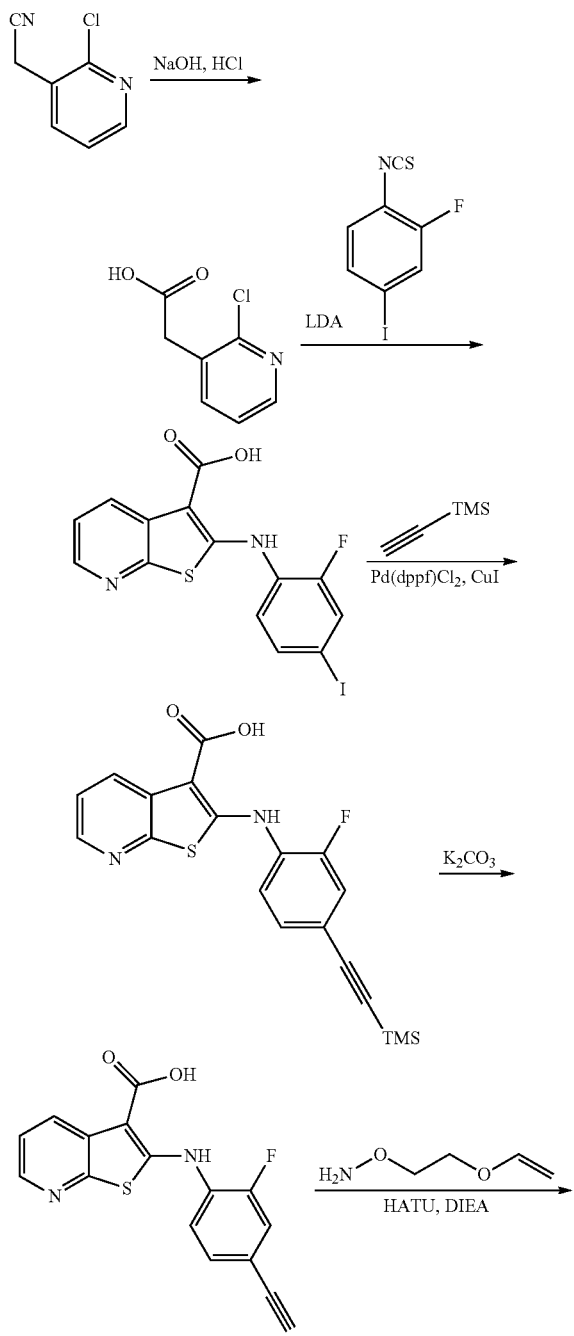

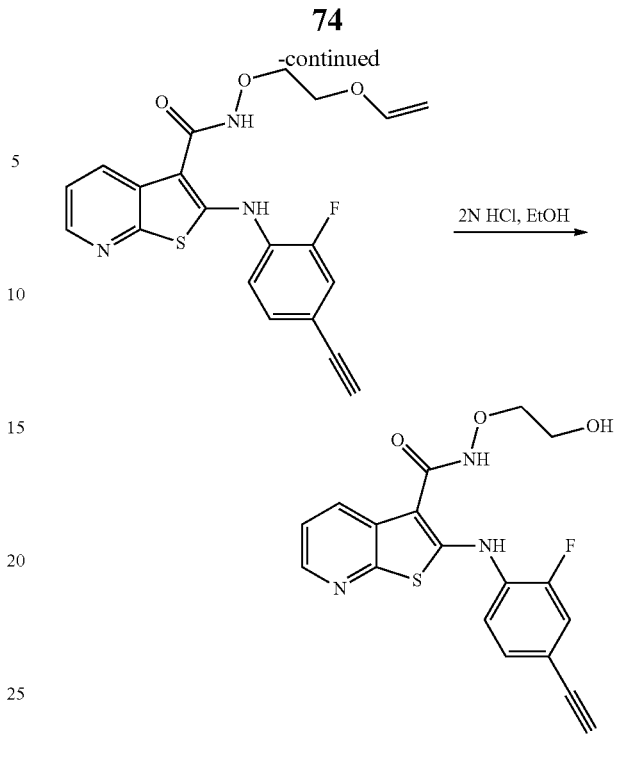

Step 1: 2-fluoro-4-iodo-1-isothiocyanatobenzene

Thiophosgene (8.0 g, 69.6 mmol) was added to a rapidly stirred mixture of 2-fluoro-4-iodoaniline (15.00 g, 63.3 mmol) in dichloromethane (200 mL) and water (150 mL). The reaction mixture was stirred at room temperature overnight. The organic phase was separated, washed with saturated sodium bicarbonate solution, dried over sodium sulfate and filtered. The solvents were removed under vacuum to give the title compound as a beige colored solid (17.1 g, 96.8%). $^1$HNMR (300 MHz, DMSO-d6): δ 7.87 (dd, J=1.8 Hz and 1.8 Hz, 1H), 7.60 (d, J=8.1 Hz, 1H), 7.24 (t, J=8.3 Hz, 1H).

Step 2: 2-(2-chloropyridin-3-yl)acetic Acid

A solution of 15% w/w sodium hydroxide (150 mL) was added to 2-(2-chloropyridin-3-yl)acetonitrile (10.0 g, 62.3 mmol). The mixture was heated at reflux for 1 hour then cooled to room temperature. The mixture was further cooled to 0~5° C. and then acidified with con. HCl (~60 mL) to pH 1. The suspension was left to stand for 1 hour in an ice bath. The precipitate formed was collected by filtration and washed with cold water, then cold 2-propanol (100 mL×2). The solid was dried in a vacuo to get the title compound as an off-white solid (10.6 g, 99%). $^1$HNMR (300 MHz, d$^6$-DMSO): δ 12.63 (s, 1H), 8.32 (dd, J=4.8 and 1.9 Hz, 1H), 7.86 (dd, J=7.6 and 1.9 Hz, 1H), 7.41 (dd, J=7.5 and 4.5 Hz, 1H), 3.75 (s, 2H).

Step 3: 2-((2-fluoro-4-iodophenyl)amino)thieno[2,3-b]pyridine-3-carboxylic Acid

To a stirred solution of diisopropyl amine (0.82 mL, 5.8 mmol) in anhydrous THF (5 mL) cooled to −15° C. was added n-butyl lithium (2.5 M in hexanes, 2.3 mL, 5.8 mmol) slowly, maintaining the temperature of the flask between −10° C. and 0° C. The resultant mixture was stirred at room temperature for 15 minutes before being cooling to 0° C. The LDA thus formed was added to a rapidly stirred suspension of 2-(2-chloropyridin-3-yl)acetic acid (500 mg, 2.9 mmol) in anhydrous THF (10 mL) at 0° C. The resultant bright yellow suspension was stirred at 0° C. for 15 min. A solution of 2-fluoro-4-iodo-1-isothiocyanatobenzene (814 mg, 2.9 mmol) in anhydrous THF (10 mL) was then added to the reaction mixture (brown suspension) and heated to 65° C. for 18 hours. The reaction mixture was cooled and the volatiles removed in vacuo. The resultant crude product was redissolved in THF, cooled to 0° C. and 10% aqueous acetic acid in water (10 mL) was added slowly. Acetonitrile (5 mL) was added slowly until a brown solid developed, the solid was isolated by filtration and washed with ether and acetonitrile to give the title compound. LC/MS: [M+1]+ 415; $^1$H NMR (300 MHz, DMSO-d6): δ 10.74 (s, 1H), 9.21 (s, 1H), 8.36-8.25 (m, 2H), 7.79 (d, J=1.8 Hz, 1H), 7.68-7.61 (m, 1H), 7.51 (t, J=8.5 Hz, 1H), 7.42-7.31 (m, 1H).

Step 4: 2-((2-fluoro-4-((trimethylsilyl)ethynyl)phenyl)amino)thieno[2,3-b]pyridine-3-carboxylic Acid A round bottom flask was charged with 2-((2-fluoro-4-iodophenyl)amino)thieno[2,3-b]pyridine-3-carboxylic acid (0.150 g, 0.4 mmol), copper iodide (3 mg, 0.02 mmol) bis(triphenyl)palladium(II)dichloride (12 mg, 0.02 mmol) in dry THF (10 mL) under nitrogen. The flask was degassed and flushed with nitrogen 3 times. Then trimethyl silyl acetylene (0.040 g, 0.4 mmol) dissolved in 0.4 mL of triethylamine was added very slowly over a period of 10 minutes. The suspension was stirred for 15 hours. The reaction mixture was then poured into ethyl acetate (150 mL) and washed with water (3×50 mL), brine (50 mL) and dried over Na$_2$SO$_4$. The solvents were removed under reduced pressure and the residue purified by flash chromatography (12 g silica, 0-10% MeOH in DCM) to get the product as a pale brown oil (90 mg, 65%). LC/MS: [M+1] 385.1.

Step 5: 2-((4-ethynyl-2-fluorophenyl)amino)thieno[2,3-b]pyridine-3-carboxylic Acid A round bottom flask was charged with 2-((2-fluoro-4-((trimethylsilyl)ethynyl)phenyl)amino)thieno[2,3-b]pyridine-3-carboxylic acid (0.090 g, 0.2 mmol), methanol (5 mL) and THF (1 mL) and potassium carbonate (0.065 g, 0.5 mmol) was added to the resulting suspension. The reaction mixture was stirred at room temperature for 3 hours at which point both TLC and LC/MS indicated completion of the reaction. Water was added to the reaction mixture and extracted with ethyl acetate (3×25 mL) and the combined organics were washed with brine and dried over MgSO$_4$. The solvents were evaporated to dryness to give the compound as brown solid (60 mg, 82%). This was used in the next reaction without further purification. LC/MS: 312.3 [M+1], Step 6: 2-((4-ethynyl-2-fluorophenyl)amino)-N-(2-(vinyloxy)ethoxy)thieno[2,3-b]pyridine-3-carboxamide A microwave vial was charged with 2-((4-ethynyl-2-fluorophenyl)amino)thieno[2,3-b]pyridine-3-carboxylic acid (0.060 g, 0.2 mmol), O-(2-(vinyloxy)ethyl)hydroxylamine (0.03 g, 0.3 mmol), HATU (0.11 g, 0.3 mmol) and diisopropyl ethyl amine (66 ul, 0.4 mmol) in DMF (4 mL). The reaction mixture was stirred at room temperature for 2 hours. The reaction was diluted with water (50 mL) and extracted with ethyl acetate (3×25 mL). The solvents were removed under reduced pressure and the residue purified by flash chromatography (4 g silica, 0-5% MeOH in DCM) to get the product as yellow solid (35 mg, 46%). LC/MS: 398.2 [M+1].

Step 7: 2-((4-ethynyl-2-fluorophenyl)amino)-N-(2-hydroxyethoxy)thieno[2,3-b]pyridine-3-carboxamide A round bottom flask was charged with 2-((4-ethynyl-2-fluorophenyl)amino)-N-(2-(vinyloxy)ethoxy)thieno[2,3-b]pyridine-3-carboxamide (0.03 g, 0.1 mmol), ethanol (3 mL) and 2N HCl (1 mL) and the reaction mixture stirred at room temperature for 1 hour. The solvents were removed and the aqueous residue was neutralized to pH 7 with 1N NaOH solution and extracted with ethyl acetate (3×25 mL). The combined organics were washed with water, brine and dried over MgSO$_4$. The solvents were removed under reduced pressure and the residue was purified by flash chromatography (4 g, 0-10% methanol in dichloromethane) to get the product as pale yellow solid (13 mg, 43%). LC/MS: [M+1]+ 372.0; $^1$H NMR (300 MHz, CDCl3): δ 8.47 (s, 1H), 8.36 (dd, J=4.5 and 1.2 Hz, 1H), 7.90 (dd, J=8.1 and 1.2 Hz, 1H), 7.1 (t, J=8.4 Hz, 1H), 7.37-7.30 (m, 3H), 4.17-4.15 (m, 2H), 3.85 (t, J=4.5 Hz, 2H).

Example 2: 2-((2-fluoro-4-(methylthio)phenyl)amino)-N-(2-hydroxyethoxy)thieno[2,3-b]pyridine-3-carboxamide

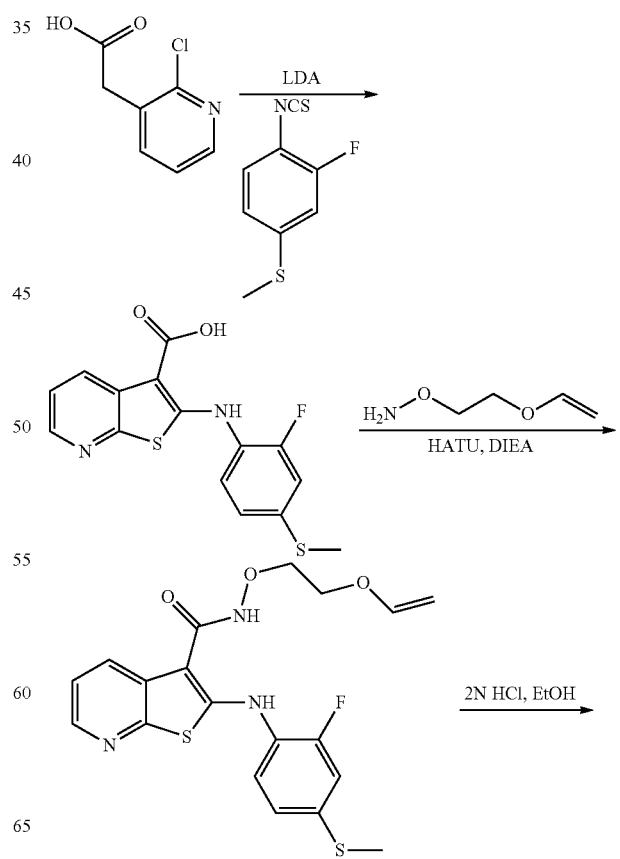

-continued

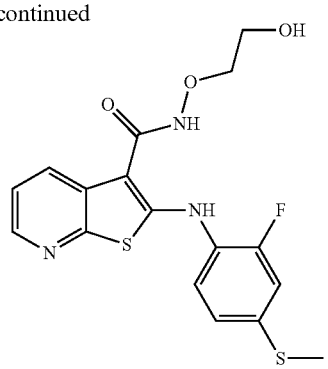

Step 1: (3-fluoro-4-isothiocyanatophenyl)(methyl)sulfane

Thiophosgene (5.48 g, 47.7 mmol) was added to a rapidly stirred mixture of 2-Fluoro-4-(methylsulphanyl)aniline (5.00 g, 31.8 mmol) in DCM (60 mL) and water (40 mL). The reaction mixture was stirred at room temperature overnight. The organic phase was separated, washed with saturated sodium bicarbonate solution, dried over sodium sulfate and filtered. The solvents were removed in vacuo to give the title compound as a yellow solid (5 g, 78.9%). $^1$HNMR (300 MHz, DMSO-d6): δ 7.41-7.31 (m, 2H), 7.09 (d, J=8.4 Hz, 1H), 2.49 (s, 3H).

Step 2: 2-(2-fluoro-4-(methylthio)phenylamino)thieno[2,3-b]pyridine-3-carboxylic Acid To a stirred solution of diisopropyl amine (1.65 mL, 11.7 mmol) in anhydrous THF (10 mL) cooled to −15° C. was added n-butyl lithium (2.5 M in hexanes, 4.80 mL, 12.0 mmol) slowly between −10° C. and 0° C. The resultant mixture was stirred at room temperature for 15 minutes before being cooled to 0° C. The solution of LDA thus formed was added to a rapidly stirred suspension of 2-(2-chloropyridin-3-yl)acetic acid (1.00 g, 5.8 mmol) in anhydrous THF (20 mL) at 0° C. Upon complete addition of the LDA solution the resultant bright yellow suspension was stirred at 0° C. for 15 minutes. A solution of (3-fluoro-4-isothiocyanatophenyl)(methyl)sulfane (1.63 g, 8.2 mmol) in anhydrous THF (10 mL) was then added to the reaction mixture and heated to 65° C. for 18 hours. The reaction mixture was cooled to room temperature and the volatiles removed in vacuo. The resultant brown gum was redissolved in THF, cooled to 0° C. and 10% aq acetic acid 10 mL added slowly. Acetonitrile (5 mL) was added slowly until a yellow solid developed, the solid was isolated by filtration and washed with ether and acetonitrile to give the title compound as a yellow solid (546 mg, 20%). LC/MS: [M+1] 335. $^1$HNMR (300 MHz, DMSO-d6): δ 8.34 (d, J=8.1 Hz, 1H), 7.85-8.20 (m, 1H), 7.61 (t, J=8.6 Hz, 1H), 7.39-7.30 (m, 2H), 7.21 (d, J=9.2 Hz, 1H), 2.52 (s, 3H).

Step 3: N-(2-(vinyloxy)ethoxy)-2-(2-fluoro-4-(methylthio)phenylamino)thieno[2,3-b]pyridine-3-carboxamide A vial was charged with 2-(2-fluoro-4-(methylthio)phenylamino)thieno[2,3-b]pyridine-3-carboxylic acid (0.100 g, 0.1 mmol), 0-(2-(vinyloxy)ethyl)hydroxylamine (25 mg, 0.2 mmol), HATU (0.085 g, 0.2 mmol) and diisopropyl ethyl amine (52 ul, 0.3 mmol) and DMF (4 mL). The reaction mixture was stirred at room temperature overnight. The reaction was quenched with water and extracted with ethyl acetate. The organics were washed with water, brine and dried over sodium sulfate. The solvents were evaporated to give a light yellow solid (88 mg) which was used without further purification. LC/MS: [M+1]420.0.

Step 4: 2-(2-fluoro-4-(methylthio)phenylamino)-N-(2-hydroxyethoxy)thieno[2,3-b]pyridine-3-carboxamide A microwave reaction vial was charged with N-(2-(vinyloxy)ethoxy)-2-(2-fluoro-4-(methylthio)phenylamino)thieno[2,3-b]pyridine-3-carboxamide (0.088 g), ethanol (2 mL), and 2N HCl (2 mL). The reaction mixture was stirred at room temperature for one hour. The reaction was quenched with water and adjusted to pH to 8-10, then extracted with ethyl acetate. The organics were washed with water, brine and dried over sodium sulfate. The solvents were evaporated. The residue was purified by flash chromatography (4 g silica, 0-5% MeOH/DCM). The product fractions were collected and the solvents were removed in vacuo. The residue was purified again by preparative TLC (5% MeOH/DCM) and dried to give a light yellow solid (12 mg, 24%). LC/MS: [M+1]: 394.19. $^1$HNMR (300 MHz, CDCl3): δ 10.70 (s, 1H), 8.37 (s, 1H), 8.33-7.84 (m, 1H), 7.88-7.81 (m, 1H), 7.52 (t, J=8.4 Hz, 1H), 7.32-7.25 (m, 1H), 7.12-7.06 (m, 1H), 4.15 (t, J=4.38 Hz, 2H), 3.85 (m, 2H), 2.46 (s, 3H).

Example 3: Synthesis of 2-((2-Fluoro-4-iodophenyl)amino)-N-(2-hydroxyethoxy)thieno[2,3-b]pyridine-3-carboxamide

Step 1: (2-Chloropyridin-3-yl)methanol

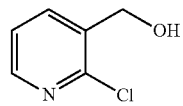

To a stirred solution of methyl 2-chloronicotinate (25 g, 145.71 mmol) in anhydrous THF (250 mL) at 0° C. under an atmosphere of nitrogen was added solid lithium aluminium hydride (11.06 g, 291.41 mmol) in small portions over a period of 20 min, maintaining the internal temperature below 5° C. The resulting grey suspension was heated to 50° C. for 2 h, before being allowed to cool to room temperature with stirring over 16 h. The reaction mixture was then cooled to 0° C. and quenched by the cautious addition of a saturated solution of aqueous sodium sulphate, resulting in the formation of a suspension. The mixture was passed through a pad of celite, and the pad was subsequently washed with ethyl acetate (2×50 mL). The combined filtrates were diluted with ethyl acetate (500 mL) and washed water (250 mL), before being dried over sodium sulphate, filtered and evaporated to dryness to give the crude product as a brown oil. Purification by silica gel chromatography eluting with a gradient of ethyl acetate (10 to 40%) in hexane afforded the desired compound as a pale brown solid (7.13 g, 34.1%). UPLC-MS (Acidic Method, 2 min): rt=0.60 min, m/z 144.0 [M+H]$^+$. $^1$H NMR (400 MHz, CDCl$_3$) δ ppm 8.28 (dd, J=4.77 Hz, 1.76 Hz, 1H), 7.93 (dt, J=7.59 Hz, 0.97 Hz, 0.97 Hz, 1H), 7.29 (dd, J=7.40 Hz, 5.14 Hz, 1H), 4.79 (s, 2H), 3.23 (br, s, 1H).

Step 2: (2-Chloropyridin-3-yl)methyl Methanesulfonate

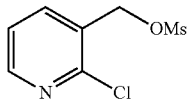

Methanesulfonyl chloride (7.70 mL, 99.380 mmol) was added dropwise to a stirred solution of (2-chloropyridin-3-yl)methanol (7.134 g, 49.960 mmol) and Et$_3$N (13.85 mL, 99.380 mmol) in dichloromethane (50 mL) at 0° C., taking care to maintain the internal temperature below 5° C. Upon completion of the addition, the reaction mixture was warmed to ambient temperature with stirring for 2 h. The reaction mixture was quenched with water (200 mL) and extracted with dichloromethane (2×200 mL). The combined organics were dried over Na$_2$SO$_4$, filtered and evaporated to dryness to afford the desired product as a brown oil (12.02 g, 100%). This material was taken in to the next step without any further purification. UPLC-MS (Acidic Method, 2 min): rt=0.79 min, in z 222.0 [M+H]$^+$. $^1$H NMR (400 MHz, CDCl$_3$) δ ppm 8.43-8.36 (m, 1H), 7.88-7.84 (m, 1H), 7.35-7.28 (m, 1H), 5.33 (s, 2H), 3.69 (s, 1H), 3.11 (s, 3H)

Step 3: 2-(2-Chloropyridin-3-yl)acetonitrile

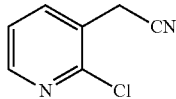

Sodium cyanide (7.98 g, 162.77 mmol) was added in a single portion to a solution of (2-chloropyridin-3-yl)methyl methanesulfonate (12.02 g, 54.24 mmol) in DMF (50 mL) at room temperature, and the resulting mixture was stirred at the same temperature for 2 h. The reaction was then poured into water (200 mL), and the resulting mixture was extracted with ethyl acetate (2×300 mL). The combined organics were dried over Na$_2$SO$_4$, filtered and evaporated to dryness to give the crude product, which was purified by column chromatography eluting with a gradient of ethyl acetate (10 to 30%) in hexane to afford the desired product as a pale brown solid (5.34 g, 64.5%). UPLC-MS (Acidic Method, 2 min): rt=0.73 min, m/z 153.0 [M+H]$^+$. $^1$H NMR (400 MHz, CDCl$_3$) δ 8.40 (dd, J=4.77 Hz, 1.76 Hz, 1H), 7.89 (ddt, J=7.62 Hz, 1.79 Hz, 0.82 Hz, 0.82 Hz, 1H), 7.34 (dd, J=7.53 Hz, 4.77 Hz, 1H), 3.87 (s, 2H).

Step 4: 2-(2-Chloropyridin-3-yl)acetic Acid

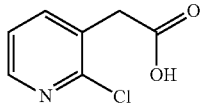

2-(2-Chloropyridin-3-yl)acetonitrile (5.34 g, 34.97 mmol) was dissolved in a 15% (w/w) aqueous NaOH solution (50 mL), and the resulting solution was stirred at ambient temperature for 60 min. The reaction was then acidified to pH=1 with concentrated hydrochloric acid, forming a beige precipitate, which was collected by filtration, washed with water (2×25 mL) and dried in an oven under vacuum at 40° C. to afford the desired product as a beige solid (5.57 g, 92.8%). UPLC-MS (Acidic Method, 2 min): rt=0.66 min, m/z 172.0 [M+H]$^+$. $^1$H NMR (400 MHz, DMSO-d6) δ ppm 12.64 (br, s, 1H), 8.33 (dd, J=4.77 Hz, 2.01 Hz, 1H), 7.86 (dd, J=7.53 Hz, 2.01 Hz, 1H), 7.41 (dd, J=7.53 Hz, 4.77 Hz, 1H), 3.76 (s, 2H).

Step 5: tert-Butyl 2-(2-chloropyridin-3-yl)acetate

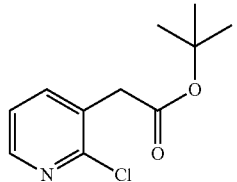

To a cooled solution of Ab/V-dicyclohexylcarbodiimide (7.36 g, 35.69 mmol,) in dichloromethane (120 mL) was added DMAP (3.17 g, 25.96 mmol) at 0° C., followed by 2-(2-chloropyridin-3-yl)acetic acid (5.57 g, 32.45 mmol), and the resulting mixture was stirred at 0° C. for 5 min. tert-Butanol (9.3 mL, 97.337 mmol) was then added to the reaction, and the resulting mixture was allowed to warm to room temperature with stirring for 12 h. The reaction was then evaporated to dryness to give a residue, which was dissolved in diethyl ether (400 mL). The ether solution was then filtered through a pad of celite, which was washed with diethyl ether (2×200 mL). The combined filtrates were washed sequentially with 1 M aqueous NaOH (300 mL), 2 N aqueous HCl (300 mL), water (300 mL) and brine (200 mL). The organic layer was then dried over Na$_2$SO$_4$, filtered and evaporated to dryness to give the crude product as a residue. Purification by flash column chromatography eluting with a gradient of ethyl acetate (5-20%) in hexane to afford the desired product as beige solid (5.25 g, 71.0%). UPLC-MS (Acidic Method, 2 min): rt=1.08 min, m/z 228.1 [M+H]$^+$. $^1$H NMR (400 MHz, CDCl$_3$) δ ppm 8.31 (dd, J=4.77 Hz, 2.01 Hz, 1H), 7.63 (dd, J=7.53 Hz, 2.01 Hz, 1H), 7.22 (dd, J=7.53 Hz, 4.77 Hz, 1H), 3.68 (s, 2H), 1.46 (s, 9H).

Step 6: tert-Butyl-2-((2-fluoro-4-iodophenyl)amino)thieno[2,3-b]pyridine-3-carboxylate

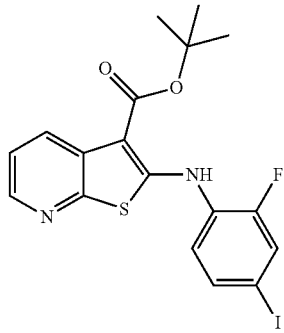 [SMILES: CC(C)(C)OC(=O)c1c(Nc2ccc(I)cc2F)sc2ncccc12]

To a solution of tert-butyl 2-(2-chloropyridin-3-yl)acetate (5.05 g, 22.16 mmol, 1 eq) in tetrahydrofuran (200 mL) was added sodium tert-butoxide (2.24 g, 23.27 mmol, 1.05 eq), and the resulting mixture was stirred at room temperature for 15 min. 2-Fluoro-4-iodo-1-isothiocyanatobenzene (6.18 g, 22.16 mmol, 1 eq) was then added to the reaction, and the resulting solution was stirred for 30 min. The mixture was then stirred at reflux for 16 h, before being cooled to room temperature and partitioned between ethyl acetate (300 mL) and water (300 mL). The aqueous layer was collected and extracted with ethyl acetate (300 mL), and the combined organics were dried over $Na_2SO_4$, filtered and concentrated. The crude material was purified by column chromatography eluting with dichloromethane to afford the desired product as a beige solid (8.49 g, 78.3%). UPLC-MS (Acidic Method, 2 min): rt=1.54 min, m/z 471.0 [M+H]$^+$. $^1$H NMR (400 MHz, CDCl$_3$) δ ppm 10.70 (br, s, 1H), 8.25 (q, J=1.67 Hz, 1H), 8.23 (s, 1H), 7.46-7.43 (m, 2H), 7.40-7.35 (m, 1H), 7.19 (dd, J=4.52 Hz, 3.01 Hz, 1H), 1.61 (s, 9H).

Step 7: 2-((2-Fluoro-4-iodophenyl)amino)thieno[2,3-b]pyridine-3-carboxylic Acid

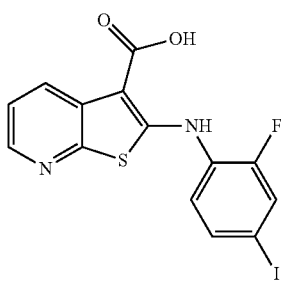 [SMILES: O=C(O)c1c(Nc2ccc(I)cc2F)sc2ncccc12]

A solution of tert-butyl 2-((2-fluoro-4-iodophenyl)amino)thieno[2,3-b]pyridine-3-carboxylate (1.00 g, 2.13 mmol) in dichloromethane (20 mL) was treated with 4 N HCl in dioxane (20 mL), and the resulting mixture was stirred at room temperature for 48 h. The solution was then concentrated to dryness to afford an oil, which was co-distilled with dichloromethane (2×25 mL) to afford the desired product as a yellow solid (1.04 g, 100%). UPLC-MS (Acidic Method, 2 min): rt=1.24 min, m/z 414.9 [M+H]$^+$. $^1$H NMR (400 MHz, DMSO-d$_6$) δ ppm 10.73 (s, 1H), 8.42 (dd, J=8.16 Hz, 1.63 Hz, 1H), 8.38 (dd, J=4.77 Hz, 1.51 Hz, 1H), 7.90 (dd, J=10.16 Hz, 1.88 Hz, 1H), 7.76-7.73 (m, 1H), 7.60 (t, J=8.53 Hz, 8.53 Hz, 1H), 7.48 (dd J=8.28 Hz, 4.77 Hz, 1H), 3.63 (s, 1H).

Step 8: 2-((2-Fluoro-4-iodophenyl)amino)-N-(2-hydroxyethoxy)thieno[2,3-b]pyridine-3-carboxamide

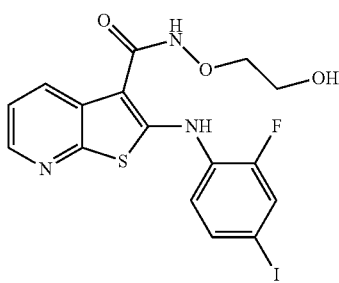 [SMILES: O=C(NOCCO)c1c(Nc2ccc(I)cc2F)sc2ncccc12]

To a stirred solution of 2-((2-fluoro-4-iodophenyl)amino)thieno[2,3-b]pyridine-3-carboxylic acid (1.5 g, 3.62 mmol, 1 eq), HATU (1.9 g, 5.07 mmol, 1.4 eq) and pyridine (0.59 mL, 7.24 mmol, 2 eq) in a mixture of DMF (15 mL) and DMSO (15 mL) was added 2-aminooxyethanol (0.56 g, 7.24 mmol, 2 eq), and the resulting mixture was stirred at room temperature for 16 h. The reaction was poured into water (100 mL), and the resulting mixture was extracted with ethyl acetate (3×50 mL). The combined organics were washed with brine (3×50 mL), dried over $Na_2SO_4$, filtered and concentrated to give the crude as a residue. Purification by prep-HPLC to afford the desired product (209 mg, 12%) as a pale yellow solid. UPLC-MS (Acidic Method, 2 min): rt 1.11 min, m/z 473.9 [M+H]$^+$. $^1$H NMR (400 MHz, DMSO-d$_6$) δ ppm 11.29 (br s, 1H), 10.36 (br s, 1H), 8.30-8.41 (m, 1H), 8.02-8.19 (m, 1H), 7.70-7.87 (m, 1H), 7.61 (d, J=8.7 Hz, 1H), 7.42 (br t, 0.7=8.7 Hz, 2H), 4.63-4.86 (m, 1H), 3.94 (br d, 0.7=4.4 Hz, 2H), 3.65 (br d, 0.7=4.6 Hz, 2H).

Example 4 Synthesis of (R)—N-(2,3-Dihydroxypropoxy)-2-((2-fluoro-4-iodophenyl)amino)thieno[2,3-b]pyridine-3-carboxamide Step 1: (R)—N-((2,2-Dimethyl-1,3-dioxolan-4-yl)methoxy)-2-((2-fluoro-4-iodophenyl)amino)thieno[2,3-b]pyridine-3-carboxamide

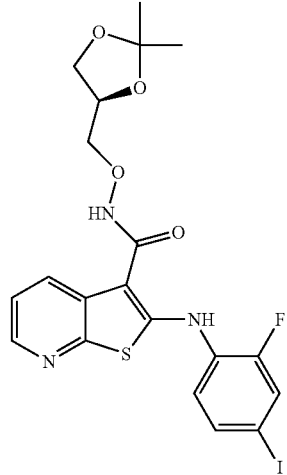 [SMILES: CC1(C)OC[C@H](CONC(=O)c2c(Nc3ccc(I)cc3F)sc3ncccc23)O1]

To a magnetically stirred mixture of 2-((2-fluoro-4-iodophenyl)amino)thieno[2,3-b]pyridine-3-carboxylic acid in DMF was added HATU and TEA, and the resulting mixture was agitated for 15 min. (R)—O-((2,2-Dimethyl-1,3-dioxolan-4-yl)methyl)hydroxylamine was then added to the reaction, and the resulting mixture was agitated at room temperature for 15 h. The reaction mixture was poured into water (30 mL), affording a yellow precipitate, which was collected by filtration. The resulting solid was washed with water (2×25 mL) and dried under vacuum at 40° C. to give the crude product as a yellow solid (0.27 g), which was used directly in the next step. UPLC-MS (Acidic Method, 2 min): rt 1.17 min, m/z 544.0 [M+H]$^+$

Step 2: (R)—N-(2,3-Dihydroxypropoxy)-2-((2-fluoro-4-iodophenyl)amino)thieno[2,3-b]pyridine-3-carboxamide

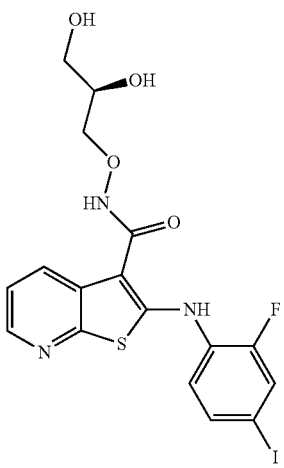 [SMILES: O=C(NOC[C@H](O)CO)c1c(Nc2ccc(I)cc2F)sc2ncccc12]

A solution of (R)—N-((2,2-dimethyl-1,3-dioxolan-4-yl)methoxy)-2-((2-fluoro-4-iodophenyl)amino)thieno[2,3-b]pyridine-3-carboxamide (270 mg, 0.50 mmol) in MeOH (10 mL) and ethylene glycol (140 L) was treated with p-toluene sulfonic acid monohydrate (41 mg, 0.21 mmol), and the resulting mixture was agitated for 15 h. The mixture was evaporated to dryness to give the crude product as a gum, which was purified by preparative HPLC, affording the desired product as an off-white solid (70 mg). UPLC-MS (Acidic Method, 2 min): rt 0.96 min, m/z 503.9 [M+H]$^+$. $^1$H NMR (400 MHz, DMSO-d6) δ ppm 10.94-11.70 (m, 1H), 10.06-10.79 (m, 1H), 8.29 (br s, 1H), 8.13 (br d, 0.7=4.39 Hz, 1H). 7.76 (br d, 0.7=10.04 Hz, 1H), 7.55-7.64 (m, 1H) 7.31-7.46 (m, 2H), 4.82-5.12 (m, 1H), 4.51-4.72 (m, 1H), 3.93-4.05 (m, 1H), 3.72-3.86 (m, 2H), 3.42 (br d, 0.7=4.77 Hz, 2H)

Example 5 2-((2-Fluoro-4-iodophenyl)amino)-N-(2-hydroxyethoxy)-6-methylthieno[2,3-b]pyridine-3-carboxamide

Step 1: 2-Chloro-6-methylpyridin-3-yl)methanol

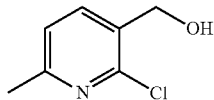

A cooled solution of methyl 2-chloro-6-methylpyridine-3-carboxylate (10 g, 53.88 mmol) in anhydrous tetrahydrofuran (120 mL) was treated with Lithium aluminium hydride (4.09 g, 107.75 mmol), which was added in a portion-wise over 20 min, taking care to maintain the internal temperature below 10° C. Upon completion of the addition, the reaction mixture was stirred at 50° C. for 12 h. The reaction was then chilled in an ice-water bath and quenched by the addition of a saturated aqueous solution of Na$_2$SO$_4$ (100 mL), resulting in the formation of a suspension, which was filtered through a pad of celite, washing with ethyl acetate (2×300 mL). The combined filtrate was evaporated to dryness to give a light orange oil, which was purified by column chromatography eluting with a gradient of ethyl acetate (0 to 40%) in hexane to afford the desired product as a pale yellow oil (5.5 g, 65%). UPLC-MS (Acidic Method, 2 min): rt=0.70 min, in z 158.0 [M+H]$^+$. $^1$H NMR (400 MHz, CDCl$_3$) δ ppm 7.74 (d, 0.7=7.7 Hz, 1H), 7.11 (d, J=7.8 Hz, 1H), 4.74 (s, 2H), 2.52 (s, 3H), 2.46 (br s, 1H)

Step 2: (2-Chloro-6-methylpyridin-3-yl)methyl Methanesulfonate

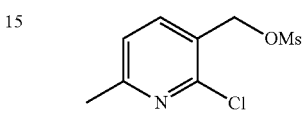

Methanesulfonyl chloride (5.4 mL, 69.8 mmol) was added dropwise to a solution of (2-chloro-6-methylpyridin-3-yl)methanol (5.5 g, 34.9 mmol) and Et$_3$N (9.7 mL, 69.8 mmol) in dichloromethane (52 mL) at 0° C., taking care to maintain the internal temperature below 5° C. Upon completion of the addition, the reaction mixture was allowed to warm to room temperature with stirring for 2 h, before being quenched with water (200 mL) and extracted with dichloromethane (2×250 mL). The combined organics were dried over Na$_2$SO$_4$, filtered and concentrated to afford the desired product as a brown oil (7.9 g, 96%), which was used directly in the next step without any further purification. UPLC-MS (Acidic Method, 2 min): rt=0.86 min, m/z 236.0 [M+H]$^+$. $^1$H NMR (400 MHz, CDCl$_3$) δ ppm 7.71 (t, J=1.5 Hz, 1H), 7.14 (dd, 0.7=7.7, 14.62 Hz, 1H), 5.29 (s, 1H), 4.65 (s, 1H), 3.03-3.16 (m, 3H), 2.54 (d, J=6.2 Hz, 3H)

Step 3: 2-(2-Chloro-6-methylpyridin-3-yl)acetonitrile

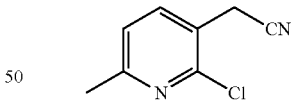

To a solution of (2-chloro-6-methylpyridin-3-yl)methyl methanesulfonate (7.9 g, 33.5 mmol) in DMF (48 mL) was added sodium cyanide (4.9 g, 100.5 mmol), and the resulting mixture was stirred for 2 h at room temperature. The reaction was then poured into water (250 mL), and the resulting mixture was extracted with ethyl acetate (3×250 mL). The combined organics were dried over Na$_2$SO$_4$, filtered and concentrated to afford the crude as a residue, which was purified by column chromatography eluting with a gradient of ethyl acetate (0 to 30%) in hexane to afford the desired product as a pale yellow solid (3.2 g, 58%). UPLC-MS (Acidic Method, 2 min): rt=0.84 min, m/z 167.0 [M+H]$^+$. $^1$H NMR (400 MHz, CDCl$_3$) δ ppm 7.76 (d, J=7.8 Hz, 1H), 7.17 (d, J=7.8 Hz, 1H), 3.82 (s, 2H), 2.56 (s, 3H)

Step 4: 2-(2-Chloro-6-methylpyridin-3-yl)acetic Acid

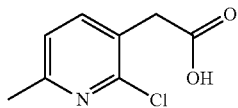

A stirred solution of 2-(2-chloro-6-methylpyridin-3-yl)acetonitrile (3.2 g, 19.2 mmol) in 15% (w/w) aqueous NaOH solution (32 mL) was heated at reflux for 30 min. The mixture was then cooled to room temperature and acidified to pH=1 with concentrated HCl, affording a beige precipitate, which was collected by filtration, washed with water (2×50 mL) and dried under vacuum to afford the desired product as a beige solid (3.2 g, 90%). UPLC-MS (Acidic Method, 2 min): rt=0.76 min, m/z 186.1 [M+H]$^+$. $^1$H NMR (400 MHz, CDCl$_3$) δ ppm 7.53 (d, J=1.1 Hz, 1H), 7.09 (d, J=1.1 Hz, 1H), 3.79 (s, 2H), 2.53 (s, 3H)

Step 5: tert-Butyl 2-(2-chloro-6-methylpyridin-3-yl)acetate

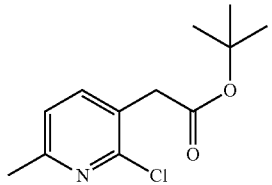 [SMILES: Cc1ccc(CC(=O)OC(C)(C)C)c(Cl)n1]

To a stirred solution of AC/V-dicyclohexylcarbodiimide (3.9 g, 18.92 mmol) in dichloromethane (72 mL) at 0° C. was added DMAP (1.7 g 13.76 mmol), followed by 2-(2-chloro-6-methylpyridin-3-yl)acetic acid (3.2 g, 17.2 mmol), and the resulting mixture was stirred at 0° C. for 5 min. tert-Butanol (4.9 mL, 51.6 mmol) was then added to the reaction, and the resulting mixture was allowed to warm to room temperature with stirring over 16 h. The reaction was then evaporated to dryness to give a residue, was dissolved in diethyl ether (400 mL) and passed through a pad of celite, washing with diethyl ether (2×200 mL). The combined filtrate was washed sequentially with 1 M aqueous NaOH (300 mL), 2 N aqueous HCl (300 mL), water (300 mL) and brine (200 mL). The organic layer was dried over Na$_2$SO$_4$, filtered and concentrated. The crude material was purified by column chromatography eluting with a gradient of ethyl acetate (0 to 30%) in hexane to afford the desired product as a pale yellow oil (3.03 g, 73%). UPLC-MS (Acidic Method, 2 min): rt 1.14 min, m/z 242.1 [M+H]$^+$. $^1$H NMR (400 MHz, CDCl$_3$) δ ppm 7.50 (d, J=7.7 Hz, 1H), 7.05 (d, J=7.7 Hz, 1H), 3.62 (s, 2H), 2.51 (s, 3H), 1.44 (s, 9H)

Step 6: tert-Butyl 2-((2-fluoro-4-iodophenyl)amino)-6-methylthieno[2,3-b]pyridine-3-carboxylate

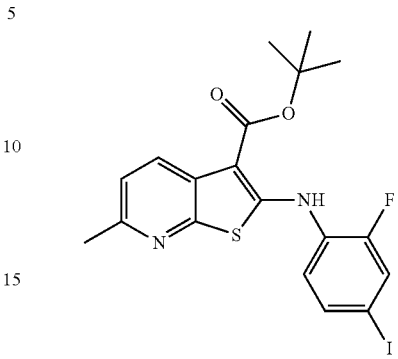

To a solution of tert-butyl 2-(2-chloro-6-methylpyridin-3-yl)acetate (3.03 g, 12.5 mmol) in tetrahydrofuran (250 mL) was added sodium tert-butoxide (1.26 g, 13.13 mmol) under nitrogen atmosphere. A yellow solution was formed which was stirred at room temperature for 15 min. Then 2-fluoro-4-iodo-1-isothiocyanatobenzene (3.5 g, 12.5 mmol) was added and the solution was stirred for 30 min. The solution turned light brown. Finally the mixture was stirred at reflux overnight. The reaction was cooled to room temperature and partitioned between ethyl acetate (300 mL) and water (300 mL). The organic phase was collected and the aqueous layer was extracted with ethyl acetate (300 mL). Combined organics were dried over Na$_2$SO$_4$, filtered and concentrated. The crude material was purified by column chromatography eluting with dichloromethane to afford the desired product as a yellow solid (2.5 g, 42%). UPLC-MS (Acidic Method, 2 min): rt=1.56 min, m/z 484.9 [M+H]$^+$. $^1$H NMR (400 MHz, CDCl$_3$) δ ppm 10.70 (br s, 1H), 8.21 (d, J=8.3 Hz, 1H), 7.49-7.54 (m, 2H), 7.42-7.48 (m, 1H), 7.13 (d, J=8.5 Hz, 1H), 2.59 (s, 3H), 1.68 (s, 9H)

Step 7: 2-((2-Fluoro-4-iodophenyl)amino)-6-methylthieno[2,3-b]pyridine-3-carboxylic Acid

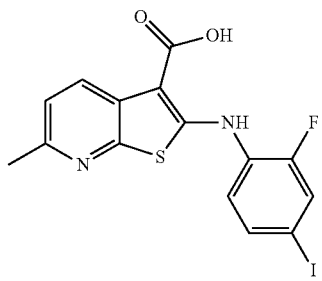 [SMILES: Cc1ccc2c(C(=O)O)c(Nc3ccc(I)cc3F)sc2n1]

To a solution of tert-butyl 2-((2-fluoro-4-iodophenyl)amino)-6-methylthieno[2,3-b]pyridine-3-carboxylate (0.26 g, 0.54 mmol) in dichloromethane (5.5 mL) was added trifluoroacetic acid (0.55 mL, 7.18 mmol), and the resulting mixture was stirred at room temperature for 4 h. The reaction mixture was then concentrated to afford a residue, which was co-distilled from toluene (3×50 mL) to afford the desired product as a yellow solid (0.24 g, 100%). UPLC-MS (Acidic Method, 4 min): rt=2.15 min, m/z 428.9 [M+H]$^+$. $^1$H NMR (400 MHz, DMSO-d$_6$) δ ppm 10.63 (s, 1H), 8.24 (d, J=8.3 Hz, 1H), 7.83 (dd, 0.7=1.9, 10.2 Hz, 1H), 7.65-7.70 (m, 1H), 7.52 (t, J=8.6 Hz, 1H), 7.28 (d, J=8.2 Hz, 1H)

Step 8: 2-((2-Fluoro-4-iodophenyl)amino)-N-(2-hydroxyethoxy)-6-methylthieno[2,3-b]pyridine-3-carboxamide

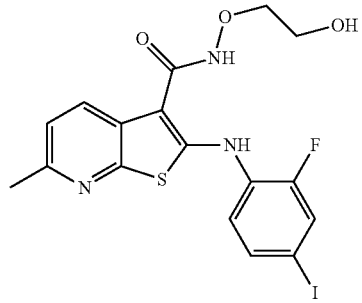 [SMILES: Cc1ccc2c(C(=O)NOCCO)c(Nc3ccc(I)cc3F)sc2n1]

To a solution of 2-((2-fluoro-4-iodophenyl)amino)-6-methylthieno[2,3-b]pyridine-3-carboxylic acid (0.24 g, 0.56 mmol) in anhydrous tetrahydrofuran (14 mL) was added PyBOP (0.41 mg, 0.78 mmol), followed by Et$_3$N (0.23 mL, 1.68 mmol), and the resulting solution was stirred at room temperature for 30 min. 2-(Aminooxy)ethan-1-ol (65 mg, 0.84 mmol) was then added to the reaction, and the resulting mixture was stirred at room temperature for 12 h. Water (50 mL) was added to the reaction, forming a biphasic mixture. The aqueous phase was collected and extracted with ethyl acetate (3×50 mL). The combined organics were washed with brine, dried over Na$_2$SO$_4$, filtered and concentrated. The crude material was purified by prep-HPLC to afford the desired product as a pale yellow solid (115 mg, 42%). UPLC-MS (Acidic Method, 4 min): rt=1.84 min, m/z 487.9 [M+H]$^+$. $^1$H NMR (400 MHz, DMSO-d$_6$) δ ppm 11.24 (brs, 1H), 10.11-10.38 (br s, 1H), 7.93-8.06 (m, 1H), 7.67-7.80 (m, 1H), 7.58 (br d, J=1.1 Hz, 1H), 7.36 (br t, J=8.6 Hz, 1H), 7.28 (br dd, 0.7=4.1, 7.2 Hz, 1H), 4.59-4.84 (br s, 1H), 3.92 (t, J=4.9 Hz, 3H), 3.63 (br d, J=3.8 Hz, 3H) Example 6 2-((2-fluoro-4-iodophenyl)amino)-N-(2-hydroxyethoxy)-6-methoxythieno[2,3-b]pyridine-3-carboxamide Step 1: (2-Chloro-6-methoxypyridin-3-yl)methanol

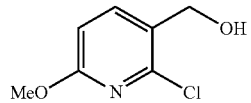

To a solution of methyl 2-chloro-6-methoxynicotinate (5.0 g, 24.8 mmol) in THF (50 mL) at 0° C. was added lithium aluminium hydride (1.88 g, 49.6 mmol) in a portion wise manner, taking care to keep the temperature below 10° C. Upon completion of the addition, the reaction mixture was stirred at 50° C. for 3 h. The reaction mixture was then cooled to 0° C., before being quenched by the careful addition of a saturated solution of aqueous sodium sulphate (50 mL). The resulting suspension was stirred for 20 min, before being filtered through a pad of celite, washing with ethyl acetate (2×50 mL). The combined organics were dried over anhydrous sodium sulphate, filtered and evaporated to dryness to give the desired product as a yellow-orange oil (3.82 g, 89%). UPLC-MS (Acidic Method, 2 mins): rt=0.83 min, m/z 174.0 [M+H]$^+$. $^1$H NMR (400 MHz, CDCl$_3$) δ ppm 7.69 (d, J=8.2 Hz, 1H) 6.69 (d, J=8.2 Hz, 1H) 4.70 (s, 2H) 3.88 (s, 3H)

Step 2: (2-Chloro-6-methoxypyridin-3-yl)methyl Methanesulfonate

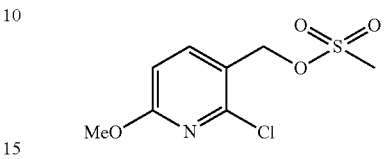

Methanesulfonyl chloride (3.4 mL, 44.0 mmol) was added to a stirred solution of (2-chloro-6-methoxypyridin-3-yl)methanol (3.82 g, 22.0 mmol) in dichloromethane (90 mL) at 0° C., and the resulting mixture was stirred at room temperature for 3 h. The reaction mixture was poured into water (100 mL), affording a biphasic solution. The organic phase was collected and the aqueous phase extracted with dichloromethane (2×50 mL). The combined organics were dried over anhydrous sodium sulfate, filtered and evaporated to dryness to give the desired product as an orange solid (4.26 g, 77%). UPLC-MS (Acidic Method, 2 mins): rt=1.13 min, m/z 252.1 [M+H]$^+$. $^1$H NMR (400 MHz, CDCl$_3$) δ ppm 7.65 (d, J=8.2 Hz, 1H) 6.69 (d, J=8.2 Hz, 1H) 4.64 (s, 2H) 3.94 (s, 3H) 3.14 (s, 3H)

Step 3: 2-(2-Chloro-6-methoxypyridin-3-yl)acetonitrile

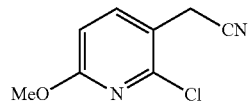

To a solution of (2-chloro-6-methoxypyridin-3-yl)methyl methanesulfonate (4.26 g, 16.9 mmol) in DMF (17 mL) was added sodium cyanide (2.48 g, 50.7 mmol) in a portion wise manner over 5 min, and the resulting mixture was stirred at room temperature for 24 h. The reaction was poured into water (100 mL), and the resulting mixture was extracted with ethyl acetate (3×50 mL). The combined organics were washed with brine (2×200 mL), dried over anhydrous sodium sulfate, filtered and evaporated to dryness. The crude was purified by flash column chromatography eluting with a gradient of methanol (0-5%) in DICHLOROMETHANE to give the desired product as a white solid (1.75 g, 57%). UPLC-MS (Acidic Method, 2 mins): rt 0.96 min, m/z 183.0 [M+H]$^+$. $^1$H NMR (400 MHz, CHCl$_3$) δ ppm 7.69 (d, J=8.2 Hz, 1H), 6.73 (d, J=8.2 Hz, 1H), 3.94 (s, 3H), 3.75 (s, 2H).

Step 4: 2-(2-Chloro-6-methoxypyridin-3-yl)acetic Acid

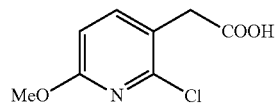

A suspension of 2-(2-chloro-6-methoxypyridin-3-yl)acetonitrile (1.75 g, 9.5 mmol) in an aqueous solution of 15% w/w NaOH (16 mL) was stirred at 60° C. for 24 h. The reaction mixture was then cooled to room temperature and acidified of pH=1 with concentrated hydrochloric acid. The resulting precipitate was collected by filtration and washed with water (2×20 mL), before being dried under vacuum at 40° C. to give the desired product as a white solid (1.50 g, 78%). UPLC-MS (Acidic Method, 2 mins): rt=0.84 min, m/z 202.0 [M+H]$^+$. $^1$H NMR (400 MHz, DMSO-r/e) δ ppm 12.51 (br s, 1H), 7.76 (d, J=8.2 Hz, 1H), 6.84 (d, J=8.2 Hz, 1H), 3.85 (s, 3H), 3.66 (s, 2H).

Step 5: tert-Butyl 2-(2-chloro-6-methoxypyridin-3-yl)acetate

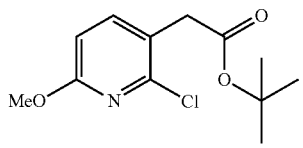 [SMILES: COc1ccc(CC(=O)OC(C)(C)C)c(Cl)n1]

To a suspension of 2-(2-chloro-6-methoxypyridin-3-yl)acetic acid (1.34 g, 6.65 mmol) in tert-butanol (15 mL) was added di-tert-butyl dicarbonate (2.3 mL, 9.97 mmol), followed by DMAP (0.082 g, 0.67 mmol), and the resulting mixture was stirred at 50° C. for 18 h. The reaction mixture was cooled to room temperature and evaporated to dryness to give a residue, which was diluted with water (20 mL) and extracted with ethyl acetate (2×20 mL). The combined organics were dried over anhydrous sodium sulfate, filtered and concentrated to give the crude, which was purified by flash column chromatography eluting with a gradient of ethyl acetate (20-80%) in hexane to give the desired product as a pale yellow oil (1.27 g, 69%). UPLC-MS (Acidic Method, 2 mins): rt=1.21 min, m/z 258.1 [M+H]$^+$. $^1$H NMR (400 MHz, CDCl$_3$) δ ppm 7.49 (d, J=8.2 Hz, 1H), 6.65 (d, J=8.2 Hz, 1H), 3.92 (s, 3H), 3.58 (s, 2H), 1.45 (s, 9H)

Step 6: tert-Butyl 2-((2-fluoro-4-iodophenyl)amino)-6-methoxythieno[2,3-b]pyridine-3-carboxylate

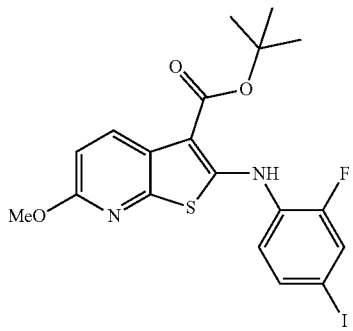 [SMILES: COc1ccc2c(C(=O)OC(C)(C)C)c(Nc3ccc(I)cc3F)sc2n1]

tert-Butyl 2-(2-chloro-6-methoxypyridin-3-yl)acetate (1.0 g, 3.88 mmol) and sodium tert-butoxide (0.41 g, 4.27 mmol) were added to a microwave vial, followed by THF (35 mL), and the resulting mixture was agitated for 5 min. A solution of 2-fluoro-4-iodo-1-isothiocyanatobenzene (1.11 g, 3.88 mmol) in THF (5 mL) was then added to the microwave vial, and the resulting mixture was stirred at room temperature for 1 h. Caesium fluoride (0.295 g, 1.94 mmol) was then added to the vial, and the reaction mixture was heated at 90° C. under microwave irradiation for 1 h. The mixture was cooled to room temperature and evaporated to dryness to afford the crude product, which was purified by flash column chromatography eluting with dichloromethane to give the desired product as a yellow solid (0.564 g, 30%). UPLC-MS (Acidic Method, 4 mins): rt=2.95 min, m/z 500.9 [M+H]$^+$. $^1$H NMR (400 MHz, CDCl$_3$) δ ppm 10.56 (s, 1H), 8.25 (d, J=8.8 Hz, 1H), 7.43-7.53 (m, 3H), 6.76 (d, 0.7=8.8 Hz, 1H), 3.96 (s, 3H), 1.78 (s, 9H)

Step 7: 2-((2-fluoro-4-iodophenyl)amino)-6-methoxythieno[2,3-b]pyridine-3-carboxylic Acid

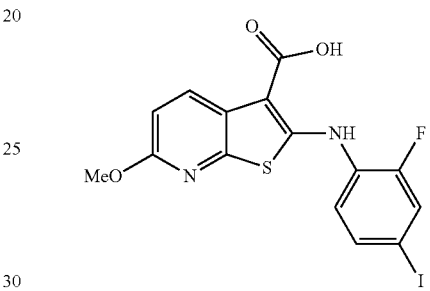

To a solution of tert-butyl 2-((2-fluoro-4-iodophenyl)amino)-6-methoxythieno[2,3-b]pyridine-3-carboxylate (0.050 g, 0.10 mmol) in dichloromethane (3 mL) was added trifluoroacetic acid (0.3 mL). The resultant mixture was stirred at room temperature under a N$_2$ atmosphere for 6h. The solvent was removed in vacuo and co-distilled with toluene (2×10 mL) to give the desired product as a yellow solid (0.44 g, 100%), which was used in the next step without further purification. UPLC-MS (Acidic Method, 2 mins): rt=1.35 min, m/z 445.0 [M+H]$^+$ Step 8: 2-((2-fluoro-4-iodophenyl)amino)-N-(2-hydroxyethoxy)-6-methoxythieno[2,3-b]pyridine-3-carboxamide

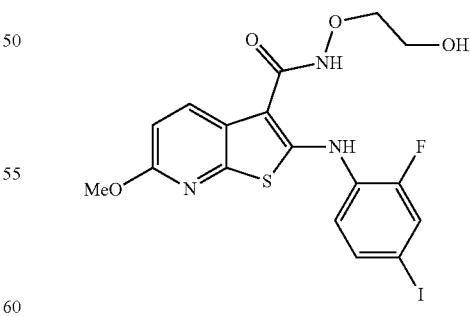

To a suspension of 2-((2-fluoro-4-iodophenyl)amino)-6-methoxythieno[2,3-b]pyridine-3-carboxylic acid (0.050 g, 0.11 mmol) in THF (2 mL) was added PyBOP (0.078 g, 0.15 mmol) and triethylamine (0.05 mL, 0.33 mmol). The resultant mixture was stirred at room temperature under a N$_2$ atmosphere for 30 min. A solution of 2-(aminooxy)ethanol (0.011 mL, 0.15 mmol) in THF (0.1 mL) was added and the reaction mixture was stirred at room temperature under a N₂ atmosphere for 1 h. The reaction mixture was diluted with water (10 mL) and then extracted with ethyl acetate (2×10 mL). The combined organics were dried over anhydrous sodium sulfate, filtered and evaporated to dryness to give the crude product, which was purified by preparatory HPLC to give the desired product as an off-white solid (0.023 g, 22%). UPLC-MS (Acidic Method, 4 mins): rt=2.10 min, m/z 503.9 [M+H]⁺. ¹H NMR (400 MHz, DMSO-d₆) δ ppm 11.30 (br s, 1H), 9.77 (br s, 1H), 8.11 (br s, 1H), 7.70 (br s, 1H), 7.53 (br d, J=8.2 Hz, 1H), 7.26 (br d, J=8.2 Hz, 1H), 6.91 (br d, J=7.0 Hz, 1H), 4.77 (br s, 1H), 3.90 (s, 3H), 3.89 (br s, 2H), 3.62 (br s, 2H)

Example 7: 2-((2-Fluoro-4-iodophenyl)amino)-N-(2-hydroxyethoxy)-5-methoxythieno[2,3-b]pyridine-3-carboxamide Step 1: (2-Chloro-5-methoxypyridin-3-yl)methanol

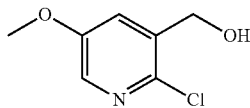

A solution of methyl 2-chloro-5-methoxynicotinate (0.5 g, 2.48 mmol) in anhydrous THF (5 mL) was cooled to 0° C. and treated with lithium aluminium hydride (0.19 g, 4.96 mmol) in a portion-wise manner. Upon completion of the addition, the mixture was heated to 50° C. for 1 h. The mixture was then cooled to 0° C. and treated with an aqueous solution of sodium sulphate, and the resulting mixture was stirred for 0.5 h at ambient temperature. The mixture was diluted with ethyl acetate (10 mL) and filtered through a pad of Celite. The pad was washed with ethyl acetate (2×20 mL) and the combined organic phases were dried over Na₂SO₄, filtered and concentrated under vacuum to give the crude product, which was purified by flash column chromatography eluting with a gradient of methanol (0-5%) in DICHLOROMETHANE to give the desired product as a brown oil (0.368 g, 86%). UPLC-MS (Acidic Method, 2 min): rt=0.72 min, m/z 174.0/175.9 [M+H]⁺. ¹H NMR (400 MHz, CDCl₃) δ ppm 7.97 (d, J=3.0 Hz, 1H), 7.47 (dt, 0.7=3.1, 0.8 Hz, 1H), 4.74 (s, 2H), 3.86 (s, 3H)

Step 2: (2-Chloro-5-methoxypyridin-3-yl)methyl Methanesulfonate

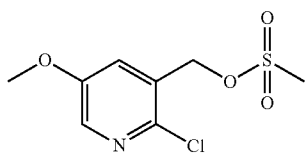

A solution of (2-chloro-5-methoxypyridin-3-yl)methanol (2.74 g, 15.84 mmol) in anhydrous dichloromethane (60 mL) was cooled to 0° C. and treated sequentially with triethylamine (4.42 mL, 31.67 mmol) methanesulfonyl chloride (2.45 mL, 31.67 mmol), and the resulting mixture was slowly warmed up to ambient temperature with stirring over 1 h. The mixture was diluted with water (30 mL) and extracted with DICHLOROMETHANE (2×30 mL). The combined organic phases were washed with brine (30 mL), dried over Na₂SO₄, filtered and concentrated under vacuum to afford the desired product as a brown oil (3.99 g, 100%). UPLC-MS (Acidic Method, 2 min): rt=0.87 min, m/z 252.0/254.0 [M+H]⁺ and 1.01 min, m/z 192.0/194.0 [M+H]⁺. ¹H NMR (400 MHz, CDCl₃) δ ppm 8.06-8.10 (m, 1H), 7.35-7.43 (m, 1H), 5.29 (s, 1H), 4.65 (s, 1H), 3.89 (s, 3H), 3.14 (s, 1H), 3.11 (s, 2H)

Step 3: 2-(2-Chloro-5-methoxypyridin-3-yl)acetonitrile

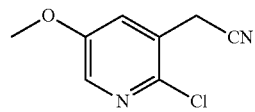

A solution of (2-Chloro-5-methoxypyridin-3-yl)methyl methanesulfonate (200 mg, 0. 80 mmol) in anhydrous DMF (1 mL) was treated with sodium cyanide (117 mg, 2.39 mmol), and the resulting mixture was stirred at ambient temperature for 1 h. The mixture was diluted with water (5 mL) and extracted with ethyl acetate (3×5 mL). The combined organic phases were washed sequentially with water (5 mL) and brine (5 mL), before being dried over Na₂SO₄, filtered and concentrated under vacuum to give the crude product, which was purified by flash column chromatography eluting with a gradient of methanol (0-4%) in dichloromethane to give the desired product as a yellow solid (89 mg, 61%). UPLC-MS (Acidic Method, 2 min): rt=0.86 min, m/z 183.0/185.0 [M+H]⁺. ¹H NMR (400 MHz, CDCl₃) δ ppm 8.07 (d, J=2.9 Hz, 1H), 7.41-7.44 (m, 1H), 3.90 (s, 3H), 3.84 (s, 2H)

Step 4: 2-(2-Chloro-5-methoxypyridin-3-yl)acetic Acid

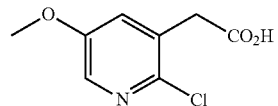

A suspension of 2-(2-chloro-5-methoxypyridin-3-yl)acetonitrile (1.19 g, 6.55 mmol) in a 15% (w/v) solution of aqueous sodium hydroxide (11.9 mL) was heated at 100° C. with stirring for 2 h, resulting in a clear solution. The reaction mixture was then cooled to 5° C. (ice bath) and cautiously treated with a 1 M solution of aqueous hydrogen chloride until the solution was acidic (pH=1), leading to a formation of an off-white precipitate. The solid was collected by filtration and washed with water until the filtrate became pH neutral. The solid was then dried under vacuum to give the desired product as a beige solid (1.18 g, 89%). UPLC-MS (Acidic Method, 2 min): rt=0.78 min, m/z 202.1/204.0 [M+H]⁺. ¹H NMR (400 MHz, DMSO-d₆) δ ppm 8.03 (d, J=3.0 Hz, 1H), 7.52 (d, J=3.0 Hz, 1H), 3.82 (s, 3H), 3.69 (s, 2H)

Step 5: tert-Butyl 2-(2-chloro-5-methoxypyridin-3-yl)acetate

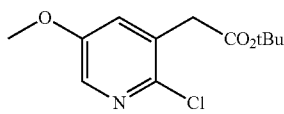 [SMILES: COc1cnc(Cl)c(CC(=O)OC(C)(C)C)c1]

A suspension of 2-(2-chloro-5-methoxypyridin-3-yl)acetic acid (980 mg, 4.80 mmol) in tert-butanol (10.9 mL) was treated sequentially with di-tert-butyl dicarbonate (1.67 mL, 7.28 mmol) and 4-dimethylaminopyridine (59 mg, 0.48 mmol), and the resulting mixture was heated at 50° C. for 2 h. The mixture was cooled down to ambient temperature and concentrated under vacuum to give a residue, which was dissolved in ethyl acetate (20 mL). The solution was washed with water (20 mL) and the aqueous phase was extracted with ethyl acetate (120 mL). The combined organic layers were dried over $Na_2SO_4$, filtered and concentrated under vacuum to give the crude product as an oil, which was purified by flash column chromatography eluting with a gradient of ethyl acetate (0-15%) in hexanes to afford the desired product as a yellow oil (990 mg, 79%). UPLC-MS (Acidic Method, 2 min): rt=1.16 min, m/z 258.1/260.1 $[M+H]^+$. $^1H$ NMR (400 MHz, $CDCl_3$) δ ppm 8.01 (d, J=3.0 Hz, 1H), 7.21 (d, J=3.0 Hz, 1H), 3.88 (s, 3H), 3.66 (s, 2H), 1.48 (s, 9H)

Step 6: tert-Butyl 2-((2-fluoro-4-iodophenyl)amino)-5-methoxythieno[2,3-b]pyridine-3-carboxylate

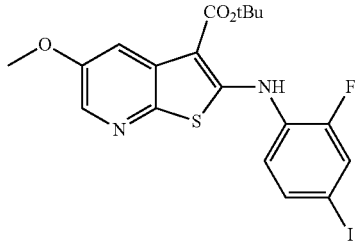 [SMILES: COc1cnc2sc(Nc3ccc(I)cc3F)c(C(=O)OC(C)(C)C)c2c1]

A solution of tert-butyl 2-(2-chloro-5-methoxypyridin-3-yl)acetate (50 mg, 0.194 mmol) in anhydrous THF (2 mL) was treated with sodium tert-butoxide (20 mg, 0.213 mmol), and the resulting mixture was stirred at ambient temperature for 5 min. A solution of 2-fluoro-4-iodo-1-isothiocyanatobenzene (54 mg, 0.194 mmol) in anhydrous THF (0.5 mL) was then added to the reaction, and the resulting mixture was stirred at ambient temperature for 1.5 h, before being heated under microwave irradiation at 90° C. for 2 h. The mixture was cooled to ambient temperature and concentrated under vacuum to give the crude product as an oil, which and purified by flash column chromatography (Silica 12 g, 0-7% ethyl acetate in hexanes), followed by the trituration of the resulting solid with hexanes to afford the desired product as a pale yellow solid (33 mg, 34%). UPLC-MS (Acidic Method, 4 min): rt=2.84 min, m/z 500.9 $[M+H]^+$. $^1H$ NMR (400 MHz, $CDCl_3$) δ ppm 10.79 (br s, 1H), 8.08 (d, J=2.9 Hz, 1H), 7.93 (d, J=2.8 Hz, 1H), 7.45-7.56 (m, 3H), 3.90 (s, 3H), 1.71 (s, 9H)

Step 7: 2-((2-Fluoro-4-iodophenyl)amino)-5-methoxythieno[2,3-b]pyridine-3-carboxylic Acid

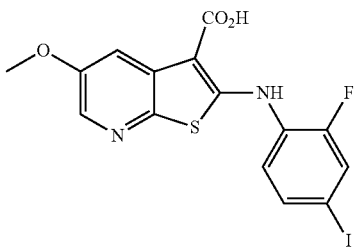 [SMILES: COc1cnc2sc(Nc3ccc(I)cc3F)c(C(=O)O)c2c1]

A solution of tert-butyl 2-((2-fluoro-4-iodophenyl)amino)-5-methoxythieno[2,3-b]pyridine-3-carboxylate (385 mg, 0.77 mmol) in dichloromethane (25 mL) was treated with trifluoroacetic acid (2.5 mL), and the resulting mixture was stirred at ambient temperature for 18 h. The mixture was then concentrated under vacuum to giver an oil, which was co-distilled from toluene (2×20 mL) to afford the desired product as yellow solid (342 mg, 100%). UPLC-MS (Acidic Method, 4 min): rt=2.14 min, m/z 443.0 $[M-H]^{-1}$. $^1H$ NMR (400 MHz, DMSO-$d_6$) δ ppm 10.69 (s, 1H), 8.06 (d, J=2.8 Hz, 1H), 7.88 (d, J=2.8 Hz, 1H), 7.82 (dd, J=10.2, 1.9 Hz, 1H), 7.65 (d, J=8.7 Hz, 1H), 7.51 (t, J=8.6 Hz, 1H), 3.85 (s, 3H).

Step 8: 2-((2-Fluoro-4-iodophenyl)amino)-N-(2-hydroxyethoxy)-5-methoxythieno[2,3-b]pyridine-3-carboxamide

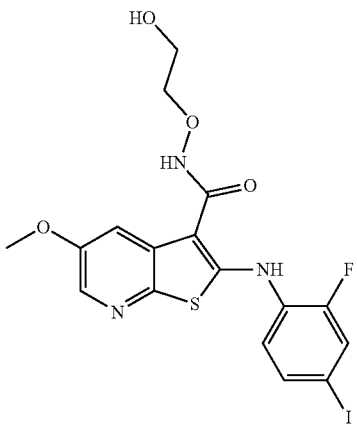 [SMILES: COc1cnc2sc(Nc3ccc(I)cc3F)c(C(=O)NOCCO)c2c1]

A suspension of 2-((2-fluoro-4-iodophenyl)amino)-5-methoxythieno[2,3-b]pyridine-3-carboxylic acid (342 mg, 0.77 mmol) in THF (15 mL) was treated sequentially with PyBOP (546 mg, 1.05 mmol) and triethylamine (0.32 mL, 2.31), and the resulting mixture was stirred at ambient temperature for 0.5 h. (2-Aminooxy)ethanol (81 mg, 1.05 mmol) was added to the reaction, and the resulting mixture was stirred at ambient temperature for 18 h. The mixture was then diluted with ethyl acetate (10 mL), washed with water (2×10 mL), dried over $Na_2SO_4$, filtered and concentrated to give the crude product, which was purified by preparatory HPLC to give the desired product as a yellow solid (131 mg, 34%). UPLC-MS (Acidic Method, 4 min): rt=1.85 min, in z 503.9 $[M+H]^+$. $^1H$ NMR (400 MHz, DMSO-$d_6$) δ ppm 11.29 (s, 1H), 10.43 (br s, 1H), 8.09 (br s, 1H), 7.77 (br d, 0.7=10.3 Hz, 1H) 7.57-7.64 (m, 2H), 7.41 (t, J=8.6 Hz, 1H), 4.78 (br s, 1H), 3.85-3.96 (m, 5H) 3.68-3.61 (m, 2H)

Example 8: 2-((2-Fluoro-4-iodophenyl)amino)-N-(2-hydroxyethoxy)-5-fluorothieno[2,3-b]pyridine-3-carboxamide Step 1: (2-Chloro-5-fluoropyridin-3-yl)methanol

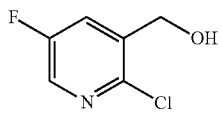

A solution of methyl 2-chloro-5-fluoronicotinate (100 mg, 0.53 mmol) in anhydrous THF (4 mL) was cooled to 0° C. and treated with sodium borohydride (120 mg, 3.17 mmol) in a portion-wise manner over a period of 5 min, and the resulting mixture was heated at 70° C. for 15 min. Methanol (0.8 mL) was then added in a dropwise manner over 15 min, resulting in considerable effervescence, and the resulting mixture was heated at 70° C. for 30 min. The mixture was cooled to ambient temperature and treated with a saturated solution of aqueous ammonium chloride (5 mL). Ethyl acetate (5 mL) was added, resulting in a biphasic mixture, which stirred for 30 min. The organic phase was collected and the aqueous layer was extracted with ethyl acetate (2×5 mL). The combined organic phases were then dried over $Na_2SO_4$, filtered and concentrated under vacuum to give the desired product as an orange glass (84 mg, 99%). UPLC-MS (Acidic Method, 2 min): rt=0.73 min, m/z 162.0/164.0 [M+H]$^+$. $^1$HNMR (400 MHz, CDCl$_3$) δ ppm 8.17 (d, 0.7=3.0 Hz, 1H), 7.71 (ddt, 0.7=8.3, 3.0, 0.9, 0.9 Hz, 1H), 4.78 (s, 2H).

Step 2: (2-Chloro-5-fluoropyridin-3-yl)methyl Methanesulfonate

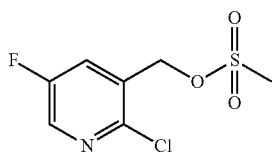

A solution of (2-chloro-5-fluoropyridin-3-yl)methanol (225 mg, 1.39 mmol) in anhydrous dichloromethane (5 mL) was cooled to 0° C. and treated with triethylamine (0.39 mL, 2.78 mmol) followed by methanesulfonyl chloride (0.22 mL, 2.78 mmol). The resulting mixture was then gradually warmed up to ambient temperature and stirred for 1 h. The mixture was diluted with water (5 mL) and extracted with dichloromethane (2×5 mL). The combined organic phases were washed with brine (5 mL), dried over $Na_2SO_4$, filtered and concentrated under vacuum to afford the desired product as a brown oil (335 mg, 100%). UPLC-MS (Acidic Method, 2 min): rt=0.88 min, m/z 240.1/242.0 [M+H]$^+$ and 1.03 min, m/z 223.2 [M+H]$^+$. $^1$HNMR (400 MHz, CDCl$_3$) δ ppm 8.24-8.30 (m, 1H), 7.62-7.68 (m, 1H), 5.29 (s, 1H), 4.65 (s, 1H), 3.15 (s, 3H).

Step 3: 2-(2-Chloro-5-fluoropyridin-3-yl)acetonitrile

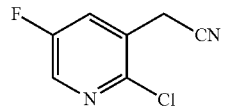

A solution of (2-chloro-5-fluoropyridin-3-yl)methyl methanesulfonate (4.93 g, 20.6 mmol) in anhydrous DMF (20.6 mL) was treated with sodium cyanide (3.0 g, 61.7 mmol), and the resulting mixture was stirred at ambient temperature for 4 h. The mixture was diluted with water (50 mL) and extracted with ethyl acetate (3×50 mL). The combined organic phases were washed sequentially with H$_2$O (50 mL) and brine (50 mL), before being dried over Na$_2$SO$_4$, filtered and concentrated under vacuum to give the crude product, which was purified by flash column chromatography eluting with a gradient of dichloromethane (0-80%) in hexanes to give the desired product as a light brown oil (1.38 g, 39%). UPLC-MS (Acidic Method, 2 min): rt=0.84 min, m/z 171.1/173.1 [M+H]$^+$. $^1$H NMR (400 MHz, CDCl$_3$) δ ppm 8.30 (d, J=2.9 Hz, 1H), 7.70 (ddt, 0.7=7.8, 2.9, 0.8, 0.8 Hz, 1H), 3.88 (t, J=0.6 Hz, 2H).

Step 4: 2-(2-Chloro-5-fluoropyridin-3-yl)acetic Acid

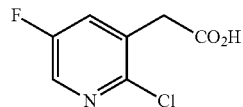

A suspension of 2-(2-chloro-5-fluoropyridin-3-yl)acetonitrile (1.38 g, 8.09 mmol) in a 15% (w/v) aqueous solution of sodium hydroxide (13.8 mL) was heated at 100° C. with stirring for 0.5 h, resulting in a clear solution. The reaction mixture was then cooled to 5° C. (ice bath) and cautiously treated with a 1 M solution of aqueous hydrogen chloride until the solution was acidic (pH=1), leading to a formation of an off-white precipitate. The solid was collected by filtration and washed with H$_2$O until the filtrate became pH neutral. The solid was then dried under vacuum to give the desired product as an off-white solid (1.22 g, 80%). UPLC-MS (Acidic Method, 2 min): rt=0.75 min, m/z 190.0/192.00 [M+H]$^+$. $^1$H NMR (400 MHz, DMSO-d$_6$) δ ppm 12.73 (br s, 1H), 8.38 (d, J=3.0 Hz, 1H), 7.91 (dd, 0.7=8.8, 3.0 Hz, 1H), 3.76 (s, 2H).

Step 5: tert-Butyl 2-(2-chloro-5-fluoropyridin-3-yl)acetate

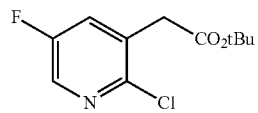 [SMILES: CC(C)(C)OC(=O)Cc1cc(F)cnc1Cl]

A suspension of 2-(2-chloro-5-fluoropyridin-3-yl)acetic acid (1.22 g, 6.43 mmol) in tert-butanol (17 mL) was treated sequentially with di-tert-butyl dicarbonate (2.22 mL, 9.65 mmol) and 4-dimethylaminopyridine (82 mg, 0.643 mmol), and the resulting mixture was heated at 50° C. with stirring for 1.5 h. The mixture was then cooled down to ambient temperature and concentrated under vacuum to give a residue, which was dissolved in ethyl acetate (20 mL). The resulting solution was washed sequentially with water (20 mL) and brine (20 mL), before being dried over $Na_2SO_4$, filtered and concentrated under vacuum to give the crude product as an oil, which was purified by flash column chromatography eluting with a gradient of ethyl acetate (0-10%) in hexanes to give the desired product as a pale yellow oil (1.25 g, 79%). UPLC-MS (Acidic Method, 2 min): rt=1.16 min, m/z 246.1/248.1 [M+H]+. 1H NMR (400 MHz, $CDCl_3$) δ ppm 8.20 (d, J=3.0 Hz, 1H), 7.45 (dd, J=8.0, 2.9 Hz, 1H), 3.69 (s, 2H), 1.47 (s, 9H).

Step 6: tert-Butyl 2-((2-fluoro-4-iodophenyl)amino)-5-fluorothieno[2,3-b]pyridine-3-carboxylate

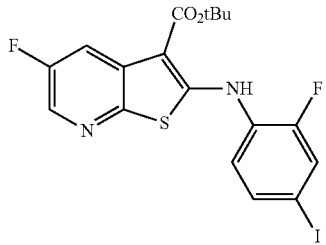 [SMILES: CC(C)(C)OC(=O)c1c(Nc2ccc(I)cc2F)sc2ncc(F)cc12]

A solution of tert-butyl 2-(2-chloro-5-fluoropyridin-3-yl)acetate (1.15 g, 4.68 mmol) in anhydrous THF (34 mL) was treated with sodium tert-butoxide (0.49 g, 5.148 mmol), and the resulting mixture was stirred at ambient temperature for 10 min. A solution of 2-fluoro-4-iodo-1-isothiocyanatobenzene (1.31 g, 4.68 mmol) in anhydrous THF (6 mL) was then added to the reaction, and the resulting mixture was stirred at ambient temperature for 1.5 h, before being heated under microwave irradiation at 90° C. for 2 h. The mixture was cooled to ambient temperature and concentrated under vacuum to give an oil, which was purified by flash column chromatography eluting with a gradient of ethyl acetate (0-5%) in hexanes to afford the desired product as a white solid (1.39 g, 56%). UPLC-MS (Acidic Method, 2 min): rt=1.63 min, m/z 489.0 [M+H]+. 1H NMR (400 MHz, DMSO-$d_6$) δ ppm 10.44 (s, 1H), 8.34 (dd, 0.7=2.8, 0.8 Hz, 1H), 7.95 (dd, J=10.6, 2.8 Hz, 1H), 7.85 (dd, J=10.0, 1.9 Hz, 1H), 7.67 (d, J=8.5 Hz, 1H), 7.50 (t, J=8.5 Hz, 1H), 1.64 (s, 9H).

Step 7: 2-((2-Fluoro-4-iodophenyl)amino)-5-fluoro-thieno[2,3-b]pyridine-3-carboxylic Acid

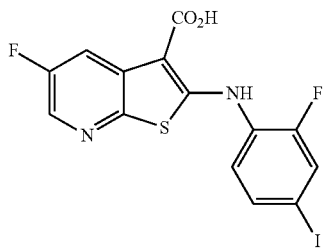

A solution of tert-butyl 2-((2-fluoro-4-iodophenyl)amino)-5-fluorothieno[2,3-b]pyridine-3-carboxylate (1.39 g, 2.85 mmol) in dichloromethane (80 mL) was treated with trifluoroacetic acid (8 mL), and the resulting mixture was stirred at ambient temperature for 18 h. The mixture was then concentrated under vacuum to give an oil, which was co-distilled from toluene (2×20 mL) to afford the desired product as a pale yellow solid (1.22 g, 99%). UPLC-MS (Acidic Method, 2 min): rt=1.30 min, m/z 431.0 [M−H]−. 1H NMR (400 MHz, DMSO-$d_6$) δ ppm 10.64 (s, 1H), 8.33 (dd, J=2.7, 0.7 Hz, 1H), 8.07 (dd, 0.7=10.42, 2.76 Hz, 1H), 7.85 (dd, 0.7=10.1, 1.8 Hz, 5H), 7.68 (dt, 0.7=8.5, 1.0 Hz, 1H), 7.51 (t, 0.7=8.5 Hz, 1H).

Step 8: 2-((2-Fluoro-4-iodophenyl)amino)-N-(2-hydroxyethoxy)-5-fluorothieno[2,3-b]pyridine-3-carboxamide

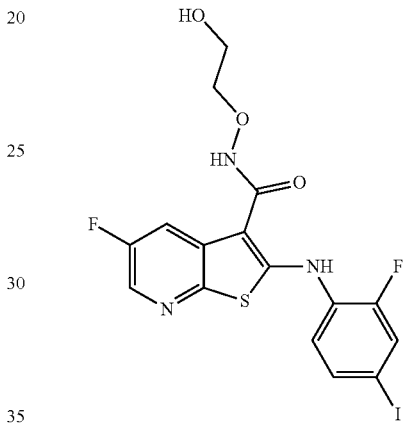

A suspension of 2-((2-fluoro-4-iodophenyl)amino)-5-fluorothieno[2,3-b]pyridine-3-carboxylic acid (500 mg, 1.16 mmol) in THF (20 mL) was treated sequentially with PyBOP (822 mg, 1.58 mmol) and triethylamine (0.49 mL, 3.48 mmol), and the resulting mixture was stirred at ambient temperature for 0.5 h. (2-Aminooxy)ethanol (122 mg, 1.58 mmol) was then added to the reaction, and the resulting mixture was stirred at ambient temperature for 18 h. The mixture was diluted with ethyl acetate (10 mL), washed with water (2×10 mL), dried over $Na_2SO_4$, filtered and concentrated under vacuum to give the crude product, which was purified by preparatory HPLC to give the desired product as a light yellow solid (115 mg, 20%). UPLC-MS (Acidic Method, 2 min): rt=1.19 min, m/z 491.9 [M+H]+. 1H NMR (400 MHz, DMSO-$d_6$) δ ppm 11.33 (s, 1H), 10.48 (s, 1H), 8.36 (s, 1H), 7.90 (d, J=9.9 Hz, 1H), 7.81 (dd, J=10.2, 1.8 Hz, 1H), 7.62 (d, J=8.4 Hz, 1H), 7.43 (t, J=8.5 Hz, 1H), 4.81 (br s, 1H), 3.95 (br t, J=4.7 Hz, 2H), 3.64 (br d, 0.7=4.3 Hz. 2H).

Biological Example 1a

MEK Inhibition Assay

MEK1 inhibitory activity of compounds were tested using the following procedure. (See Anastassiadis T, et al. *Comprehensive assay of kinase catalytic activity reveals features of kinase inhibitor selectivity. Nat Biotechnol.* 2011, 29(11), 1039-45.)

Reagents:
  Reaction buffer: 20 mM Hepes (pH 7.5), 10 mM MgCl$_2$, 1 mM EGTA, 0.02% Brij35, 0.02 mg/mL bovine serum albumin, 0.1 mM Na$_3$V04, 2 mM DTT, 1% DMSO
  Enzyme: MEK1, Invitrogen cat #PV3303
  N-terminal His-tagged recombinant human full length protein, expressed in insect cells. Activated in vitro by RAF1. MW=49.2 kDa, GenBank Accession No. NP_002746.
  Substrate: 5 µM ERK2 (K52R),
  Kinase-dead mutant, (GenBank Accession No. NM_0011949), aa2-358 with N-terminal His6 tag, MW=43.63 kDa, expressed in E. coli.

The substrate was prepared in freshly prepared Reaction Buffer. The kinase was delivered into the substrate solution and gently mixed. Test compounds were delivered in 100% DMSO into the kinase reaction mixture by Acoustic technology (Echo550; nanoliter range), and incubated for 20 min at room temperature. $^{33}$P-ATP was delivered into the reaction mixture to initiate the reaction. The reaction mixture was incubated for 2 hours at room temperature. Kinase activity was detected by P81 filter-binding method.

Biological Example 1b

MEK Inhibition Assay

MEK1 inhibitory activity of compounds were tested using the following procedure (protocol available at thermofisher.com/content/dam/LifeTech/migration/files/drug-discovery/pdfs.par.60256.file.dat/20130430%20ssbk%20customer%20protocol%20and%20assay%20conditions.pdf). The Z'-LYTE biochemical assay (ThermoFisher) employs a fluorescence-based, coupled-enzyme format and is based on the differential sensitivity of phosphorylated and non-phosphorylated peptides to proteolytic cleavage.

Test compounds in 100% DMSO were screened in 1% DMSO (final) in the well. For 10 point titrations, 3-fold serial dilutions are conducted from the starting concentration of 30 µM.

The peptide/kinase, MAP2K1 (MEK1)/inactive MAPK1 (ERK2)/Ser/Thr 03, mixture ("Peptide/kinase Mixture") was diluted to a 2× working concentration in the following buffer ("Kinase Buffer"): 50 mM HEPES pH 7.5, 0.01% BRIJ-35, 10 mM MgCl2, 1 mM EGTA. The final 10 µL kinase reaction consisted of 0.06-0.25 ng MAP2K1 (MEK1), 105 ng inactive MAPK1 (ERK2), and 2 µM Ser/Thr 03 in 50 mM HEPES pH 7.5, 0.01% BRIJ-35, 10 mM MgCl$_2$, 1 mM EGTA. After the 1 hour incubation, 5 µL of a 1:1024 dilution of Development Reagent A (available from Invitrogen, catalog no. PV3295) was added.

ATP solutions were diluted to a 4× working concentration in Kinase Buffer (50 mM HEPES pH 7.5, 0.01% BRIJ-35, 10 mM MgCl2, 1 mM EGTA). ATP Km apparent was previously determined using a Z'-LYTE assay. The Development Reagent was diluted in Development Buffer (available from Invitrogen, catalog no. P3127).

Assay Protocol: 2.5 µL of 4× test compound or 100 nL of 100× Test Compound plus 2.4 µL Kinase Buffer, 5 µL of the 2× Peptide/Kinase Mixture, 2.5 µL of 4×ATP Solution were added to the plates and placed on a shake plate for 30-seconds. The kinase reaction was allowed to proceed for 60-minute at room temperature, before 5 µL of Development Reagent Solution was added, and the mixture agitated for 30-seconds on a shake plate. The mixture was incubated for 60-minute at room temperature. Fluorescence was measured using a plate reader and the data were analyzed.

The maximum emission ratio was established by the 0% Phosphorylation Control (100% Inhibition Control), which contained no ATP and therefore exhibited no kinase activity. This control yielded 100% cleaved peptide in the Development Reaction. The 100% Phosphorylation Control, which consisted of a synthetically phosphorylated peptide of the same sequence as the peptide substrate, was designed to allow for the calculation of percent phosphorylation. This control yielded a very low percentage of cleaved peptide in the Development Reaction. The 0% Phosphorylation and 100% Phosphorylation Controls allow for the calculation of the percent phosphorylation achieved in a specific reaction well. Control wells did not include any kinase inhibitors.

The minimum emission ratio in a screen was established by the 0% Inhibition Control, which contained active kinase. This control was designed to produce a 10-50% phosphorylated peptide in the Kinase Reaction. Cascade assays may produce up to 70% phosphorylated peptide.

A known inhibitor control standard curve, 10 point titration, was run for each individual kinase on the same plate as the kinase to ensure the kinase was inhibited within an expected IC$_{50}$ range previously determined.

The following controls are prepared for each concentration of Test Compound assayed. The Development Reaction Interference was established by comparing the Test Compound Control wells that did not contain ATP versus the 0% Phosphorylation Control (which did not contain the Test Compound). The expected value for a non-interfering compound should be 100%. Any value outside of 90% to 110% was flagged. The Test Compound Fluorescence Interference was determined by comparing the Test Compound Control wells that did not contain the Kinase/Peptide Mixture (zero peptide control) versus the 0% Inhibition Control. The expected value for a non-fluorescence compound should be 0%. Any value >20% was flagged.

The data in Table A was calculated. XLfit from IDBS was used. The dose response curve was curve fit to model number 205 (sigmoidal dose-response model). If the bottom of the curve did not fit between −20% & 20% inhibition, it was set to 0% inhibition. If the top of the curve did not fit between 70% and 130% inhibition, it was set to 100% inhibition.

TABLE A

| | Equation |
|---|---|
| Correction for Background Fluorescence | $FI_{Sample} - FI_{TCFI\ Crl}$ |
| Emission Ratio (using values corrected for background fluorescence) | $\dfrac{\text{Coumarin Emission (445 nm)}}{\text{Fluorescein Emission (520 nm)}}$ |
| % Phosphorylation (% Phos) | $\left\{1 - \dfrac{(\text{Emission Ration} \times F_{100\%}) - C_{100\%}}{(C_{0\%} - C_{100\%}) + [\text{Emission Ratio} \times F_{100\%} - F_{0\%})]}\right\} * 100$ |

TABLE A-continued

| | Equation |
|---|---|
| % Inhibition | $\left\{1 - \dfrac{\% \, Phos_{Sample}}{\% \, Phos_{0\% \, Inhibition \, Ctl}}\right\} * 100$ |
| Z' (using Emission Ratio values) | $1 - \dfrac{3 * Stdev_{0\% \, Pho \, Crl} + 3 + Stdev_{0\% \, Inhibition}}{Mean_{0\% \, Pho \, Crl} - Mean_{0\% \, Inhibition}}$ |
| Difference Between Data Points (single point only) | $\lvert \% \, Inhibition_{Point \, 1} - \% \, Inhibition_{Point \, 2} \rvert$ |
| Development Reaction Interference (DRI) (no ATP control) | $\dfrac{Emission \, Ratio_{DRI \, Crl}}{Emission \, Ratio_{0\% \, Phos \, Crl}}$ |
| Test Compound Fluorescence Interference (TCFI) (check both Coumarin and Fluorescein emissions) | $\dfrac{Fl_{TCFI \, Crl}}{Fl_{0\% \, Inhibition \, Crl}}$ |

FI = Fluorescence Intensity
$C_{100\%}$ = Average Coumarin emission signal of the 100% Phos. Control
$C_{0\%}$ = Average Coumarin emission signal of the 0% Phos. Control
$F_{100\%}$ = Average Fluorescein emission signal of the 100% Phos. Control
$F_{0\%}$ = Average Fluorescein emission signal of the 0% Phos. Control
DRI = Development Reaction Interference
TCFI = Test Compound Fluorescence Interference Biological Example 2a Cell-Based Assay Preparation of cell lines useful for testing the soft MEK inhibitors in NF1 related cell-proliferation assays can be found in Basu et al. Nature 356: 713-715, 1992; and DeClue et al. Cell 69: 265-273, 1992. In addition, exemplary in vitro and in vivo models to determine efficacy of the soft MEK inhibitors described herein can be found in U.S. Pat. Nos. 8,211,875 and 8,487,004, which are incorporated by reference in their entireties.

Biological Example 2b

Cell-Based Assay

Alternatively, the following procedure can be used to measure cell-based activity. Test compounds were dissolved in DMSO in 10 mM stock. Cell Titer-Glo® 2.0 Luminescent cell viability assay reagent was purchased from Promega (Madison, Wis.). A375 and HCT116 cell lines were purchased from American Type Culture Collection (Manassas, Va.). For A375 cells, cell culture media was DMEM+10% FBS. Cell culture media are listed in the following table. For HCT116 cells, cell culture media was McCoy's 5A+10% FBS. All media were supplemented with 100 µg/mL of penicillin, and 100 µg/mL of streptomycin. Cultures were maintained at 37° C. in a humidified atmosphere of 5% $CO_2$ and 95% air.

Test compounds were diluted in DMSO solution with 10-dose and 3-fold dilutions in a source plate starting at 10 mM. 25 nL of each test compound was delivered from the source plate to each well of the 384-well cell culture plates (T=Final) by Echo 550. 25 µL of culture medium containing 2000 of A375 or HCT116 cells was added to each of the wells in duplicates of the cell culture plates (T=0 and T=Final). 25 µL of Cell Titer Glo 2.0 reagent was added to each well of cell culture plate (T=0). The contents were mixed on an orbital shaker for 2 min and incubated at room temperature for 15 min to stabilize luminescent signal.

Luminescence was recorded by Envision 2104 Multilabel Reader (PerkinElmer, Santa Clara, Calif.). The number of viable cells in culture was determined based on quantitation of the ATP present in each culture well. The cells in cell culture plate (T=Final) were incubated with the compounds at 37° C., 5% $CO_2$ for 72 hours. 25 µL of Cell Titer Glo 2.0 reagent was added to each well. The contents were mixed on an orbital shaker for 2 min and incubated at room temperature for 15 min to stabilize luminescent signal. Luminescence was recorded by Envision 2104 Multilabel Reader (PerkinElmer, Santa Clara, Calif.). The number of viable cells in culture was determined based on quantitation of the ATP present in each culture well. The GI50 curves were plotted using the GraphPad Prism 4 program based on a sigmoidal dose-response equation Y=Bottom+(Top-Bottom)/(1+10^((LogEC50−X)*HillSlope)). All parameters in the equation were calculated by GraphPad Prism 4 program. GI50 is the concentration of the compound calculated according to $[(T_i-T_z)/(C-T_z)]*100=50$ where $T_i$ is the row data of cells with test compounds at T=Final; $T_z$ is the row data of cells without compounds at T=0 h; C is the row data of cells with control compound staurosporine (Sigma-Aldrich) at T=72 h. Accordingly, GI50 is the value of $10^X$, where X was calculated by the Curve Fitting Equation when Y=50 using Excel.

Biological Example 3

S9 Stability Assays

Compounds were assessed for metabolic stability in human skin by assessing their rate of disappearance from human S9 skin fraction. Similarly, compounds were assessed for metabolic stability in human liver by assessing their rate of disappearance from human S9 liver fraction. The protocol below can be used to assess the difference between skin and hepatic metabolism.

The assay was carried out in 96-well microtiter plates at 37° C. Reaction mixtures (25 µL) contained a final concentration of 1 µM test compound, 2 mg/mL liver or skin S9 protein, and 1 mM NADPH in buffer (100 mM potassium phosphate, pH 7.4 buffer with 1 mM EDTA, 3 mM MgCl$_2$). At each of the time points (0, 15, 30, and 60 minutes), 150 µL of quench solution (100% acetonitrile with 0.1% formic acid) with internal standard was transferred to each well. Besides the zero minute controls, mixtures containing the same components except the NADPH were also prepared as the negative control. Verapamil or testosterone was included as a positive control to verify assay performance. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism was calculated as the disappearance of the test compound, compared to the 0-min control reaction incubations. Initial rates were calculated for the compound concentration and used to determine $t_{1/2}$ values and subsequently, the intrinsic clearance, $CL_{int}$= (0.693) (1/$t_{1/2}$ (min)) (mL incubation/mg of S9 protein).

Data for known, clinical MEK1 compounds ($C_1$-$C_7$) in this assay are provided below. Data for compounds within the scope of Formula (I) are provided in the Results section below.

| | Compound | | Liver S9 $t_{1/2}$ (min) | CLint (µL/min/ mg protein) |
|---|---|---|---|---|
| C1 | CI-1040 | | 33 | 10.37 |
| C2 | PD-0325901 | | 340 | 1.02 |
| C3 | Binemetinib | | 277 | 1.25 |

-continued
| | Compound | Liver S9 t₁/₂ (min) | CLint (μL/min/ mg protein) |
|---|---|---|---|
| C4 | Selumetinib 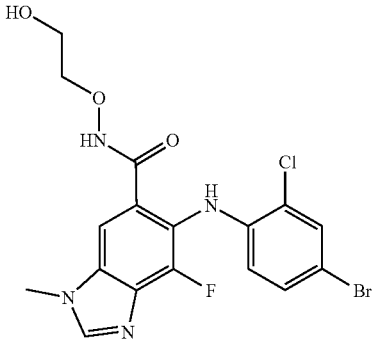 | 138 | 2.50 |
| C5 | GDC-0623 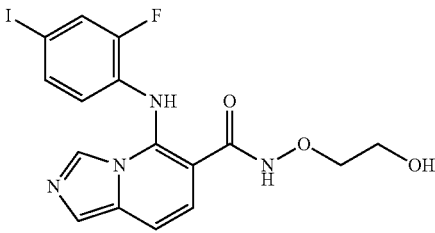 | 50 | 6.98 |
| C6 | Trametinib 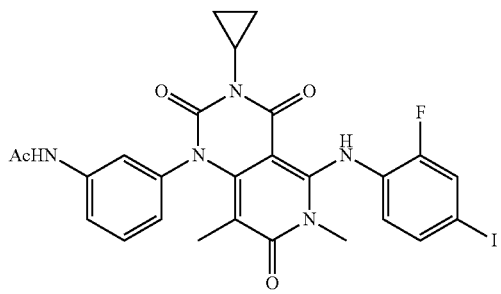 | 402 | 0.86 |
| C7 | Pimasertib 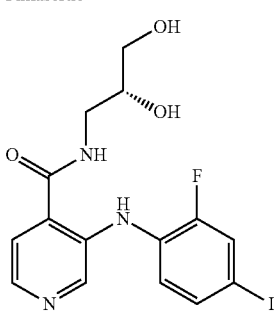 | 268 | 1.29 |
| C8 | 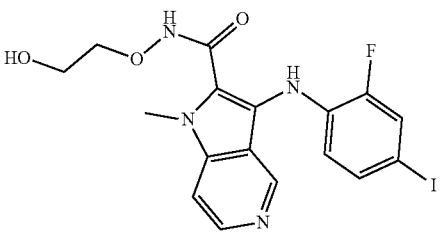 [SMILES: Cn1c(C(=O)NOCCO)c(Nc2ccc(I)cc2F)c2cnccc21] | 66 | 5.27 |

| Compound | Liver S9 $t_{1/2}$ (min) | CLint (μL/min/mg protein) |
|---|---|---|
| C9 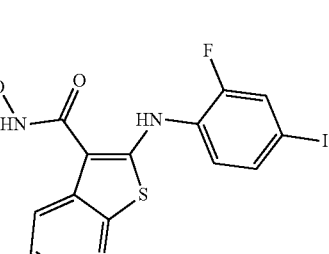 | 158 | 2.20 |

Biological Example 4

Microsomal Stability Assay

Metabolic stability of testing compound can be evaluated using human liver microsomes to predict intrinsic clearance. Human liver microsomes are obtained from Corning Gentest.

The assay is carried out in 96-well microtiter plates at 37° C. Reaction mixtures (25 μL) contain a final concentration of 1 μM test compound, 0.5 mg/mL liver microsomes protein, and 1 mM NADPH in buffer (100 mM potassium phosphate, pH 7.4 buffer with 3 mM $MgCl_2$). At each of the time points (0, 15, 30, and 60 minutes), 150 μL of quench solution (100% acetonitrile with 0.1% formic acid) with internal standard is transferred to each well. Verapamil is included as a positive control to verify assay performance. Plates are sealed and centrifuged at 4° C. for 15 minutes at 4000 rpm. The supernatant is transferred to fresh plates for LC/MS/MS analysis.

All samples are analyzed on LC/MS/MS using an AB Sciex API 4000 instrument, coupled to a Shimadzu LC-20AD LC Pump system. Analytical samples are separated using a Waters Atlantis T3 dC18 reverse phase HPLC column (20 mm×2.1 mm) at a flow rate of 0.5 mL/min. The mobile phase consists of 0.1% formic acid in water (solvent A) and 0.1% formic acid in 100% acetonitrile (solvent B).

The extent of metabolism is calculated as the disappearance of the test compound, compared to the 0-min time incubation. Initial rates are calculated for the compound concentration and used to determine $t_{1/2}$ values and subsequently, the intrinsic clearance, $CL_{int}=(0.693)(1/t_{1/2}(\text{min}))(g \text{ of liver/kg of body weight})(mL \text{ incubation/mg of microsomal protein})(45 \text{ mg of microsomal protein/g of liver weight})$.

Results for Biological Examples 1a, 2b, 2c, and 3

The following applies to the table below. NT indicates that the compound was not tested in a particular assay. Assay 1 is the biochemical MEK $IC_{50}$ (nM) assay as described in Biological Example 1a and as used for compounds 2 and 6; compounds 1, 3, 5, and 7-8 were tested using Biological Example 1b. Assay 2 is the A375 (BRAF) $GI_{50}$ (nM) cell-based assay as described in Biological Example 2c. Assay 3 is the HCT116 (Kras) $GI_{50}$ (nM) assay as described in Biological Example 2b. Assay 4 is the human liver S9 half-life stability assay as described in Biological Example 3. Assay 5 is the human liver S9 intrinsic clearance value (μL/min/mg protein) as described in Biological Example 3.

| Compound | | Assay | | | |
|---|---|---|---|---|---|
| | 1 | 2 | 3 | 4 | 5 |
| Ex. 1 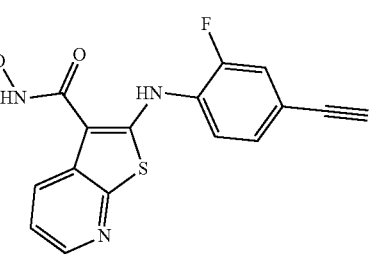 | 1030 | 141 | 348 | 29 | 11.84 |

-continued
| | | Assay | | | | |
|---|---|---|---|---|---|---|
| | Compound | 1 | 2 | 3 | 4 | 5 |
| Ex. 2 | 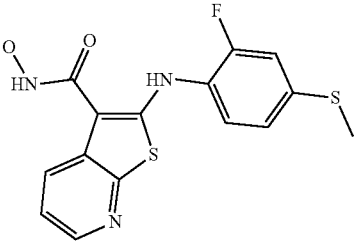 | 915 | 145 | 257 | 16 | 21.17 |
| Ex. 3 | 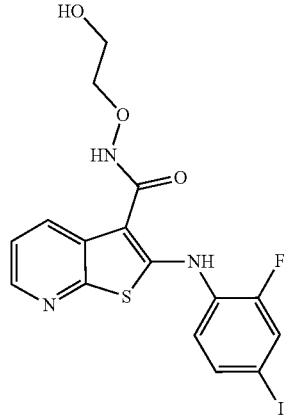 [SMILES: O=C(NOCCO)c1c(Nc2ccc(I)cc2F)sc2ncccc12] | 74 | NT | NT | 26 | 13.35 |
| Ex. 5 | 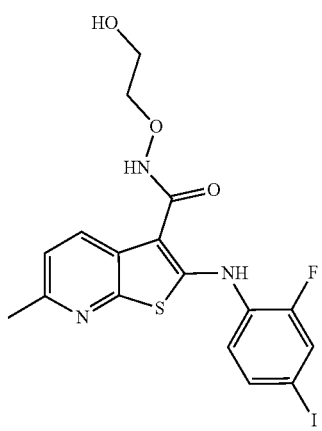 [SMILES: Cc1ccc2c(C(=O)NOCCO)c(Nc3ccc(I)cc3F)sc2n1] | 256 | NT | NT | 54 | 6.36 |
| Ex. 6 | 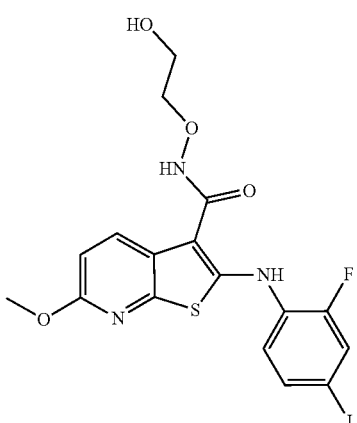 | 2910 | NT | NT | NT | — |

-continued

| Compound | | Assay | | | | |
|---|---|---|---|---|---|---|
| | | 1 | 2 | 3 | 4 | 5 |
| Ex. 7 | 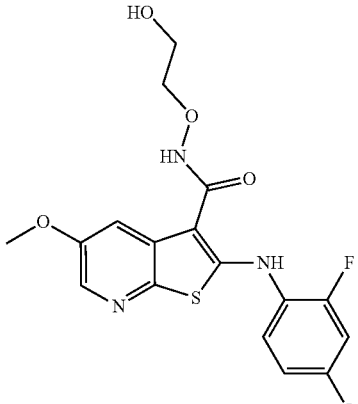 | 150 | NT | NT | 68 | 5.10 |
| Ex. 8 | 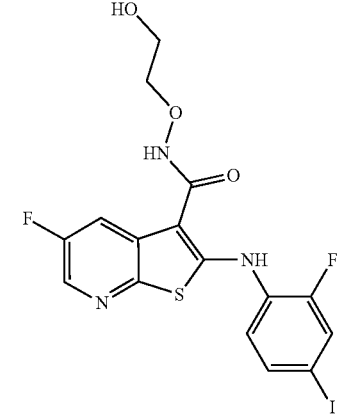 [SMILES: O=C(NOCCO)c1c(Nc2ccc(I)cc2F)sc2ncc(F)cc12] | 256 | NT | NT | 6 | 57.15 |

Biological Example 5

In Vivo Model

Study Procedures:

A topical formulation of a compound described herein along with a topical formulation of vehicle are applied to the skin of nude mice in duplicate. Skin is biopsied at discrete time intervals and bisected with half snap frozen in liquid nitrogen and half formalin fixed and paraffin embedded. Protein is isolated for Western blot analysis for p-ERK levels. p-ERK immunostaining is performed of FFPE sections for cell-specific analysis of p-ERK levels. Additional analysis includes H&E staining to investigate skin integrity.

A compound is assessed in suppressing p-ERK, a downstream biomarker of RAS/MAPK signaling in murine skin. In addition, proliferation of murine skin, apoptosis in murine skin, and histologic integrity of murine skin are also assessed.

Mice: 8 week old 129 mice obtained from Jackson laboratories are shaved prior to start of study. Approximately 21 mice were used for study. A compound is applied to the hairless dorsal skin of the mouse and at 12 hour intervals and skin biopsies are obtained prior to treatment, 24 hours, 72 hours and at 96 hours using 6 mm punch biopsies.

Western Blot analysis: For immunoblotting, epidermal skin is snap frozen in liquid nitrogen immediately afterbiopsy. The epidermis is lysed in lysis buffer and run on Western blots. Antibodies used for immunoblotting include rabbit anti-phospho-p44/42 MAPK (1:3000, Cell Signaling) and rabbit anti-p44/42 MAPK (1:3000, Cell Signaling), mouse anti-actin (1:5,000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry is performed on 5 µm paraffin sections. Antigen retrieval with enzyme treatment (1:1000) using standard protocols. Antibodies used were rabbit p-ERK (Cell Signaling, 4307S, 1:100). Bond Polymer Refine anti-rabbit HRP Detection (Leica Biosystems) was used according to manufacturer's protocol. Sections were then counterstained with hematoxylin, dehydrated and film coverslipped using a TissueTek-Prisma and Coverslipper (Sakura).

Histologic analysis: H&E is performed on 5 µM paraffin sections and tissue is examined to assess for cellular toxicity, inflammation or other changes in the integrity of murine skin.

Exogenous RAS activation in murine skin: The experiments are to be conducted in untreated murine skin. Alternatively, skin is pre-treated with TPA to enhance p-ERK levels. TPA-induced RAS/MAPK activation is performed with 96 hours of 12.5 uG TPA in 100 µL acetone to the skin of nude mice. Studies are performed 48 hours after TPA exposure.

T-test will be used to assess differences in p-ERK and Ki-67 in samples treated with topical MEK1 inhibitors compared to vehicle control.

Biological Example 6a

In Vivo Mouse Model

Compounds described herein are tested in a mouse model of NF1, e.g., genetically modified mouse model of NF1, a human dermal neurofibroma (or a cutaneous neurofibroma) xenograft to nude mouse model or both. For example, methods using the Nfl$^{flox/flox}$; Dhh-Cre mouse model described in Jousma et al. *Pediatr. Blood Cancer* 62: 1709-1716, 2015 can be used in this study. Magnetic resonance imaging (MRI) and volumetric measurements is used to measure tumor volumes.

Biological Example 6b

In Vivo Mouse Model

This study is designed to assess the skin toxicity and gross systemic toxicity of twice daily topical administration of a compound disclosed herein, as well as to evaluate the effect of metabolic lability on systemic toxicity.

Study Objective:

The primary objective of this study is to characterize the skin and systemic toxicity of twice daily topical application of a compound disclosed herein, applied for 25 days in mice. Secondary objectives included determination of the 25-day skin and plasma compound levels of formulations containing three dosages of compound of disclosed herein after application to 10% body surface area (BSA) murine skin; assessment of gross systemic toxicity from the application of compound disclosed herein after twice daily application to 10% BSA murine skin for 25 days; and determination of the correlation of skin and plasma compound levels with associated toxicity.

Duration:
25 days

Mice:
8 week old male C57BL/6J mice (Jackson Laboratories) are shaved prior to start of study and weekly. All experiments will be approved by the Stanford University Animal Care and Use Committee.

Intervention Arms:

| Concentration | Cmpd | No. of mice | % BSA | Application |
| --- | --- | --- | --- | --- |
| 0 | Topical vehicle | 10 | 10 | Twice daily 5 days per week |
| 0 | Oral vehicle | 4 | N/A | Daily oral gavage 5x/week |
| 1% | trametinib | 10 | 10 | Twice daily 5 days per week |
| 0.1% | Test Cmpd | 9 | 10 | Twice daily 5 days per week |
| 0.5% | Test Cmpd | 9 | 10 | Twice daily 5 days per week |
| 1% | Test Cmpd | 9 | 10 | Twice daily 5 days per week |
| 0.75 mg/kg | trametinib | 10 | N/A | Daily oral gavage 5x/week |

Compound Application:
Test compounds are dissolved in a 50% DMSO/50% propylene glycol vehicle. 0.125 mL of the following compounds are applied to the shaved dorsal back of mice (10% BSA) twice daily for 5 days per week for a total of 24 days. The second dose is applied 8 hours after first morning dose. All mice are shaved once per week at application site.

Oral trametinib is dissolved in 0.5% hydroxypropyl methylcellulose (Sigma-Aldrich) and 0.2% Tween-80 (Sigma-Aldrich) and administered by oral gavage (0.2 mL bolus or 10 mg/kg) once daily 5 days per week. These mice are also shaved weekly.

Weekly (Weeks 0-4):
body weight measurements weekly, starting week 0 until experiment end; photographs of dorsal back and face of each mouse weekly, starting week 0 until experiment end; skin; and gross stool analysis assessed weekly for heme color, starting week 0 until experiment end.

Week 4 (Experiment End):
Skin and blood are collected right before the last morning dose (N=3), 1 hour (N=3 mice), and 2 hours (N=3 mice) after final application; Blood draw: Plasma compound levels (LCMS); Skin biopsy: formalin fixed for histology and p-ERK staining, flash frozen for Western analysis and skin compound levels (LCMS)

Oversight:
The study will be conducted with oversight from Stanford IACUC committee.

Skin Biopsy and GI Tract Sampling:
Skin is wiped down with 100% ethanol and a 1 cm$^2$ biopsy is obtained from compound application site each mouse at the 25 day end of experiment (except as noted below). The skin is biopsied prior to final dose from 3 mice, 1 hour after last compound application from 3 mice, 2 hours after last compound application from 3 mice. Half of the specimen are immediately flash frozen for LCMS analysis and Western Blot Analysis. Half of the specimen is fixed for 24 hours in 10% formalin and then transferred to ethanol for immunohistochemistry. Gastrointestinal tract is also formalin fixed overnight then transferred to 70% ETOH for storage.

Western Blot Analysis:
For immunoblotting, total skin biopsies are lysed in lysis buffer and run on Western blots. Antibodies used for immunoblotting included rabbit anti-phospho-p44/42 MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry:
Immunohistochemistry is performed on 5 μm paraffin sections.

Antigen retrieval is accomplished with enzymatic treatment. Sections are blocked with 10% normal goat serum and subsequently incubated in phospho-p44/42 MAPK (Erk1/2) rabbit monoclonal antibody (Cell Signaling) or mouse anti-Ki-67 (Pharmingen) at 1:100 dilution for 60 minutes at room temperature. Detection is achieved with a peroxidase-conjugated anti-rabbit system (Leica Biosystem).

Histologic Analysis:
H&E is performed on 5 μM paraffin sections and tissue is examined to assess for cellular toxicity, inflammation or other changes in the integrity of murine skin.

Compound Level Analysis:
Liquid chromatography with mass spectrometry method (LCMS) is used to detect compound levels in the skin and plasma. Tissues are preprocessed prior to LCMS as follows.

Tissues are minced and incubated with collagenase and then finally homogenized using the stainless steel beads prior to LCMS analysis. Calibration curves and a QC test are run with each assay.

Biological Example 6b was carried out with the following arms: oral vehicle, oral Trametinib, topical vehicle, and topical Trametinib (1%). The study planned for the mice to be sacrificed at Day 25. However, at Day 18, several mice which were treated with topically-applied, 1% Trametinib were found dead, or had to be sacrificed due to unacceptable weight loss. The study was allowed to continue for the mice treated with oral trametinib.

Results

Kaplan Meier curves were analyzed to determine progression to skin toxicity for each arm as compared with vehicle. T-test were used to compare compound levels at each dosage. Ki-67+ cells and p-ERK expression were also assessed on a cellular level via immunostaining. Western blots informed semi-quantitative changes in p-ERK expression.

See Table 3 which shows that a topical application of Trametinib demonstrated significant toxicity. Compounds as disclosed and claimed herein are expected to demonstrate less systemic toxicity because of their greater metabolic lability, as demonstrated by their half-life in human liver S9 fractions.

TABLE 3

Survival Rates

| | Day | | | | | | | | | |
|---|---|---|---|---|---|---|---|---|---|---|
| | 0 | 3 | 6 | 9 | 12 | 15 | 18 | 21 | 24 | 25 |
| oral vehicle | 100% | 100% | 100% | 100% | 100% | 100% | 100% | 100% | 100% | 100% |
| oral Trametinib | 100% | 90% | 70% | 70% | 70% | 70% | 70% | 70% | 70% | 70% |
| topical vehicle | 100% | 100% | 100% | 100% | 100% | 100% | 100% | 100% | 100% | 100% |
| topical Trametinib (1%) | 100% | 100% | 100% | 100% | 100% | 80% | 0% | 0% | 0% | 0% |

Biological Example 7

Human Dermal Neurofibroma or Cutaneous Neurofibroma Explant Protocol

Dermal neurofibromas (or cutaneous neurofibromas) are benign tumors which develop in individuals affected with Neurofibromatosis-1 (NF1), a rare genetic disease caused by mutations in the NF1 gene, leading to downstream activation of the RAS/MAPK pathway. Recent studies have demonstrated that inhibition of MEK1 using systemic MEK inhibitors can suppress neurofibromas and other NF-1 related tumors in murine models. See, for example, *New Engl J Med* 2016, 375; 26; *J Clin Invest.* 2013, 123(1), 340-347; and *Pediatr Blood Cancer* 2015, 62(10), 1709-1716. This study establishes an in vitro neurofibroma explant model.

Study Objectives:

The primary objective was to assess the efficacy of a topically-formulated compound described herein in suppressing p-ERK, a downstream biomarker of RAS/MAPK signaling in neurofibroma explants. The secondary objectives was to assess permeability (where the compound was applied topically) of neurofibroma explants treated with a compound described herein.

Sample Collection and Eligibility

Primary dermal neurofibromas or cutaneous neurofibromas were obtained from patients with clinical or genetic diagnoses of NF1. Discarded human neurofibromas samples were obtained from the Stanford Surgery Clinic, using an approved human subjects protocol (Stanford IRB #18325). Specimens were identified under the direction of the Principal Investigator and placed in cell proliferation media (DMEM/F12 containing penicillin/streptomycin (0.1%); fungizone (40 μg/mL); B27 (without vitamin A).

Patients had the following data to be enrolled in the study: Patient was older than 18 years of age; patient were not undergoing chemotherapy treatment at time of biopsy; and patients met clinical and/or genetic diagnosis of NF1 based on presence of two of the following:
1. Six or more café-au-lait macules over 5 mm in diameter in prepubertal individuals and over 15 mm in greatest diameter in postpubertal individuals.
2. Two or more neurofibromas of any type or one plexiform neurofibroma.
3. Freckling in the axillary or inguinal regions.
4. Two or more Lisch nodules (iris hamartomas).
5. Optic glioma.
6. A distinctive osseous lesion such as sphenoid dysplasia or thinning of long bone cortex, with or without pseudarthrosis.
7. First-degree relative (parent, sibling, or offspring) with NF-1 by the above criteria.

Study Procedures

Samples were primary, untreated neurofibromas of at least 6 mm in size; samples were excised by a shave, punch biopsy or elliptical excision; samples had a histologic diagnosis of dermal neurofibroma or cutaneous neurofibroma. Specimens were identified under the direction of the Principal Investigator Specimens were chopped into 2 mm fragments and placed in 24-well plates containing cell proliferation media (DMEM/F12 containing penicillin/streptomycin (0.1%); fungizone (40 μg/mL); B27 (without vitamin A) and submerged in media with drug. For topical gel application, samples were placed in 96 well plates with epidermal surface exposed to air.

A topical gel formulation of a compound of Example 8, as well as a topical gel formulation of vehicle, were topically applied to the surface of human neurofibroma explants and harvested at 4 hours for analysis. The gel formulation was 1% hydroxypropyl cellulose in DMSO/PEG 400 1:1 (v/v). Harvested tissue was bisected and with half snap frozen and half fixed in 10% formalin and paraffin embedded for further analysis.

Western Blot Analysis:

For immunoblotting, total skin biopsies were lysed in lysis buffer and run on Western blots. Antibodies used for immunoblotting included rabbit anti-phospho-p44/42

MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry:

Immunohistochemistry was performed on 5 µm paraffin sections. Antigen retrieval with enzyme treatment (1:1000) using standard protocols. Antibodies used were rabbit p-ERK (Cell Signaling, 4307S, 1:100). Bond Polymer Refine anti-rabbit HRP Detection (Leica Biosystems) was used according to manufacturer's protocol. Sections were then counterstained with hematoxylin, dehydrated and film coverslipped using a TissueTek-Prisma and Coverslipper (Sakura).

Data Analysis:

Semi-quantative Western blot was used to assess differences in p-ERK in samples treated with a compound described herein compared to vehicle control.

Results:

FIGS. 1 and 2 show suppression of p-ERK in human cutaneous neurofibroma explants.

Study Management:

The study was conducted with oversight from an IRB with patient informed consent and HIPAA authorization.

Results:

FIGS. 1 and 2 show suppression of p-ERK in human cutaneous neurofibroma explants.

Biological Example 8 hERG Screening Assay hERG screening was conducted using a procedure similar to the procedure described by Piper et al. (Piper, D. R. et al., *Assay Drug Dev. Technol.* 2008, 6(2):213-223). The Predictor hERG FP assay (available from ThermoFisher, cat. no. PV5365) is a homogenous, fluorescence polarization biochemical-based format utilizing a membrane fraction containing hERG channel protein (Predictor hERG Membrane) and a high affinity, red-fluorescent hERG channel ligand (Predictor hERG Tracer Red). When the Predictor hERG Tracer ligand is bound to the hERG channel it produces high fluorescence polarization values. Compounds that bind to the hERG channel protein (competitors) displace the Predictor hERG Tracer Red resulting in decreased fluorescence polarization values.

Test compounds were solubilized in DMSO at 100× (or greater) of the desired starting concentration. Screening was conducted with a final concentration of 1% DMSO. For 10-point titrations, 3-fold serial dilutions were performed from the starting concentrations. The assay buffer used was 25 mM HEPES (pH 7.5), 15 mM KCl, 1 mM MgCl2, and 0.05% Pluronic F-127 (available from Sigma-Aldrich).

Predictor hERG membranes were stored as a 2× stock at −80° C. Each membrane lot was titrated to identify the concentration of membranes required to obtain ~70% bound tracer. Before setting up the assay the membranes were thawed in a 37° C. water bath and stored at room temperature. To avoid light scatter caused by large membrane particulates the membranes were sonicated until a homogeneous solution free of particulates is obtained. Thawed membranes were sonicated with a Branson Sonifer® 450 for 10 pulses (Duty cycle: 20%, Output Control: 3 out of 10, Timer: hold). The sample was returned to ice for 30 seconds followed by another 5-10 pulses until homogeneous. After sonication the membranes were stored at room temperature.

The tracer (E-4031), selectively blocks hERG K+ channels, and is available from Sigma Aldrich. E-4031 was stored as a 250× stock at −20° C. Prior to the assay, the tracer was thawed and stored at room temperature. The tracer was diluted in Assay Buffer to 4× with a final assay concentration of 1 nM.

384 well untreated low-volume polystyrene microplates (Corning Cat. #4511) were used for the assay. To each well was added 5 µL of 4× test compound diluted in Assay Buffer (4% DMSO), or 200 nL 100× test compound in 100% DMSO. An additional 4.8 µL of Assay Buffer was added to the assay plate. Each compound titration was performed in the absence and presence of E-4031. 10 µL of 2× Predictor hERG Membranes was added to the appropriate wells of the assay plate. 5 µL of 4× Predictor hERG Tracer Red was added to the appropriate assay wells. The assay plate was shaken on an orbital shaker for 20-30 seconds. The assay plate was covered and incubated for 3 hours at room temperature. The assay plate was read on a fluorescence plate reader (Tecan Safire$^2$) and the data was analyzed.

Each plate was run with a control representing 100% tracer displacement (the minimum polarization value) as identified by 30 µM E-4031 displacement of Predictor hERG Tracer Red from Predictor hERG Membranes. Assay wells consisted of 30 µM E-4031, Predictor hERG Membranes and Predictor hERG Tracer Red with 1% DMSO.

Each plate also comprised a control representing 0% tracer displacement from the Predictor hERG Membranes (the maximum polarization value). Assay wells consisted of Assay Buffer, Predictor hERG Membranes, and Predictor hERG Tracer Red with 1% DMSO.

Assay blank control wells consisted of Predictor hERG Membranes and Assay Buffer. The blank wells were used for background subtraction of raw parallel and perpendicular fluorescence values prior to the calculation of polarization values.

An 8-point titration of the known inhibitor, E-4031, in duplicate was included on each assay plate to ensure that the assay was performing within an expected $IC_{50}$ range.

The following controls were monitored for each concentration of test compound:

Test Compound Polarization Interference (TCPI):

A higher concentrations some test compounds may exhibit an additional non-hERG specific reduction in polarization values producing data that appears to be affecting a one-site binding model. This phenomenon is observed with membranes lacking the hERG channel protein suggesting the presence of a non-hERG component in the membrane prep that is binding the tracer. This non-specific interaction is displaced by certain compounds at higher concentrations resulting in a reduction in polarization values. The effect of the test compound on this non-specific interaction was tested in the presence of saturating concentrations of E-4031. Assay wells utilized to test for Test Compound Polarization Interference contained test compound, 30 µM E-4031, Predictor hERG Membranes, and Predictor hERG Tracer Red with 1% DMSO. Calculated TCPI values outside ±25% were flagged.

Test Compound Fluorescence Interference (TCFI):

Test Compound Fluorescence Interference was determined by comparing the total fluorescence for test compound wells with the total fluorescence values from the 0% and 100% inhibition control wells. TCFI values outside ±20% the controls were flagged. The following equations were used for each set of data points:

| | Equation |
|---|---|
| Background-Substracted Perpendicular Fluorescence Intensity ($FI_\perp$) | $RFU_{Test\ Compound} - RFU_{Assay\ Blank}$ |
| Background-Subtracted Parallel Fluorescence Intensity ($FI_\parallel$) | $G\text{-Factor} * (RFU_{Test\ Compound} - RFU_{Assay\ Blank})$ |
| Total Fluorescence Intensity (TFI) | $FI_\parallel + (2 * FI_\perp)$ |
| Test Compound Fluorescence Interferance (TCFI) | |
| If $TFI_{0\%\ Inhibition} > TFI_{100\%\ Inhibition}$ | |
| If $TFI_{Test\ Compound} > [Avg\ (TFI_{0\%\ Inhibition}) * 1.2]$ | $\left\{\dfrac{Avg\ TFI_{Test\ Compound}}{Avg\ TFI_{0\%\ Inhibition}} - 1\right\} * 100$ |
| If $TFI_{Test\ Compound} < [Avg\ (TFI_{0\%\ Inhibition}) * 1.2]$ And If $TFI_{Test\ Compound} > [Avg\ (TFI_{100\%\ Inhibition}) * 0.8]$ | 0 |
| If $TFI_{Test\ Compound} < [Avg\ (TFI_{100\%\ Inhibition}) * 0.8]$ | $\left\{\dfrac{Avg\ TFI_{Test\ Compound}}{Avg\ TFI_{100\%\ Inhibition}} - 1\right\} * 100$ |
| If $TFI_{100\%\ Inhibition} > TFI_{0\%\ Inhibition}$ | |
| If $TFI_{Test\ Compound} > [Avg\ (TFI_{100\%\ Inhibition}) * 1.2]$ | $\left\{\dfrac{Avg\ TFI_{Test\ Compound}}{Avg\ TFI_{100\%\ Inhibition}} - 1\right\} * 100$ |
| If $TFI_{Test\ Compound} < [Avg\ (TFI_{100\%\ Inhibition}) * 1.2]$ And If $TFI_{Test\ Compound} > [Avg\ (TFI_{0\%\ Inhibition}) * 0.8]$ | 0 |
| If $TFI_{Test\ Compound} < [Avg\ (TFI_{0\%\ Inhibition}) * 0.8]$ | $\left\{\dfrac{Avg\ TFI_{Test\ Compound}}{Avg\ TFI_{0\%\ Inhibition}} - 1\right\} * 100$ |
| mP | $\dfrac{FI_\parallel + FI_\perp}{FI_\parallel + FI_\perp} * 100$ |
| Test Compound Polarization Interference (TCPI) | $\left\{\dfrac{mP_{Test\ Compound\ +\ E\text{-}4031} - mP_{100\%\ Inhibition}}{mP_{0\%\ Inhibition} - mP_{100\%\ Inhibition}}\right\} * 100$ |
| % Inhibition | $\left\{1 - \dfrac{mP_{Test\ Compound} - mP_{Test\ Compound\ +\ E\text{-}4031}}{mP_{0\%\ Inhibition} - mP_{100\%\ Inhibition}}\right\} * 100$ |
| Z'* (using mP values) | $1 - \dfrac{3 * Std\ Dev_{0\%\ Inhibition} + 3 * Std\ Dev_{100\%\ Inhibition}}{Mean_{0\%\ Inhibition} - Mean_{100\%\ Inhibition}}$ |

Graphing Software: XLfit from IDBS was used for graphing. The dose response curve was curve fit to model number 205 (sigmoidal dose-response model). If the bottom of the curve did not fit between −20% and 20% inhibition, it was set to 0% inhibition. If the top of the curve did not fit between 70% and 130% inhibition, it was set to 100% inhibition.

Results

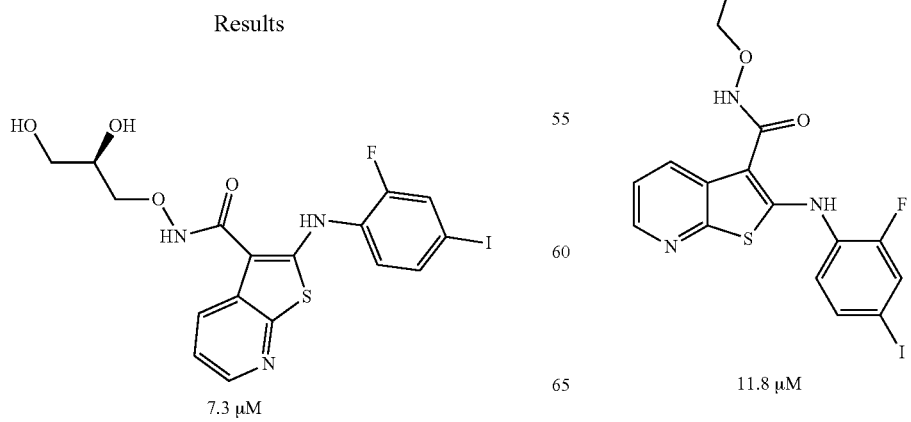

Ex. 3

7.3 μM 11.8 μM

Biological Example 10

MDCK-MDR1 Bi-Directional Transport Assay

MDCK-MDR1 is a stable-transfected cell line originating from MDCK cells, with over-expression of human MDR1 gene. The cell line is widely used for the identification and characterization of P-gp substrates and inhibitors.

MDCK-MDR1 cells are plated into 96-well Millipore Millicell-96 plates at 7,500 cells/75 μL/well and incubated for three days at 37° C. with 5% CO2. Cells are washed with Hank's Balanced Salt Solution (HBSS) with 5 mM HEPES for 30 minutes before starting the experiment. Test compound solutions are prepared by diluting DMSO stock into HBSS buffer, resulting in a final DMSO concentration of 0.1%. Prior to the experiment, cell monolayer integrity is verified by transendothelial electrical resistance (TEER). Transport experiment is initiated by adding test compounds to the apical (75 μL) or basal (250 μL) side. Transport plates are incubated at 37° C. in a humidified incubator with 5% CO2. Samples are taken from the donor and acceptor compartments after one hour and analyzed by liquid chromatography with tandem mass spectrometry (LC/MS/MS).

Digoxin is used as reference control.

Apparent permeability (Papp) values are calculated using the following equation: Papp=(dQ/dt)/A/C0; where dQ/dt is the initial rate of amount of test compound transported across cell monolayer, A is the surface area of the filter membrane, and C0 is the initial concentration of the test compound, calculated for each direction using a 4-point calibration curve by LC/MS/MS.

Net flux ratio between the two directional transports is calculated by the following equation: Ratio=Papp, B-A/Papp, A-B; where Papp, B-A and Papp, A-B represent the apparent permeability of test compound from the basal-to-apical and apical-to-basal side of the cellular monolayer, respectively.

Recovery is calculated based on the compound concentration at the end of the experiment, compared to that at the beginning of the experiment, adjusted for volumes.

A net flux ratio greater than two is considered a positive result for substrate determination. To further confirm whether the efflux activity observed for any test compounds is due to P-gp mediated transport, similar bi-directional transport studies in the presence of a potent P-gp inhibitor, such as GF120918, can be done. If the addition of a known P-gp inhibitor to the experiment reduces the net flux ratio by a significant amount (more than 50% reduction or reduces the ratio to close to unity), it is likely that the compound tested is a P-gp substrate.

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound, selected from the group consisting of:

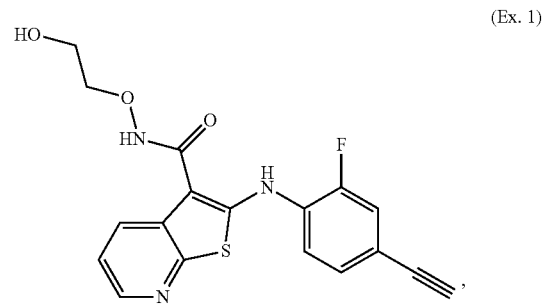

(Ex. 1)

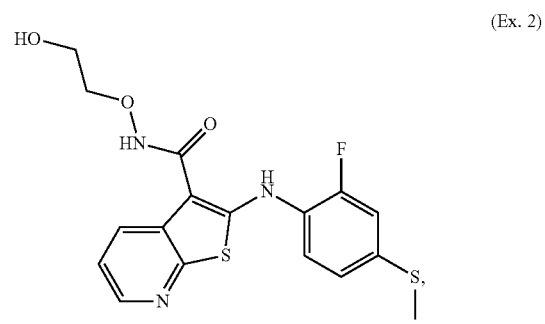

(Ex. 2)

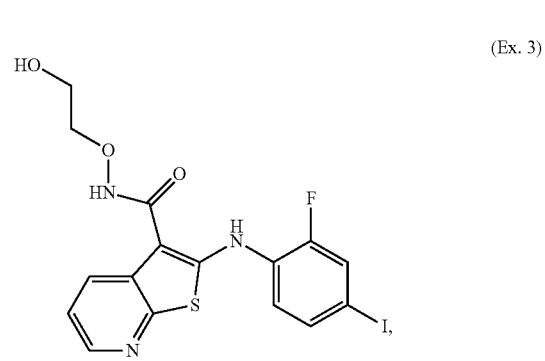

(Ex. 3)

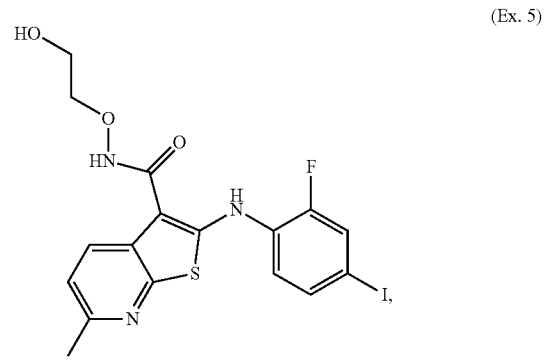

(Ex. 5)

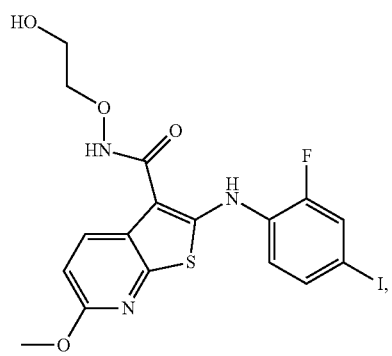
(Ex. 6)
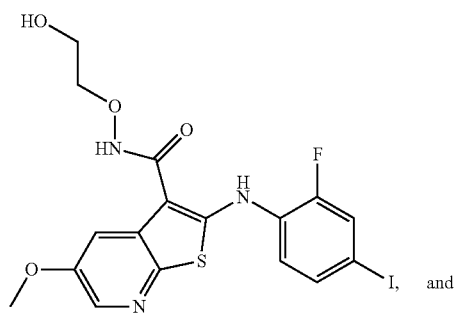
(Ex. 7)
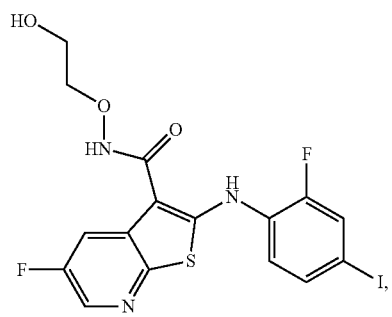
(Ex. 8)
or a pharmaceutically acceptable salt thereof.
2. A pharmaceutical composition comprising a compound selected from the group consisting of:
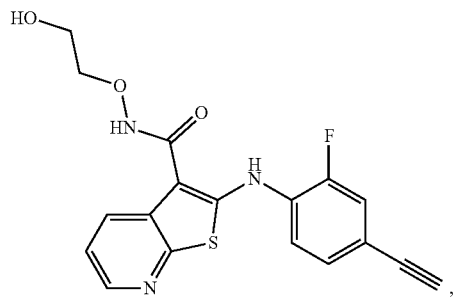
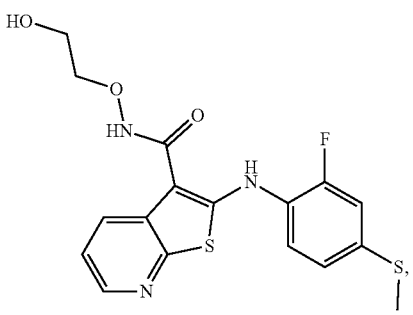
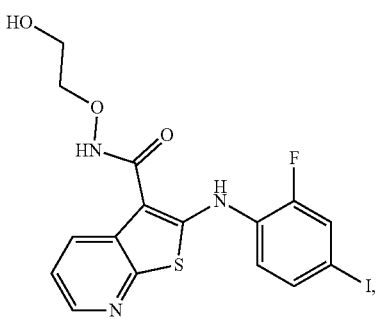
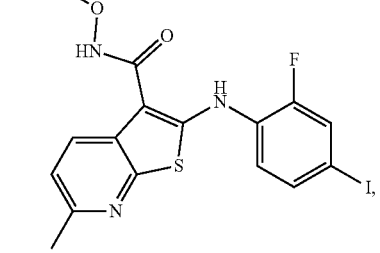
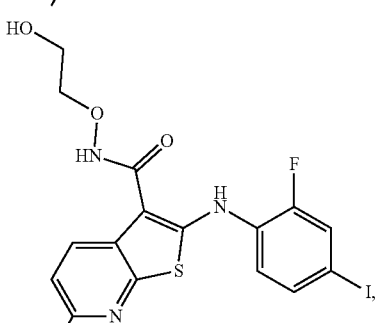
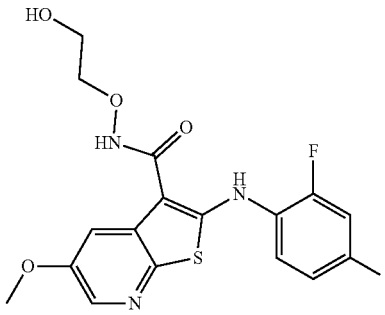
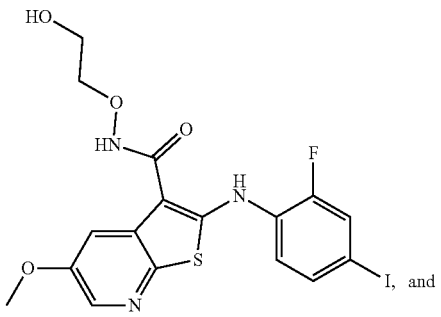

-continued

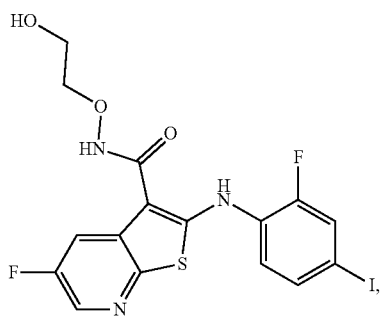 [SMILES: O=C(NOCCO)c1c(Nc2ccc(I)cc2F)sc2ncc(F)cc12]

or a pharmaceutically acceptable salt thereof; and
a pharmaceutically acceptable carrier.

3. A method of treating a MEK-inhibitor responsive dermal disorder or a MEK-mediated dermal disorder comprising administering a compound selected from the group consisting of:

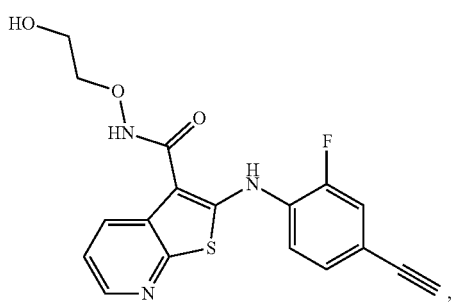

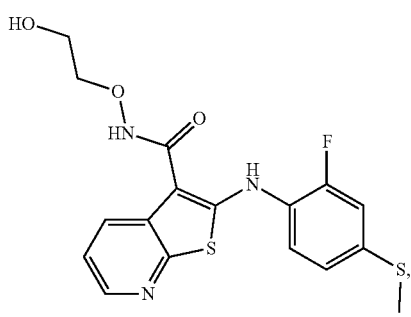

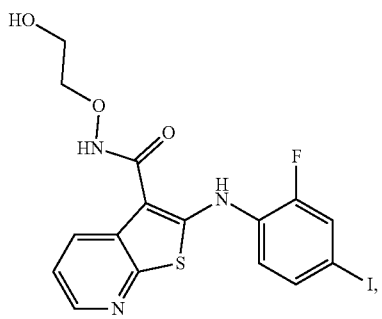

-continued

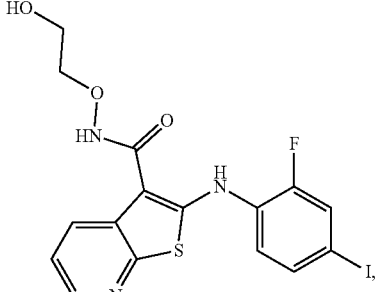

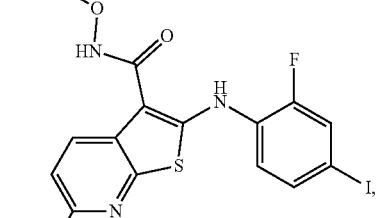

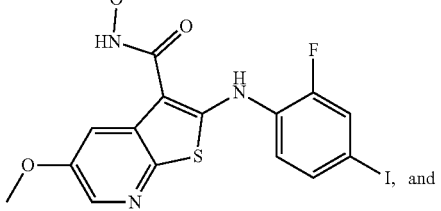

I, and

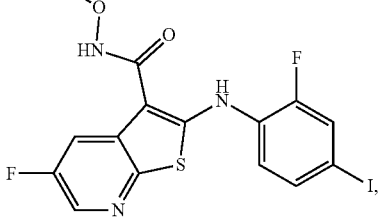

or a pharmaceutically acceptable salt thereof,
wherein the MEK-inhibitor responsive dermal disorder or the MEK-mediated dermal disorder is selected from the group consisting of a dermal rasopathy, a neurofibromatosis type 1, a dermal neurofibroma, a subdermal neurofibroma, and a superficial plexiform neurofibroma.

4. The method of claim 3, wherein the MEK-inhibitor responsive dermal disorder or the MEK-mediated dermal disorder is a neurofibromatosis type 1.

5. The method of claim 3, wherein the MEK-inhibitor responsive dermal disorder or the MEK-mediated dermal disorder is a dermal neurofibroma.

6. The method of claim 3, wherein the MEK-inhibitor responsive dermal disorder or the MEK-mediated dermal disorder is a subdermal neurofibroma.

7. The method of claim 3, wherein the MEK-inhibitor responsive dermal disorder or the MEK-mediated dermal disorder is a superficial plexiform neurofibroma.

8. The method of claim 3, wherein the MEK-inhibitor responsive dermal disorder or the MEK-mediated dermal disorder is a dermal rasopathy.

9. The method of claim 8, wherein the dermal rasopathy is selected from the group consisting of psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

10. The method of claim 3, wherein the compound is administered topically, subcutaneously, transdermally, intradermally, or intralesionally.

11. The compound of claim 1, represented by the formula:

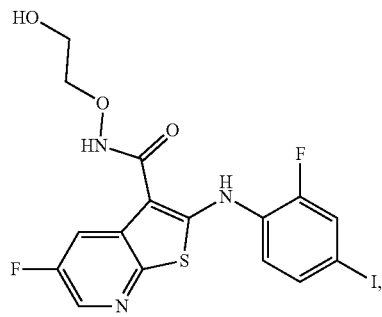 [SMILES: O=C(NOCCO)c1c(Nc2ccc(I)cc2F)sc2ncc(F)cc12]

or a pharmaceutically acceptable salt thereof.

12. The pharmaceutical composition of claim 2, wherein the compound is represented by the formula:

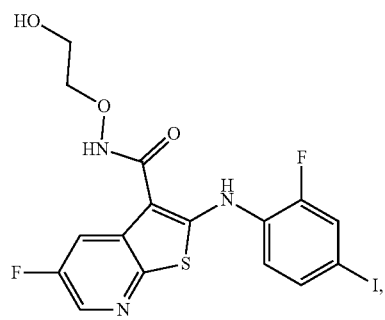 [SMILES: O=C(NOCCO)c1c(Nc2ccc(I)cc2F)sc2ncc(F)cc12]

or a pharmaceutically acceptable salt thereof.

13. The method of claim 3, wherein the compound is represented by the formula:

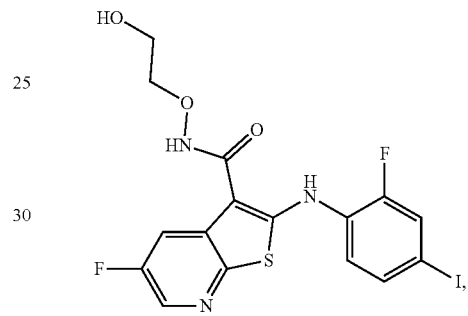

or a pharmaceutically acceptable salt thereof.

* * * * *